US011412962B1

(12) United States Patent
Miller et al.

(10) Patent No.: US 11,412,962 B1
(45) Date of Patent: Aug. 16, 2022

(54) DEVICES, SYSTEMS, AND METHODS FOR IDENTIFYING IMPROVING HEALTH FOR CHRONIC HEALTH CONDITION MANAGEMENT

(71) Applicant: Tula Health, Inc., Kaysville, UT (US)

(72) Inventors: David Miller, Morgan, UT (US); Devin Miller, Morgan, UT (US); Michael Jones, Provo, UT (US); David Derrick, Provo, UT (US)

(*) Notice: Subject to any disclaimer, the term of this patent is extended or adjusted under 35 U.S.C. 154(b) by 27 days.

(21) Appl. No.: 16/829,836

(22) Filed: Mar. 25, 2020

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0022* (2013.01); *A61B 5/1455* (2013.01); *A61B 5/1459* (2013.01); *A61B 5/1473* (2013.01); *A61B 5/1477* (2013.01); *A61B 5/14551* (2013.01); *A61B 5/167* (2013.01); *A61B 5/4842* (2013.01); *A61B 5/4845* (2013.01);
(Continued)

(58) Field of Classification Search
CPC ... A61B 5/1459; A61B 5/1477; A61B 5/1473; A61B 5/14503; A61B 5/14865; A61B 5/1411; A61B 5/1427; A61B 5/14551; A61B 5/1455; A61B 5/0075; A61B 5/0531; A61B 5/4842; A61B 5/746; A61B 5/14532; A61B 5/6801
See application file for complete search history.

(56) References Cited

U.S. PATENT DOCUMENTS

| 4,960,128 A | 10/1990 | Gordon et al. |
| 7,317,938 B2 | 1/2008 | Lorenz et al. |

(Continued)

FOREIGN PATENT DOCUMENTS

| CA | 2990843 A1 | 3/2017 |

OTHER PUBLICATIONS

Zawn Villines, "What to know about fasting blood sugar?", Mar. 22, 2019, Medical News Today (Year: 2019).*

*Primary Examiner* — Daniel L Cerioni
*Assistant Examiner* — Jonathan E. Cooper
(74) *Attorney, Agent, or Firm* — Miller IP Law LLC

(57) ABSTRACT

Systems, methods, and devices of a health device network may include: a non-invasive glucometer that non-invasively measures analyte levels; an invasive glucometer communicatively coupled directly to the non-invasive glucometer; a cloud-based server communicatively coupled to the non-invasive glucometer or the invasive glucometer; a user device communicatively coupled to the cloud-based server; and/or a user interface that displays the invasive glucose measurement, the non-invasive glucose measurement, a data batch, and/or processed data to the user. The non-invasive glucometer and/or the invasive glucometer may aggregate an invasive glucose measurement and a non-invasive glucose measurement into the data batch. A data analytics application on the cloud-based server may be configured to: integrate the invasive glucose measurement and the non-invasive glucose measurement; identify a correlation between the invasive glucose measurement and the non-invasive glucose measurement; and/or generate a predictive model based on the invasive glucose measurement and the non-invasive glucose measurement.

20 Claims, 34 Drawing Sheets

(51) Int. Cl.
- *A61B 5/16* (2006.01)
- *A61B 5/1459* (2006.01)
- *A61B 5/1473* (2006.01)
- *A61B 8/04* (2006.01)
- *A61B 8/00* (2006.01)
- *A61B 5/1455* (2006.01)
- *A61B 5/1477* (2006.01)
- *G16H 50/30* (2018.01)
- *G16H 10/40* (2018.01)

(52) U.S. Cl.
CPC ............ *A61B 5/4875* (2013.01); *A61B 5/742* (2013.01); *A61B 5/746* (2013.01); *A61B 8/04* (2013.01); *A61B 8/461* (2013.01); *G16H 10/40* (2018.01); *G16H 50/30* (2018.01); *A61B 2562/0242* (2013.01)

(56) References Cited

U.S. PATENT DOCUMENTS

| | | | |
|---|---|---|---|
| 7,822,452 | B2 | 10/2010 | Schurman et al. |
| 8,571,618 | B1 | 10/2013 | Lamego et al. |
| 8,732,188 | B2 | 5/2014 | Doniger et al. |
| 8,986,209 | B2 | 3/2015 | Brauker et al. |
| 8,998,809 | B2 | 4/2015 | Kiani |
| 10,045,820 | B2 | 8/2018 | Youngquist et al. |
| 10,348,866 | B2 | 7/2019 | Yin et al. |
| 2005/0196821 | A1* | 9/2005 | Monfre ............... A61B 5/1455 435/14 |
| 2015/0164389 | A1* | 6/2015 | Varsavsky ............ G01N 21/59 600/316 |
| 2016/0270740 | A1* | 9/2016 | Raisoni ............... A61B 5/1459 |
| 2017/0127983 | A1* | 5/2017 | Spegazzini ......... A61B 5/1495 |
| 2019/0038478 | A1 | 2/2019 | Lai et al. |
| 2019/0246914 | A1* | 8/2019 | Constantin .......... A61B 5/7435 |
| 2021/0153786 | A1* | 5/2021 | Parker .................. G16H 40/67 |

* cited by examiner

DEVICES, SYSTEMS, AND METHODS FOR IDENTIFYING IMPROVING HEALTH FOR CHRONIC HEALTH CONDITION MANAGEMENT

BACKGROUND

The symptoms of a chronic health condition can be a significant factor in the quality of life for an individual experiencing the chronic health condition. Proper management of the chronic health condition can lead to outcomes which greatly improve the individual's quality of life compared to outcomes experiences when the chronic health condition is improperly and/or inadequately managed. For example, proper management of a chronic health condition may include taking regular measurements of various body functions, either directly or indirectly. Such measurements may provide critical information necessary for proper management of the chronic health condition. Obtaining measurements may be challenging and/or time-consuming, and the individual may accordingly be unlikely to obtain the measurements. Without the measurements, the chronic health condition may be improperly and/or inadequately managed, leading to poor outcomes for the individual where the individual experiences serious, even life-threatening symptoms of the chronic health condition.

BRIEF DESCRIPTION OF DRAWINGS

The present description will be understood more fully from the detailed description given below and from the accompanying drawings of various embodiments, which description is not to be taken to limit the present embodiment to the specific embodiments but are for explanation and understanding. Throughout the description, the drawings may be referred to as drawings, figures, and/or FIGS.

DETAILED DESCRIPTION

Figure 1A:
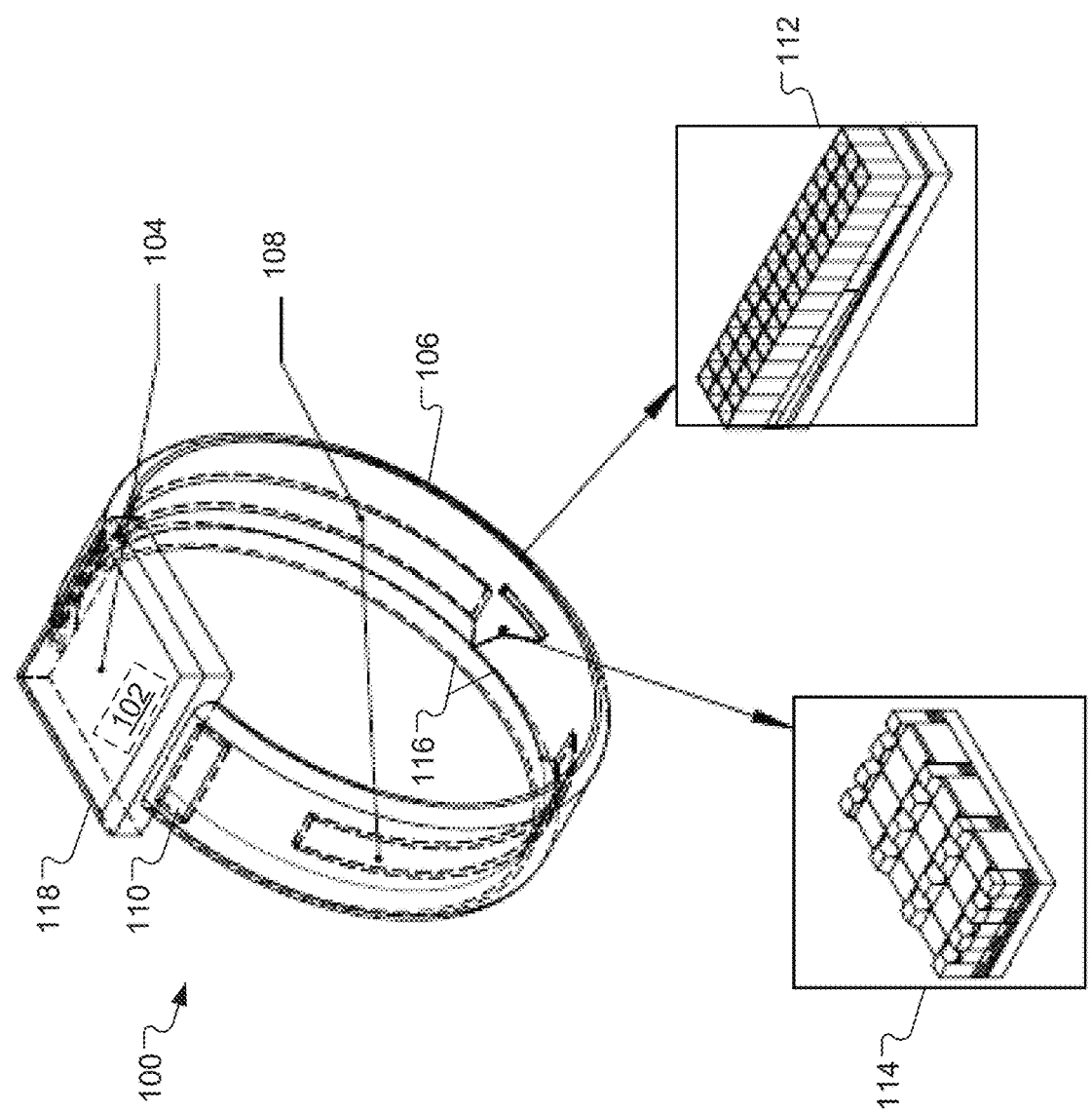
FIG. 1A illustrates a wearable device with integrated sensors, according to an embodiment.

Devices, methods and systems for chronic health condition management as disclosed herein will become better understood through a review of the following detailed description in conjunction with the figures. The detailed description and figures provide merely examples of the various embodiments described herein. Those skilled in the art will understand that the disclosed examples may be varied, modified, and altered and not depart from the scope of the embodiments described herein. Many variations are contemplated for different applications and design considerations; however, for the sake of brevity, the contemplated variations may not be individually described in the following detailed description.

Throughout the following detailed description, example embodiments of various methods and systems for chronic health condition management are provided. Related elements in the example embodiments may be identical, similar, or dissimilar in different examples. For the sake of brevity, related elements may not be redundantly explained in multiple examples except to highlight dissimilar features. Instead, the use of a same, similar, and/or related element names and/or reference characters may cue the reader that an element with a given name and/or associated reference character may be similar to another related element with the same, similar, and/or related element name and/or reference character in an example embodiment explained elsewhere herein. Elements specific to a given example may be described regarding that particular example embodiment. A person having ordinary skill in the art will understand that a given element need not be the same and/or similar to the specific portrayal of a related element in any given figure or example embodiment in order to share features of the related element.

Same may refer to sharing all features and similar may refer to sharing a substantial number of features or sharing materially important features even if a substantial number of features are not shared. May should be interpreted in the permissive sense and should not be interpreted in the indefinite sense. Additionally, use of is regarding embodiments, elements, and/or features should be interpreted to be definite only regarding a specific embodiment and should not be interpreted as definite regarding the invention as a whole. Furthermore, references to the disclosure and/or this disclosure may refer to the entirety of the writings of this document and the entirety of the accompanying illustrations, which extends to all the writings of each subsection of this document, including the Title, Background, Brief description of the Drawings, Detailed Description, Claims, and Abstract.

Where multiples of a particular element are shown in a FIG., and where it is clear that the element is duplicated throughout the FIG., one label may be provided for the element despite multiple instances of the element being present in the FIG. Accordingly, other instances in the FIG. of the element having identical or similar structure and/or function may not be redundantly labeled. A person having ordinary skill in the art will recognize based on the disclosure herein redundant and/or duplicated elements of the same FIG. Despite this, redundant labeling may be included where helpful in clarifying the structure of the depicted example embodiments.

A conventional system for chronic health condition management, such as a glucose monitoring system for managing diabetes, may include a measurement component, an analysis component, and a user interface. The measurement component may measure an analyte of a user. The measurement component may take a measurement of the analyte invasively, minimally invasively, and/or non-invasively. The analysis component may determine an amount of the analyte based on the measurement, and the user interface may display the amount to the user. Some glucose monitoring systems, for example, may have a lancet for pricking the user to draw blood from the user, a test strip onto which the blood is placed, and an analysis and display unit that determines the amount of glucose in the blood and displays the amount to the user. Some glucose monitoring systems may include a probe that continually measures glucose in the user's interstitial fluids. Some glucose monitoring systems measure glucose non-invasively by processing light reflected from and/or passed through a body part of the user.

Invasive monitoring systems have become a bane to individuals with diabetes. Lancet pricks are painful and, depending on the frequency required and the specific user's sensitivity to the pricks, can cause ongoing discomfort and pain for the user. The use of a large number of lancets and/or test strips frequently, especially multiple times per day, may lead to the spread of disease by a careless user. Furthermore, individuals may dread the process enough to avoid it completely, which may lead to poor management of the health condition. The individual may experience severe symptoms due to poor management.

Minimally invasive systems may require penetrating the user's skin, such as by an incision through which a probe is inserted. Minimally invasive systems may not be as accurate as invasive monitoring systems, and thus may incorrectly diagnose a state of an analyte. This may be due to a "time dilation" where the interstitial fluid does not reflect the current blood glucose levels, but rather is delayed by up to 20 minutes. For example, a minimally invasive system may indicate the user is within a safe range when the user is actually hyperglycemic or hypoglycemic. This may cause the user to unknowingly experience adverse symptoms of hyperglycemia or hypoglycemia. Accordingly, minimally invasive systems may be inadequate in properly managing the user's chronic health condition.

Non-invasive monitoring systems may be susceptible to drift of the measurements due to the influence of other variables related to the analyte. For example, the user's hydration level may change, which may change a percentage of the user's blood that is glucose without changing an absolute amount of blood glucose. This may similarly result in the non-invasive monitoring system indicating the user is in a safe range when the user is actually hypoglycemic or hyperglycemic.

Systems, devices, and methods for chronic health condition management as described herein may include an invasive measurement device, a non-invasive measurement device, a server, a user interface, and a network over which the measurement devices, the server, and the interface communicate. The invasive measurement device may take a first analyte isolation measurement. The non-invasive measurement device may take a second analyte isolation measurement concurrently with the first analyte measurement. The non-invasive measurement device may take continuous or semi-continuous analyte measurements after the analyte isolation measurement. The continuous or semi-continuous analyte measurements may measure changes in the analyte from the first or second analyte isolation measurement. The first analyte isolation measurement, second analyte isolation measurement, and/or the continuous or semi-continuous analyte measurements may be communicated to the server and/or the user interface. Together, the invasive measurement device, the non-invasive measurement device, the server, and/or the user interface may form a continuous analyte monitoring system. The continuous analyte monitoring system may reduce the user's pain and/or discomfort from frequent invasive measurement, eliminate non-analyte variables, and provide continuous information that the user may utilize to control variation of the analyte.

FIG. 1A illustrates a wearable device 100 with integrated sensors 112 and/or 114, according to an embodiment. The elements described regarding FIG. 1 may, in various embodiments, be the same as and/or similar to other similarly named elements described and/or illustrated herein. In one embodiment, the wearable device 100 may be configured to take physiological measurements of a user. The wearable device 100 may include a housing 118 and a band 106 that are configured or shaped to attach to a body of the user. In one embodiment, the wearable device 100 may include a wrist-worn device that may be configured to attach to a wrist or arm of the user. In another embodiment, the wearable device 100 may be attached to a head of the user using a headband, to a chest of the user using a chest band, to an ankle of the user using an ankle band, or otherwise attached to a body of the user using a sweatband, bandage, band, watch, bracelet, ring, adherent, or other attachments and connections.

The wearable device 100 may include a processing device 102, a display device 104, the band 106, a power source 108, a processing unit 110, a first sensor 112, and/or a second sensor 114. In one embodiment, the processing device 102 and the display device 104 may be integrated into the housing 118 of the wearable device 100. In another embodiment, the power source 108, the processing unit 110, the first sensor 112, and/or the second sensor 114 may be integrated into the band 106 of the wearable device 100. In one embodiment, the band 106 may include a cavity that the power source 108, the processing unit 110, the first sensor 112, and/or the second sensor 114 may be stored in. In another embodiment, the band 106 may be formed or molded over the power source 108, the processing unit 110, the first sensor 112, and/or the second sensor 114. In another embodiment, the power source 108, the first sensor 112, and/or the second sensor 114 may be connected to the processing unit 110 and/or the processing device 102 by one or more electrical trace(s) or circuit(s) 116 (such as flexible circuit boards).

The processing device 102 and/or the processing unit 110 may provide an output based on an input. In an embodiment, the processing device 102 and/or the processing unit 110 may include a central processing unit, a graphics processing unit, a vision processing unit, a tensor processing unit, a neural processing unit, a physics processing unit, a digital signal processor, an image signal processor, a synergistic processing element, a field-programmable gate array, a sound chip, a microprocessor, a multi-core processor, and so forth.

In one embodiment, the first sensor 112 may include a miniaturized spectrometer. In another embodiment, the second sensor 114 may include a miniaturized impedance sensor. In another embodiment, the first sensor 112 and/or the second sensor may include a temperature sensor, a viscosity sensor, an ultrasonic sensor, a humidity sensor, a heart rate sensor, a dietary intake sensor, an electrocardiogram (EKG) sensor, a galvanic skin response sensor, a pulse oximeter, an optical sensor, and so forth. In another embodiment, the wearable device 100 may include other sensors integrated or attached to the band 106 or the housing 118. In another embodiment, the wearable device 100 may be communicatively coupled to the wearable device 100, such as sensors of other devices or third-party devices. The first sensor 112 and/or the second sensor 114 may be configured to take measurements from a user non-invasively, such as by electrical and/or optical interrogation, and so forth.

The first sensor 112 and/or the second sensor 114 may be coupled to the processing unit 110. The processing unit 110 may be configured to manage or control the first sensor 112, the second sensor 114, and/or the power source 108. In one embodiment, the processing unit 110 may control a frequency or rate over time that the first sensor 112 and/or the second sensor 114 take measurements, a wavelength or optical frequency at which the first sensor 112 and/or the second sensor 114 take measurements, a power consumption level of the first sensor 112 and/or the second sensor 114, a sleep mode of the first sensor 112 and/or the second sensor 114 and so forth. In another embodiment, the processing unit 110 may control or adjust measurements taken by the first sensor 112 and/or the second sensor 114 take measurements to remove noise, reduce a signal to noise ratio, dynamically adjust the number of measurements taken over time, and so forth.

In another embodiment, the power source 108 may be coupled to the processing unit 110. The power source 108 may include a battery, a solar panel, a kinetic energy device, a heat converter power device, a wireless power receiver, and so forth. The processing unit 110 may be configured to transfer power from the power source 108 to the processing device 102, the display device 104, the first sensor 112, the second sensor 114, and/or other devices or units of the wearable device 100. In one embodiment, the processing unit 110 may be configured to regulate an amount of power provided from the power source 108 to the processing device 102, the display device 104, the first sensor 112, the second sensor 114, and/or other devices or units of the wearable device 100. In another embodiment, the wearable device 100 may include a power receiver to receive power to recharge the power source 108. For example, the power receiver may include a wireless power coil, a universal serial bus (USB) connector, a thunderbolt connector, a mini USB connector, a micro USB connector, a USB-C connector, and so forth. The power receiver may be coupled to the processing unit 110, the processing device 102, the power source 108, and so forth.

In one embodiment, the processing unit 110 may be configured to regulate an amount of power provided from the power receiver to the power source 108. In another embodiment, the processing unit 110 may include a power management unit configured to control battery management, voltage regulation, charging functions, direct current (DC) to DC conversion, voltage scaling, power conversion, dynamic frequency scaling, pulse-frequency modulation (PFM), pulse-width modulation (PWM), amplification, and so forth. In another embodiment, the processing unit 110 may include a communication device configured to send and/or receive data via a cellular communication channel, a wireless communication channel, a Bluetooth® communication channel, a radio communication channel, a WiFi® communication channel, a USB communication channel, an fiber-optic communication channel, and so forth.

The processing device 102 may include a processing device, a data storage device, a communication device, a graphics processor, and so forth. In one embodiment, the processing device 102 may be coupled to the processing unit 110, the power source 108, the first sensor 112, and/or the second sensor 114. In one embodiment, the processing device 102 may be configured to receive measurement data from the processing unit 110, the first sensor 112, and/or the second sensor 114. In one embodiment, the processing device 102 may be configured to process the measurement data and display information associated with the measurement data at the display device 104. In another embodiment, the processing device 102 may be configured to communicate the measurement data to another device. In one embodiment, the other device may process the measurement data and provide information associated with the measurement data to the user or another individual. In another embodiment, the other device may process the measurement data and provide results, analytic information, instructions, and/or notifications to the processing device 102 to provide to the user. The wearable device 100 may communicate information associated with the measurement data or information related to the measurement data to a user via the display device 104, a buzzer, a vibrator, a speaker, a microphone, and so forth.

In another embodiment, the wearable device 100 may be part of a system connected to other devices. For example, the wearable device 100 may be configured to send and/or receive data with another device. In one embodiment, the wearable device 100 may be configured to receive data from another measurement device, aggregate the received data with measurement data from the first sensor 112 and/or the second sensor 114, analyze the aggregated data, and provide information or notifications associated with the analyzed data.

Figure 1C:
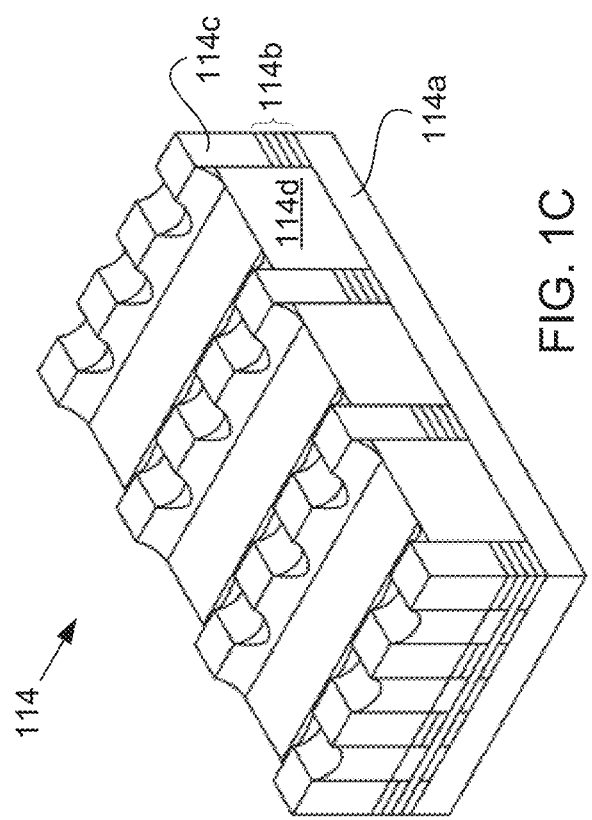
FIG. 1C illustrates a perspective view of a second sensor that may be integrated into the wearable device illustrated in FIG. 1A, according to an embodiment.
Figure 1B:
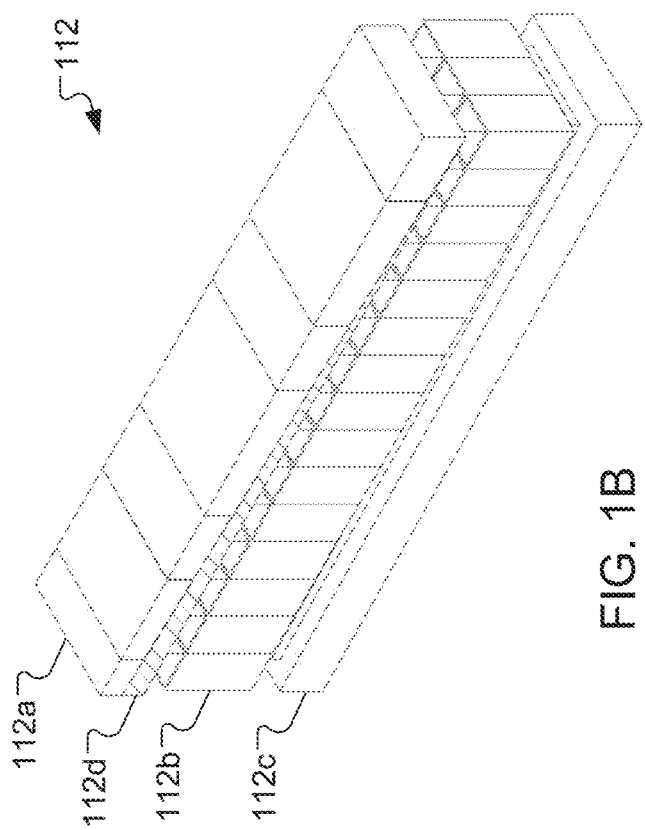
FIG. 1B illustrates a perspective exploded view of a first sensor that may be integrated into the wearable device illustrated in FIG. 1A, according to an embodiment.

FIG. 1B illustrates a side perspective exploded view of the first sensor 112, according to an embodiment. Some of the features in FIG. 1B are the same as or similar to some of the features in FIG. 1A as noted by same reference numbers, unless expressly described otherwise. Additionally, reference may be made to features shown in FIG. 1A and not shown in FIG. 1B. In one embodiment, the first sensor 112 may include a miniaturized spectrometer. The first sensor 112 may include a filter 112a, a collimator 112b, and an optical sensor 112c. In one embodiment, the filter 112a may include an optical filter, such as a variable filter, a linear variable filter, an absorptive filter, a dichroic filter, a monochromatic filter, an infrared filter, an ultraviolet filter, a neutral density filter, a long-pass filter, a band-pass filter, a short-pass filter, a guided-mode resonance filter, a metal mesh filter, a polarizer filter, an arc welding filter, a wedge filter, and so forth. In another embodiment, the filter may include a Fabry-Perot Etalon filter.

The filter 112a may include a linear variable filter. The linear variable filter may allow for selecting which wavelengths strike the optical sensor 112c at a specific position on the optical sensor 112c. This may allow a processor such as the processing unit 110 and/or the processing device 102 to, in turn, distinguish the relative intensities of wavelengths reflected from a tissue to determine which wavelengths are most strongly reflected from the tissue relative to an initial intensity of those wavelengths as emitted from a light source. The processor may determine, based on the reflected wavelengths, one or more parameters, constituents, and/or conditions of the tissue. For example, light having a first wavelength may strike a first region of the optical sensor 112c corresponding to a first region of the filter 112a. The first wavelength may correspond to a constituent of a user's blood. The optical sensor 112c may communicate the intensity of the first wavelength to the processor. The processor may process the first wavelength based on an emitted intensity of the wavelength, an expected attenuation of the wavelength, and/or other attenuation factors to determine an amount of the constituent in the user's blood. Different constituents of the user's blood may transmit and/or reflect wavelengths of light at different intensities. The filter 112a may pass different wavelengths to different positions on the optical sensor 112c. The optical sensor 112c may pass the intensities of the corresponding wavelengths to the processor, and the processor may determine an amount of a blood constituent based on the relative intensities of the wavelengths.

In an embodiment, the filter 112a may include an absorptive filter. The absorptive filter may be formed to have distinct cutoff edges between regions of the absorptive filter corresponding to different wavelength ranges. Furthermore, the absorptive filter may be manufactured of a durable and/or flexible material. In an embodiment, the filter 112a may include a dichroic filter, which may also be referred to as an interference filter. The dichroic filter may be variable. The dichroic filter may allow for very precise selection of wavelengths to be passed through the filter 112a. For example, the dichroic filter may have a transmission profile with a narrow peak, such as a full-width half max (FWHM) wavelength range of 50 nm, 40 nm, 30 nm, 25 nm, 20 nm, 10 nm, 5 nm, and/or 1 nm. The dichroic filter may be implemented in embodiments where the filter 112a is incorporated into a sensor for measuring sensitive phenomena. The sensitive phenomena may include various physiological parameters, conditions, and/or constituents for which small-percentage changes, such as less than or equal to a 50 percent change, results in dramatically different outcomes. For example, the sensitive phenomenon may include a blood acidity level. A healthy blood acidity may include a pH of 7.4. A blood pH less than or equal to 6.8 or greater than or equal to 7.8 may result in irreversible cell damage. In another example, the sensitive phenomenon may include bone density.

In an embodiment, the filter 112a may include a grism. In an embodiment, the filter 112a may include a prism coupled to a diffraction grating. The grism or the coupled prism and diffraction grating may be referred to as the grism. In various embodiments, the prism may include a dispersion prism and/or a prismatic sheet, such as a Fresnel prism. In various embodiments, the diffraction grating may include a ruled grating, a holographic grating, a transmission grating, a reflective grating, a blazed holographic grating, a concave grating, an aberration-corrected concave grating, a constant deviation monochromator concave grating, a Rowland type concave grating, a blazed holographic concave grating, a sinusoidal holographic grating, a sinusoidal ruled grating, a pulse compression grating, and so forth. In an embodiment, the diffraction grating may include a volume phase holographic (VPH) grating. In an embodiment, the diffraction grating may diffract impinging light along one dimension or along two dimensions.

In one embodiment, the collimator 112b may include a device that restricts beam(s) of particles or waves passing into the first sensor 112, such as light in visible and/or non-visible wavelengths, to specific directions of motion, angles, or ranges of angles to become more aligned in a specific direction as the beam(s) travels through the first sensor 112. The collimator 112b may restrict a spatial cross-section of the beam(s). In an embodiment, the collimator 112b may restrict the beam(s) along one dimension and/or along two dimensions.

The collimator 112b may be formed in one or more of a variety of ways. In various embodiments, the collimator 112b may be formed of one or more microtubes. In an embodiment, the collimator 112b may include a plurality of microtubes, where a microtube of the plurality of microtubes is defined by one or more walls encircling a through-channel. A microtube of the plurality of microtubes may have a width ranging from 10 microns to 150 microns, and/or a height ranging from 30 microns to 500 microns. For example, the microtube may have a height equal to less than a thickness of 4 pages of printer paper, and a width equal to less than a thickness of 1 page of printer paper. The microtubes may be prepared separately and joined together, such as by a binder, or the microtubes may be prepared together. For example, the walls of the microtubes may be formed of CNTs. A catalyst layer may be patterned on a substrate forming an impression of the plurality of microtubes, and the CNTs may be grown on the catalyst layer, forming the walls encircling the through-channels to form the microtubes. In another embodiment, the collimator 112b may include a volume of material through which pores and/or apertures are formed. The volume of material may, for example, include a photoresist material. The pores and/or apertures may be etched through the photoresist material, such as by photolithography or plasma etching.

The collimator 112b may be positioned against the filter 112a and/or the optical sensor. For example, the collimator 112b may be disposed between the filter 112a and the optical sensor 112c, or the filter 112a may be disposed between the collimator 112b and the optical sensor 112c. In an embodiment, a wall forming a microtube of the collimator 112b may be aligned normal to a surface of the filter 112a and/or a surface of the optical sensor 112c. In an embodiment, light may pass through the filter 112a and the collimator 112b may allow light within a range of normal incidence passing from the filter 112a to impinge on the optical sensor 112c.

In another embodiment, the collimator 112b may allow light to impinge on the filter 112a within a range of normal incidence. In yet another embodiment, the collimator wall may be aligned at a non-normal angle relative to the surface of the filter 112a and/or the surface of the optical sensor 112c. The angle may correspond to an angle of separated light leaving the filter 112a.

The optical sensor 112c may be operable to convert light rays into electronic signals. For example, the optical sensor 112c may measure a physical quantity of light such as intensity and translate the measurement into a form that is readable by the processor such as an amount of current corresponding directly to the intensity of the light. In an embodiment, the optical sensor 112c may include a semiconductor. The semiconductor may have one or more bandgaps corresponding to a wavelength and/or wavelength range. The semiconductor may be arranged into an array, such as an array of pixels, corresponding to regions of the filter 112a such as the first region 528a, the second region 528b, and so forth. In another example, the optical sensor 112c may include a temperature sensor, a velocity liquid level sensor, a pressure sensor, a displacement (position) sensor, a vibration sensor, a chemical sensor, a force radiation sensor, a pH-value sensor, a strain sensor, an acoustic field sensor, an electric field sensor, a photoconductive sensor, a photodiode sensor, a through-beam sensor, a retro-reflective sensor, a diffuse reflection sensor, and so forth.

The optical sensor 112c may include a segment such as a pixel. In an embodiment, the optical sensor 112c may include a plurality of the segment arrange in an array, such as an array of pixels. The sensor segment may be aligned with a region of the filter 112a. The segment may have an identifier such that the processor may associate the segment with the region of the filter. The identifier may enable the processor to determine a wavelength of light detected by the segment of the optical sensor 112c. For example, in one embodiment, the optical sensor may include a first sensor segment aligned with a first filter region, a second sensor segment aligned with a second filter region, and so forth. The first sensor segment may be identified by the processor as detecting a wavelength and/or range of wavelengths that may correspond to a passband of the first filter region. For example, wavelengths ranging from 400 nm to 449 nm may pass unfiltered through the first filter region. The unfiltered light may strike the first sensor segment, and the first sensor segment may, in response generate an electrical signal that may be transmitted to the processor. The processor may identify the electrical signal as being transmitted by the first sensor segment and may identify that signals transmitted by the first sensor segment may be generated by light having a wavelength ranging from 400 nm to 449 nm.

In one embodiment, the filter 112a, the collimator 112b, and the optical sensor 112c may be stacked together to form the first sensor 112. In one example, the filter 112a, the collimator 112b, and the optical sensor 112c may be integrated together to form an integrated sensor body. In another example, the filter 112a, the collimator 112b, and the optical sensor 112c may be interconnected together. In one example, the filter 112a, the collimator 112b, and the optical sensor 112c may be stacked vertically on top of each other. In another embodiment, the filter 112a may be wedge-shaped where one end of the filter 112a has a relatively thick end that tapers to a thinner edge. In one embodiment, the collimator 112b and the optical sensor 112c may have relatively flat top surfaces and/or bottom surfaces. When the filter is a wedge shape, a filling material 112d may be attached or affixed to the collimator 112b and/or the optical sensor 112c so that the filter 112a may rest or attach flush or level to the collimator 112b and/or the optical sensor 112c. In one example, the filling material 112d may include an optically transparent material (such as clear glass or a clear plastic), an optically translucent material (such as polyurethane, colored or frosted glass, colored or frosted plastic, and so forth), or other material that does not interfere with defined wavelengths of light. In another example, the filling materials 112d may be attached or affixed to the collimator 112b and/or the optical sensor 112c by an adhesive, by welding, by friction, by a pressure fit, and so forth.

FIG. 1C illustrates a perspective view of the second sensor 114, according to an embodiment. Some of the features in FIG. 1C are the same as or similar to some of the features in FIGS. 1A-B as noted by same and/or similar reference characters, unless expressly described otherwise. Additionally, reference may be made to features shown in any of FIGS. 1A-B and not shown in FIG. 1C. The second sensor 114 may include a miniaturized impedance sensor. The miniaturized impedance sensor may include a substrate 114a which may provide structural support for one or more microstructures. The microstructures may include various intermediate layers 114b, a microelectrode 114c, and/or an interstitial filler 114d. In an embodiment, the miniaturized impedance sensor may include the substrate 114a, one or more of the intermediate layers 114b, the microelectrode 114c, and/or the interstitial filler 114d. The miniaturized impedance sensor 400 may include a plurality of microelectrodes 114c.

The substrate 114a may provide a base support structure for deposition, growth, and/or etching of the microstructures. The substrate 114a may provide a support structure for integrating the second sensor 114 into the wearable device 100. In one embodiment, the substrate 114a may include a silicon and/or a tungsten wafer. In another embodiment, the substrate 114a may include glass, such as a glass fiber-reinforced resin. In an embodiment, the substrate 114a may be formed of a flexible material such as polyimide. The substrate 114a may include one or more conductors, such as an electrical trace or a through-surface via. The conductors may electrically couple the microelectrodes 114c to electronics external to the second sensor 114, such as a processor.

The various intermediate layers 114b may include a conductive layer, one or more insulating layers, and/or a catalyst layer. The conductive layer may electrically couple the microelectrode 114c to the substrate 114a conductor. The catalyst layer may catalyze growth of the microelectrode 114c. In an embodiment, the intermediate layers 114b may include one or more ceramic insulating layers, such as alumina, which may be rendered conductive by a preparation process of the miniaturized impedance sensor.

The microelectrode 114c may include a bundle of nanotubes. The bundle may be infiltrated with a bolstering material, where bolster may refer to a property of a material that increases resistance against an applied force of the material and/or another material with which the material is incorporated. Accordingly, the bolstering material may increase the rigidity of the bundle relative to similarly structured bundles not including the bolstering material. The bolstering material may reduce the brittleness of the bundle relative to similarly structured bundles not including the bolstering material. For example, the nanotubes may include Carbon Nanotubes (CNTs) grown on an iron catalyst. The bolstering material may include carbon, a metal, and/or a conductive polymer. In one embodiment, the microelectrode 114c may include CNTs infiltrated with carbon. In another embodiment, the microelectrode 114c may include CNTs infiltrated with a conductive polymer. In another embodiment, the microelectrode 114c may include a polymer coated with a conductive film. The conductive film may include a thin film. The thin film may include metal and/or carbon. In an embodiment, the polymer may be formed into a pillar.

In one embodiment, the interstitial filler 114d may be positioned between rows and/or columns of microstructures on the substrate 114a. The interstitial filler 114d may fill a region between separate microelectrodes 114c. The interstitial filler 114d may include a polymer. In one embodiment the interstitial filler 114d may include a photoresist material. In one embodiment the interstitial filler 114d may include polyimide. In one embodiment, the interstitial filler 114d may include bisphenol A novolac epoxy. The interstitial filler 114d may be deposited on the substrate 114a and/or around the intermediate layers 114b and microelectrodes 114c by sputtering and or spin-coating.

Figures 2A, 2B:
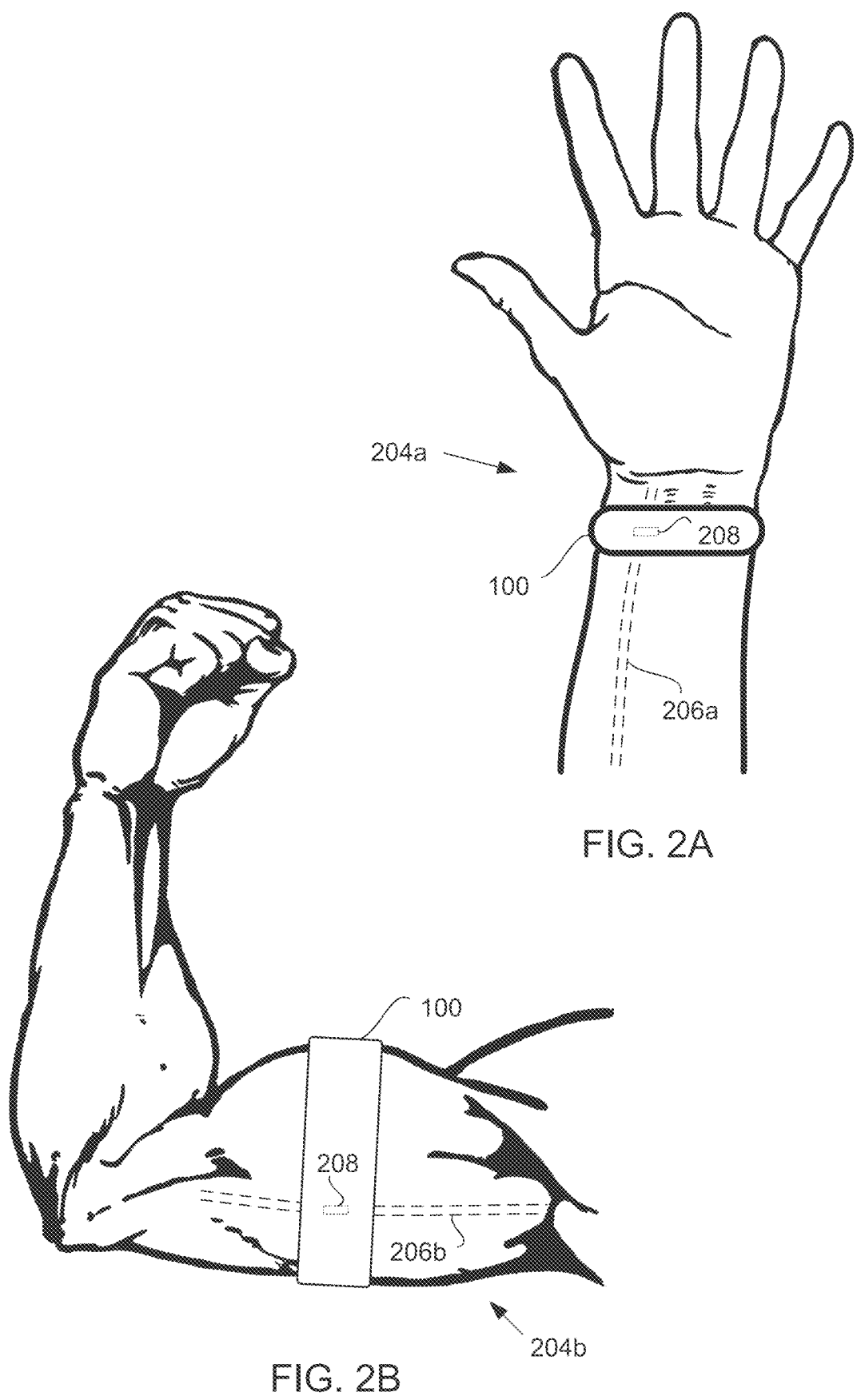
FIG. 2A illustrates the wearable device described and illustrated regarding FIG. 1A on a wrist of a user, according to an embodiment.
FIG. 2B illustrates the wearable device described and illustrated regarding FIG. 1A on an arm of a user, according to an embodiment.

FIG. 2A illustrates the wearable device 100 on a wrist 204a of a user, according to an embodiment. Some of the features in FIG. 2A are the same as or similar to some of the features in FIGS. 1A-C as noted by same and/or similar reference characters, unless expressly described otherwise. Additionally, reference may be made to features shown in any of FIGS. 1A-C and not shown in FIG. 2A. The wrist 204a may include a first muscular-walled tube 206a. The first muscular-walled tube 206a may be, in an embodiment, a vein or an artery. The wearable device 100 may have an integrated biometric sensor 208. The biometric sensor 208 may include the first sensor 112 and/or the second sensor 114. For example, the biometric sensor 208 may include a miniaturized impedance sensor and/or a miniaturized spectrometer.

The wearable device 100 may be positioned on the wrist 204a so that the biometric sensor 208 may be positioned over the first muscular-walled tube 206a. In an embodiment, the first muscular-walled tube 206a may be positioned in the wrist 204a approximate to an underside of the wrist 204a. For example, the first muscular-walled tube 206a may be positioned in the wrist 204a between a dermal layer of the wrist 204a and one or more bones in the wrist 204a. The biometric sensor 208 may be positioned against the underside of the wrist 204a. This may optimize an accuracy and/or precision of a measurement taken by the biometric sensor 208 from the first muscular-walled tube 206a. The wearable device 100 may use the measurements to determine a physiological condition of the user. Positioning the biometric sensor 208 against the underside of the wrist may also reduce a chance of the biometric sensor 208 being struck or otherwise damaged in a way that may affect the accuracy and/or precision of the measurement taken by the biometric sensor 208. For example, an outside of the wrist 204a may be exposed to other surfaces against which the wearable may be struck, whereas an underside of the wrist 204a may be less likely to strike other surfaces because it faces towards a body of the user.

FIG. 2B illustrates the wearable device 100 on an arm 204b of the user, according to an embodiment. Some of the features in FIG. 2B are the same as or similar to some of the features in FIGS. 1A-2A as noted by same and/or similar reference characters, unless expressly described otherwise. Additionally, reference may be made to features shown in any of FIGS. 1A-2A and not shown in FIG. 2B. The arm 204b may include a second muscular-walled tube 206b. The second muscular-walled tube 206b may be, in an embodiment, a vein or an artery. The wearable device 100 may be positioned on the arm 204b so that the biometric sensor 208 may be positioned over the second muscular-walled tube 206b.

In various embodiments, the wearable device 100 may be worn by the user on another body part such as a hand of the user, a forearm of the user, an elbow of the user, a chest of the user, a neck of the user, a head of the user, a torso of the user, a waist of the user, a thigh of the user, a calf of the user, a knee of the user, an ankle of the user, or a foot of the user. Accordingly, the body part may include a muscular-walled tube. The muscular-walled tube may include an ulnar artery, a radial artery, a brachial artery, a basilic vein, a cephalic vein, an axillary artery, an axillary vein, a carotid artery, a jugular vein, an iliac artery, a femoral artery, a femoral vein, a tibial artery, a great saphenous vein, a dorsalis pedis artery, an arch of foot artery, or a temporal artery.

In various embodiments, the biometric sensor 208 may be pressed against a skin surface of the body part. The biometric sensor 208 and/or wearable device 100 may be positioned on the body part over a region of the body part where the muscular-walled tube may be closest to the skin surface for the body part. The biometric sensor 208 may be positioned against the body part where the muscular-walled tube may be positioned between the biometric sensor 208 and a skeletal structure of the body part. This may minimize a distance between the biometric sensor 208 and the muscular-walled tube, which in turn may optimize one or more biometric measurements taken by the biometric sensor 208 from the muscular-walled tube. In various embodiments, the biometric sensor 208 and/or the wearable device 100 may be positioned on the body part over a region of the body part where the skeletal structure is positioned between the skin surface and the muscular-walled tube. This may maximize the distance between the biometric sensor 208 and the muscular-walled tube, which in turn may minimize effects of the muscular-walled tube on measurements taken by the biometric sensor 208. For example, the user may desire to take a measurement of a relatively static physiological condition, physiological parameter, and/or physiological constituent such as a bone density of the user and/or a body fat percentage of the user. The muscular-walled tube may be dynamic and may interfere with measuring the static physiological condition, physiological parameter, and/or physiological constituent. Accordingly, maximizing the distance between the biometric sensor 208 and the muscular-walled tube may result in more accurate and/or precise measurements of the static physiological condition, physiological parameter, and/or physiological constituent. In various embodiments, the biometric sensor 208 and/or the wearable device 100 may be positioned on the body part such that the biometric sensor 208 may be approximate the muscular-walled tube and the skeletal structure such that the muscular-walled tube is not between the skeletal structure and the biometric sensor 208 and the skeletal structure is not between the muscular-walled tube and the biometric sensor 208.

Figure 3A:
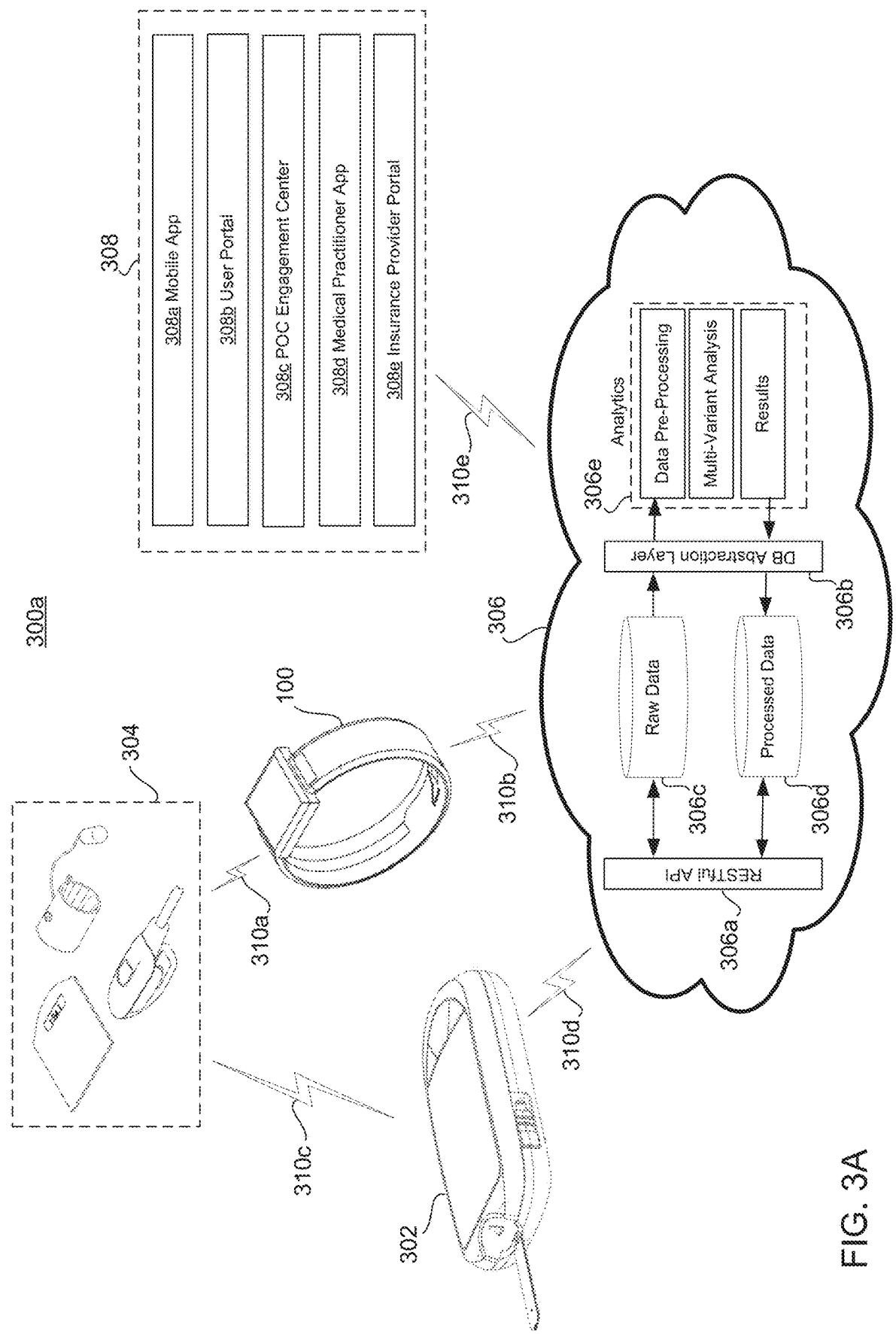
FIG. 3A illustrates a health device network configuration for communicating health data, according to an embodiment.

FIG. 3A illustrates a health device network configuration 300a for communicating health data, according to an embodiment. Some of the features in FIG. 3A are the same as or similar to some of the features in FIGS. 1A-2B as noted by same and/or similar reference characters, unless expressly described otherwise. Additionally, reference may be made to features shown in any of FIGS. 1A-2B and not shown in FIG. 3A. The health device network configuration 300a includes the wearable device 100, an invasive analyte measurement device 302, one or more peripheral measurement devices 304, a cloud-based server 306, and a user device 308. The wearable device 100 and the peripheral measurement device(s) 304 may communicate over a first network communication link 310a. The wearable device 100 and the cloud-based server 306 may communicate over a second network communication link 310b. The invasive analyte measurement device 302 and the peripheral measurement device(s) 304 may communicate over a third network communication link 310c. The invasive analyte measurement device 302 and the cloud-based server 306 may communicate over a fourth network communication link 310d. The cloud-based server 306 and the user device 308 may communicate over a fifth network communication link 310e.

The health device network configuration 300a may include a body area network (BAN), a personal area network (PAN), a near-me area network (NAN), a local area network (LAN), a campus-area network (CAN), a metropolitan area network (MAN), a wide area network (WAN), an internet area network (IAN), and/or a public Internet network. The health device network configuration 300a may include two or more network types. For example, the health device network configuration 300a may include the PAN, the IAN, and the Internet. In another example, the health device network configuration 300a may include the BAN and the IAN. The health device network configuration 300a may include a point-to-point topology, a daisy chain topology, a bus topology, a star topology, a ring topology, and/or a mesh topology. The health device network configuration 300a may include a hybrid topology including two or more types of network topologies. For example, the health device network configuration 300a may include a mesh topology and a star topology. In another example, the health device network configuration 300a may include a point-to-point topology and a star topology.

Campus may refer to a group of rooms adjacent to each other in a building and/or a group of buildings adjacent to each other. Office may refer to a single room within a building, a group of rooms within a building, or a building having one or more rooms. Hospital may refer to a building and/or group of buildings dedicated to providing medical care, including in-patient and/or out-patient care. Home may refer to a user and/or individual's residence. Metropolitan may refer to a geographic region having homes, buildings, offices, and/or campuses. Remote may refer to a device being accessible by another device via a network communication link. Remote may also refer to non-adjacent locations. For example, two non-adjacent rooms within a building may be considered remote from each other, two non-adjacent buildings may be considered remote from each other, two non-adjacent metropolitan areas may be considered remote from each other, and so forth. Local may refer to a device being connected via a closed and/or private network connection to another device. Local may also indicate physical location within a same room, within a same building, on a same campus, and/or in a same metropolitan area, and so forth.

In various embodiments, the health device network configuration 300a may be situated in a single location, such as in a room, in a user's home, within an office building, and/or within a campus. For example, all networked elements of the health device network configuration 300a may be physically located in the same room as each other, in the user's home, within an office building, and/or on the same campus. In various other embodiments, the health device network configuration 300a may be situated across two or more locations, such as across two rooms, between a user's home and an office building, across buildings on different campuses from each other, across different metropolitan areas, and so forth. For example, some of the networked elements of the health device network configuration 300a may be situated in the user's home, and some of the networked elements may be situated in an office building housing a data center in a different city and/or country from the user's home. In another example, some of the networked elements may be situated in a medical office, some of the networked elements may be situated in a data center, and some of the networked elements may be mobile, accompanying the user as the user moves and travels from one location to another.

The network communication links 310a-e may be direct or indirect. A direct link may include a link between two devices where information is communicated from one device to the other without passing through an intermediary. For example, the direct link may include a Bluetooth™ connection, a Zigbee® connection, a Wifi Direct™ connection, a near-field communications (NFC) connection, an infrared connection, a wired universal serial bus (USB) connection, an ethernet cable connection, a fiber-optic connection, a firewire connection, a microwire connection, and so forth. In another example, the direct link may include a cable on a bus network. Direct, when used regarding a network communication link, may refer to any of the aforementioned direct communication links.

An indirect link may include a link between two or more devices where data may pass through an intermediary, such as a router, before being received by an intended recipient of the data. For example, the indirect link may include a wireless fidelity (WiFi) connection where data is passed through a WiFi router, a cellular network connection where data is passed through a cellular network router, a wired network connection where devices are interconnected through hubs and/or routers, and so forth. The cellular network connection may be implemented according to one or more cellular network standards, including the global system for mobile communications (GSM) standard, a code division multiple access (CDMA) standard such as the universal mobile telecommunications standard, an orthogonal frequency division multiple access (OFDMA) standard such as the long term evolution (LTE) standard, and so forth. Indirect, when used regarding a network communication link, may refer to any of the aforementioned indirect communication links.

The invasive analyte measurement device 302 may include a measurement component, a processing component, a communication component, and a user interface. The invasive analyte measurement device 302 may communicate data about an analyte to a user, such as an individual within whom the analyte may be found, or another individual who may use information about the analyte. The analyte may include a physiological element, including bodily fluid, blood, interstitial fluid, blood glucose, platelets, red blood cells, white blood cells, water, sebum, fatty tissue, muscle tissue, bone, nerve tissue, a hormone, glandular fluid, ligament tissue, cartilage, hydration, sodium, potassium, urea, blood alcohol, and so forth.

The measurement component may take a measurement of an analyte of the user invasively. Invasive measurement may include any of a variety of modalities by which the user's skin is punctured and/or the analyte is withdrawn from the user. Invasive measurement may include any of a variety of modalities by which the skin is punctured and/or at least a portion of the measurement device is placed beneath the user's skin. In an embodiment, the measurement component may include a lancing mechanism for puncturing the user's skin, an analyte collection mechanism for collecting body fluid and/or tissue containing the analyte, and a measurement mechanism for measuring the analyte. For example, the lancing mechanism may include a lancet. The analyte collection mechanism may include a test strip onto which a user's blood is placed. The measurement mechanism may include a chemical reactant and electrodes in the test strip. The measurement mechanism may generate electronic signals corresponding to the analyte reacting with the chemical reactant.

The processing component may include various electronics for processing electronic signals generated by the measurement component, the communication component, and/or the user interface. In an embodiment, the processing component may include a processing device and a memory device. The processing device may have non-transitory and/or transitory memory, and the memory device may have non-transitory and/or transitory memory. For example, the processing device may have transitory memory and the memory device may have non-transitory memory. The processing device may generate an output based on an input. For example, the processing device may receive an electronic and/or digital signal from the measurement component. The processing device may send the signal to the memory device, and the memory device may store the signal. The processing device may read the signal and perform one or more tasks with the signal, such as determining an amount of current and/or voltage associated with the signal. The processing device may read from the memory device a quantity of the analyte corresponding with the amount of current and/or voltage. The processing device may transmit a value associated with the quantity of the analyte to the user interface, and the user interface may display the value to the user. In an embodiment, the processing device may transmit data such as the value and/or the amount of the current and/or voltage to the communication component, which may transmit the data to another device.

In various embodiments, the processing component may include a processor, a microprocessor, a computer processing unit (CPU), a graphics processing unit (GPU), a vision processing unit, a tensor processing unit, a neural processing unit, a physics processing unit, a digital signal processor, an image signal processor, a synergistic processing element, a field-programmable gate array (FPGA), a sound chip, a multi-core processor, and so forth. Processor, processing component, processing device, and/or processing unit may refer to any or all of the aforementioned specific devices, elements, and/or features of the processing component.

The communication component may include a networking device such as a networking chip, one or more antennas, and/or one or more communication ports. The networking device may generate radio frequency (RF) signals and transmit the RF signals to one or more of the antennas. The networking device may receive and/or translate the RF signals. The network device may transceive the RF signals. The RF signals may be broadcast and/or received by the antennas. The networking device may generate electronic signals and transmit the RF signals to one or more of the communication ports. The networking device may receive the RF signals from one or more of the communication ports. The electronic signals may be transmitted to and/or from a communication hardline by the communication ports. The networking device may generate optical signals and transmit the optical signals to one or more of the communication ports. The networking device may receive the optical signals and/or may generate one or more digital signals based on the optical signals. The optical signals may be transmitted to and/or received from a communication hardline by the communication port, and/or the optical signals may be transmitted and/or received across open space by the networking device.

In various embodiments, the communication component may include hardware and/or software for generating and communicating signals over a direct and/or indirect network communication link. For example, the communication component may include a USB port and a USB wire, and/or an RF antenna with Bluetooth™ programming and/or instructions installed on a processor, such as the processing component, coupled to the antenna. In another example, the communication component may include an RF antenna and programming and/or instructions installed on a processor, such as the processing component, for communicating over a Wifi and/or cellular network. Communication device and/or communication component may refer to any or all of the aforementioned elements and/or features of the communication component.

The user interface may include hardware and/or software that may communicate information to the user and/or receive input from the user. The user interface may include one or more lights, speakers, displays, buttons, and so forth. In an embodiment, the user interface may include a touchscreen and a graphical user interface (GUI). In an embodiment, the user interface may include a light-emitting diode (LED) display, a liquid crystal display (LCD), an organic LED (OLED) display, an electronic ink (e-Ink) display, and so forth. The user interface may receive inputs from the user which may be transmitted to the processing component. The processing component may generate an output based on the user inputs. For example, the input may include a request for a past measurement stored in the memory device. The processing component may retrieve the past measurement and the user interface may display the past measurement to the user. User interface, display, and/or input device may be used generically herein to refer to any or all of the aforementioned features and/or elements of the user interface.

In one embodiment, the invasive analyte measurement device 302 may include an invasive glucometer. The communication component, the processing component, and the user interface may be integrated into a unit which may include measurement electronics, communication electronics, a processor, memory, and a GUI. The measurement component may include a lancet and a glucose test strip. The user may use the lancet to puncture the user's skin. Blood of the user may be drawn from the punctured skin, and the blood may be placed on the test strip. An end of the test strip may be placed into the electronic unit, and the processor may measure a conductivity of the blood on the strip. The conductivity may indicate an amount of glucose in the user's blood. The amount of glucose may be communicated to the user via the GUI. Data corresponding to the measurement may be communicated over a cellular network to another device such as the cloud-based server 306.

The peripheral measurement device(s) 304 may include any of a variety of devices that may measure a physiological condition, a physiological parameter, a physiological constituent, and/or a physiological element (collectively "physiological characteristic") of the user. Accordingly, the peripheral measurement device(s) 304 may include a weight scale, a blood pressure monitor, a pulse oximeter, a thermometer, a viscosity sensor, an ultrasound machine, a hygrometer, a pulsometer, an echocardiogram machine, an electrodermal activity device, a glucometer, an x-ray machine, and so forth. The peripheral measurement device(s) 304 may take the measurements electronically, mechanically, chemically, or combinations thereof, and so forth. The peripheral measurement device(s) 304 may therefore include electronics, structures, materials, reactants, and so forth, for taking the measurements. Furthermore, one or more of the peripheral measurement device(s) 304 may include electronics for processing and/or communicating the measurements. For example, one or more of the peripheral measurement device(s) 304 may include the processing component and/or the communication component.

A device of the one or more peripheral measurement devices 304 may be configured to communicate data generated and/or collected by the device to the user and/or to another device such as the wearable device 100, the invasive analyte measurement device 302, and/or another of the peripheral measurement device(s) 304. The peripheral measurement device(s) 304 may be networked with the wearable device 100 and/or the invasive analyte measurement device 302 in the BAN, the PAN, the NAN, or the LAN. The first network communication link 310a may include a direct link and/or an indirect link.

In an embodiment, the peripheral measurement device(s) 304, the invasive analyte measurement device 302, and/or the wearable device 100 may be networked in a NAN. The NAN may include overlapping point-to-point topologies. The peripheral measurement device(s) 304 may include a weight scale, a blood pressure monitor, and/or a pulse oximeter. The peripheral measurement device(s) 304, the invasive analyte measurement device 302, and/or the wearable device 100 may include hardware and software for Bluetooth™ communications. The peripheral measurement device(s) 304 may take a measurement from the user. The measurement may correspond to a physiological characteristic. For example, the weight scale may take a measurement corresponding to a weight of the user, the blood pressure monitor may take a measurement corresponding to a blood pressure of the user, and/or the pulse oximeter may take a measurement corresponding to a blood oxygen saturation of the user.

In an embodiment, the measurements may be communicated from the peripheral measurement device(s) 304 to the wearable device 100 over the first network communication link 310a. The first network communication link 310a may include a Bluetooth™ link. The measurements may be raw data. For example, the raw data may include one or more intensities of light detected by the pulse oximeter. In another example, the raw data may include pressure measurements and corresponding sonographic data detected by the blood pressure monitor. In yet another example, the raw data may include strain data from a load cell of the weight scale. The raw data may be processed by the wearable device 100. For example, the processing unit 110 of the wearable device 100 shown in FIG. 1A may receive the wavelength data and/or may output a corresponding blood oxygen saturation. In another example, the processing unit 110 may receive the pressure measurements and corresponding sonographic data and/or may output a corresponding blood pressure. In yet another example, the processing unit 110 may receive the strain data and/or may output a corresponding weight. The display device 104 of the wearable device 100 may display the blood oxygen saturation, the blood pressure, and/or the weight to the user. The processing unit 110 may store the raw data and/or the corresponding physiological measurements.

In an embodiment, the peripheral measurement device(s) 304 may include processors that may process the raw data to output the corresponding physiological characteristics. The peripheral measure devices 304 may store the raw data and/or the corresponding physiological characteristics in local memory, such as in non-transitory and/or transitory memory in the processors. For example, the weight scale may store the strain measurements and/or the corresponding weights in a persistent memory of the weight scale. In another example, the pulse oximeter may store the wavelengths and/or the corresponding blood oxygen saturations in persistent a memory of the pulse oximeter. In yet another example, the blood pressure monitor may store the pressure measurements, the sonographic data, and/or the corresponding blood pressures in a persistent memory of the blood pressure monitor. The peripheral measurement device(s) 304 may communicate the physiological characteristics to the wearable device 100 over the Bluetooth™ link. The wearable device 100 may store the physiological characteristics and/or display the physiological characteristics to the user.

The wearable device 100 may correlate the raw data and/or the physiological characteristics from the peripheral measurement device(s) 304 with raw data and/or physiological characteristics measured by the wearable device 100. In an embodiment, the wearable device 100 may measure a hydration condition of the user and/or correlate the hydration condition to a weight of the user measured by the weight scale. Based on the correlation between the hydration condition and the weight, the wearable device 100 may determine a change in the weight of the user may be due to the user being dehydrated or to the user losing fat. The determination may be communicated to the user via the display device 104. In another embodiment, the wearable device 100 may determine a blood glucose level of the user and/or correlate the blood glucose level of the user with a blood pressure of the user. The wearable device 100 may determine that an increase in the blood pressure of the user corresponds to a subsequent sharp increase in the blood glucose level of the user. The wearable device 100 may determine based on the correlation that the user eats when the user experiences stress. The determination may be communicated to the user via the display device 104.

The raw data and/or the physiological characteristics measured by the peripheral measurement device(s) 304 may be communicated to the invasive analyte measurement device 302 over the third network communication link 310c. The third network communication link 310c may include a Bluetooth™ link. The invasive analyte measurement device 302 may receive the raw data. The processing component of the invasive analyte measurement device 302 may process the raw data and/or output the corresponding physiological characteristic. The invasive analyte measurement device 302 may display the physiological characteristic to the user. In an embodiment, the peripheral measurement device(s) 304 may process the raw data and/or output the corresponding physiological characteristics. The peripheral measurement device(s) 304 may store the raw data and/or the physiological characteristics in non-transitory and/or transitory memory. The raw data and/or the physiological characteristics may be communicated to the invasive analyte measurement device 302. The invasive analyte measurement device 302 may store the raw data and/or the physiological characteristics. The invasive analyte measurement device 302 may display the physiological characteristics to the user.

The invasive analyte measurement device 302 may correlate the raw data and/or the physiological characteristics from the peripheral measurement device(s) 304 with raw data and/or physiological characteristics measured by the wearable device 100. In an embodiment, the invasive analyte measurement device 302 may determine a blood glucose level of the user and/or correlate the blood glucose level of the user with a blood pressure of the user measured by the blood pressure monitor. The invasive analyte measurement device 302 may determine that a sharp decrease in the blood pressure of the user follows a sharp increase in the blood glucose level of the user. The invasive analyte measurement device 302 may determine based on the correlation that the user is experiencing a hyperglycemic event. The determination may be communicated to the user via the invasive analyte measurement device 302 user interface, along with a recommendation of how to resolve the hyperglycemic event, such as by recommending the user take a shot of insulin. In another embodiment, the invasive analyte measurement device 302 may correlate the blood glucose level of the user with a blood oxygen saturation of the user measured by the pulse oximeter. The correlation may be communicated to a remote server such as the cloud-based server 306 for comparison with a blood glucose measurement taken by the wearable device 100. The cloud-based server 306 may compare the two blood glucose measurements and the blood oxygen saturation measurement to determine a component of the measurement taken by the wearable device 100 which may be attributable to blood oxygen.

In an embodiment, the peripheral measurement device 304 may be configured, i.e. programmed, to select whether to transmit a physiological characteristic measurement to the invasive analyte measurement device 302 and/or the wearable device 100 based on one or more device status characteristics. The device status characteristics may include a remaining battery life, a power output of the device, a strength of a signal between the device and the cloud-based server 306, a strength of a signal between the device and the peripheral measurement device 304, whether the device is networked to the peripheral measurement device 304, and/or a physical proximity of the device to the peripheral measurement device. For example, the peripheral measurement device 304 may select the device which has the greatest remaining battery life, has the greatest power output, has the greatest signal strength with the cloud-based server and/or the peripheral measurement device, is networked to the peripheral measurement device, and/or has a nearest physical proximity to the peripheral measurement device.

The cloud-based server 306 may include a physical server and/or a virtual server. For example, the cloud-based server 306 may include one or more bare-metal servers. The bare-metal servers may be single-tenant servers or multiple tenant servers. In another example, the cloud-based server 306 may include a bare metal server partitioned into two or more virtual servers. The virtual servers may include separate operating systems and/or applications from each other. In yet another example, the cloud-based server 306 may include a virtual server distributed on a cluster of networked physical servers. The virtual servers may include an operating system and/or one or more applications installed on the virtual server and distributed across the cluster of networked physical servers. In yet another embodiment, the cloud-based server 306 may include more than one virtual server distributed across the cluster of networked physical servers.

The cloud-based server 306 may include a processing component and/or a communication component. The processing component may include a processing device and/or a memory device. One or more applications may be stored in the memory device and/or executed by the processing device. For example, one or more application programming interfaces (APIs) may be installed on and/or executed by the cloud-based server 306. In another example, one or more database applications may be installed on and/or executed by the cloud-based server 306. In yet another example, one or more data analytics applications may be installed on and/or executed by the cloud-based server 306. The communication component may include hardware and/or software enabling the cloud-based server 306 to communicate with other devices. The hardware may include one or more antennas and/or hardwire communication ports. The software may include programming and/or instructions which, when executed, may generate signals which may be communicated from the cloud-based server via the antennas and/or hardwire communication ports. In one embodiment, the cloud-based server 306 may communicate wirelessly via Wifi and/or over hardwire via one or more ethernet cables. In various embodiments, software, APIs, and/or applications run on and/or installed on the cloud-based server 306 may be hidden from other devices networked to the cloud-based server 306.

In an embodiment, the APIs may include a representational state transfer (RESTful) API configuration 306a. The RESTful API 306a may enable data calls to the cloud-based server 306 from a variety of devices and/or applications having different hardware and/or software architectures. The APIs may further include a database abstraction layer 306b. The database applications may include a raw data database 306c and/or a processed data database 306d. The cloud-based server 306 may include a data analytics application 306e. The data analytics application 306e may include, for example, a data pre-processing component, a multi-variant analysis component, and/or a results component. The data analytics application 306e may generate a predictive model, may identify correlations between data, may integrate measurement data from two or more measurement devices, and so forth. In an embodiment, the predictive model may correlate invasive glucose measurements to non-invasive glucose measurements to identify one or more trends in the invasive glucose measurements and/or the non-invasive glucose measurements.

In an embodiment, the RESTful API 306a may convert data communicated to the cloud-based server 306 from a format corresponding to a device from which the data was communicated into a format in which the data may be stored on and/or processed by the cloud-based server 306. The communicated data may be stored in the raw data database 306c. The data analytics application 306e may request the communicated data. The communicated data may be passed to the database abstraction layer 306b. The database abstraction layer 306b may convert the communicated data into a format that may be read and/or manipulated by the data analytics application 306e. The data analytics application 306e may process the communicated data and/or output resulting data. The resulting data may be passed to the processed data database 306d. The database abstraction layer 306b may convert the resulting data to a format in which the data may be stored in the processed data database 306d. The resulting data may be converted by the RESTful API 306a to a format corresponding to another device. The other device may request the resulting data and/or the cloud-based server 306 may include instructions to communicate the resulting data. For example, the cloud-based server 306 may include instructions to communicate the resulting data to the other device automatically once the resulting data has been output by the data analytics application 306e.

In another embodiment, processed data may be communicated to the cloud-based server 306. The processed data may be converted by the RESTful API 306a and/or stored in the processed data database 306d. The processed data may be communicated from the cloud-based server 306 to the other device. The processed data may be requested by the other device, and/or the cloud-based server 306 may store instructions to automatically communicate the data to the other device. In yet another embodiment, raw data stored in the cloud-based server 306 may be communicated to the other device. The other device may request the raw data, and/or the cloud-based server 306 may store instructions to automatically communicate the raw data to the other device.

The cloud-based server 306 may be physically located near the wearable device 100, the invasive analyte measurement device 302, and/or the peripheral measurement device(s) 304. For example, the cloud-based server 306 may be located in the same room, in the same building, and/or on the same campus as the wearable device 100, the invasive analyte measurement device 302, and/or the peripheral measurement device(s) 304. In an embodiment, the cloud-based server 306, the wearable device 100, the invasive analyte measurement device 302, and/or the peripheral measurement device(s) 304 may be located on a health care campus. In another embodiment, the cloud-based server 306, the wearable device 100, the invasive analyte measurement device 302, and/or the peripheral measurement device(s) 304 may be located in a hospital.

The cloud-based server 306 may be physically located remotely from the wearable device 100, the invasive analyte measurement device 302, and/or the peripheral measurement device(s) 304. For example, the cloud-based server 306 may be located in a different building, on a different campus, in a different metropolitan area, in a different country, and/or on a different continent as the wearable device 100, the invasive analyte measurement device 302, and/or the peripheral measurement device(s) 304. In another example, the cloud-based server may be located in a data center. In yet another example, the cloud-based server 306 may be distributed across two or more locations remote from each other and/or located remotely from the wearable device 100, the invasive analyte measurement device 302, and/or the peripheral measurement device(s) 304. In an embodiment, the wearable device 100, the invasive analyte measurement device 302, and/or the peripheral measurement device(s) 304 may be located at the user's home and the cloud-based server 306 may be located in a different city than the user's home. In another embodiment, the wearable device 100, the invasive analyte measurement device 302, and/or the peripheral measurement device(s) 304 may be located in a medical office and the cloud-based server 306 may be located in a different building complex than the medical office.

The cloud-based server 306, the wearable device 100, the invasive analyte measurement device 302, and/or the peripheral measurement device(s) 304 may be configured together in one or more network topologies. For example, the network may include a ring-type topology, a star topology, and/or a tree topology. In an embodiment where the network is configured in a ring-type topology, data may pass freely back and forth between one of the peripheral measurement device(s) 304 and the wearable device 100, data may pass freely back and forth between the peripheral measurement device and the invasive analyte measurement device 302, data may pass freely back and forth between the cloud-based server 306 and the wearable device 100, and/or data may pass freely back and forth between the cloud-based server 306 and the invasive analyte measurement device 302. Data may not pass between the wearable device 100 and the invasive analyte measurement device 302 through the peripheral measurement device. In an embodiment where the network is configured in a tree topology, data may flow from the peripheral measurement device(s) 304 through the wearable device 100 to the cloud-based server 306, and/or from the invasive analyte measurement device 302 to the cloud-based server 306.

In embodiments where the cloud-based server 306, the wearable device 100, the invasive analyte measurement device 302, and/or the peripheral measurement device(s) 304 may be physically located near each other, the network may include a NAN, a LAN, and/or a CAN. In some embodiments where the cloud-based server 306, the wearable device 100, the invasive analyte measurement device 302, and/or the peripheral measurement device(s) 304 may be physically located near each other, the network may include a MAN, a WAN, an IAN, and/or the Internet. In embodiments where the cloud-based server 306 may be located remotely from the wearable device 100, the invasive analyte measurement device 302, and/or the peripheral measurement device(s) 304, the network may include a MAN, a WAN, an IAN, and/or the Internet. The wearable device 100, the invasive analyte measurement device 302, and/or the peripheral measurement device(s) 304 may be networked together in a BAN, PAN, NAN, LAN, and/or CAN, and/or the cloud-based server 306 may be networked together with the wearable device 100 and/or the invasive analyte measurement device 302 in a MAN, a WAN, an IAN, and/or over the Internet.

Measurement data such as the raw data and/or the physiological characteristics collected, processed, and/or output by the peripheral measurement device(s) 304 and/or the wearable device 100 may be communicated to the cloud-based server 306 over the second network communication link 310b. Measurement data such as the raw data and/or the physiological characteristics collected, processed, and/or output by the peripheral measurement device(s) 304 and/or the invasive analyte measurement device 302 may be communicated to the cloud-based server 306 over the fourth network communication link 310d. The second network communication link 310b and/or the fourth network communication link 310d may include a direct link and/or an indirect link. For example, the second network communication link 310b and/or the fourth network communication link 310d may include a Bluetooth™ connection, a Wifi connection, a USB connection, an ethernet connection, a cellular network connection, and/or generally an Internet connection.

The user device 308 may include a processing component, a communication component, and/or a user interface. The processing component may include a processing device and/or a memory device. The communication component may include hardware and/or software which may be configured to communicate data with another device, such as the cloud-based server 306, another user device, the invasive analyte measurement device 302, the wearable device 100, the peripheral measurement device(s) 304, and so forth. The user interface may include a screen, buttons, a microphone, a speaker, and/or a touchscreen. The user interface may communicate information to the user, such as by displaying information or playing sounds, and/or may receive input from the user. In various embodiments, the user device 308 may include a personal computer, a mobile device such as a mobile phone, a personal digital assistant, a tablet computer, an artificial intelligence telephony system, an interactive voice recognition system, and so forth.

The user device 308 may include an application that may communicate health information with the user. The health information may be health information of a patient. The user may include the patient, a health care provider such as a nurse, doctor, and/or physician's assistant, a health care insurer, a third party authorized by the patient to access the patient's health information such as an individual with power of attorney for the patient, a healthcare partner of the patient, and so forth. In an example, the healthcare partner may include a third party who reviews the patient's healthcare information and/or communicates with the patient about the patient's health. The healthcare partner may include an employee of a healthcare customer service center such as a call center.

The health information application may be tailored to provide specific information for a specific user. Accordingly, the health information application may include information relevant to the user and may exclude information irrelevant to the user. The user may interface with the application via the user device 308. The health information application may enable the user device 308 to display the health information to the user, and/or the health information application may enable the user to input the health information into the user device 308, such as via the user interface. The health information application may include software that may cause the processor to render an output based on an input. The software may provide instructions for rendering the output based on the input. The health information application may be installed on the user device 308 and/or the application may be installed on a device physically remote from the user device 308. For example, the application may be installed on a server and/or may be accessed via a network from the user device 308 by a web browser installed on the user device 308. In various embodiments, the application may include a mobile application 308a, a user portal 308b, a point-of-care engagement center application 308c, a medical practitioner application 308d, and/or an insurance provider portal 308e.

The health information application may be tailored to provide specific information which may depend on the type of device through which the health information may be communicated. The device type may include features such as how information is provided to the user and/or how information is input into the device by the user and/or another device. The tailoring may be the same for different devices, or the tailoring may be different for different devices. For example, information displayed on a mobile device such as a mobile phone and/or tablet may be different than information displayed on a personal computer. Information displayed on a mobile phone may be different than information displayed on a tablet. In an embodiment, information displayed by the personal computer may include detailed historical information about the patient, such as past medical charts, names of providers, dynamic graphs of physiological characteristics, live vitals, current and/or past diagnoses, detailed demographic data, and so forth. Information displayed by the mobile device may include current vitals, goals and/or tracking of progress towards those goals, upcoming appointments, messages, and so forth.

In one embodiment, information displayed on the non-invasive analyte measurement device such as the wearable device 100 may include information such as: an amount of time the patient's analyte level is within a range; where a current analyte measurement falls relative to one or more measurement zones such as a standard of deviation, a coefficient of variation, and so forth; a trend in the patient's analyte measurements; a number of step counts of the patient; a current blood oxygenation level of the patient; and so forth. In one embodiment, information displayed on the invasive analyte measurement device 302 may include the information described above regarding the non-invasive analyte measurement device and: a most-recent invasive analyte measurement; trends in the invasive and/or non-invasive analyte measurements; user profile information; a history and/or logbook of analyte measurements correlated with events and/or activities that may impact the analyte measurements; and so forth. In an embodiment, information displayed on a mobile phone in an application specific to the health device network may cumulatively include the information displayed on the non-invasive analyte measurement device and the invasive analyte measurement device, and: a rewards system; more-detailed trending data such as an ability to select different time frames and/or comorbidities, and so forth; means for contacting a point-of-care engagement center, a healthcare provider, and/or another individual; and so forth. In an embodiment, information displayed via a web portal specific to the health device network may cumulatively include the information displayed on the non-invasive analyte measurement device, the invasive analyte measurement device, and the mobile phone, and: a messaging system; an interface to activate and/or connect measurement and/or display devices; more detailed health information of the patient; an interface to redeem rewards earned by the patient; an interface to set goals; an entire history of analyte measurements; and so forth.

The format and/or programming of the application may correspond to the device type, or the format and/or programming of the application may be independent of the device type. For example, the application may be formatted to be installed on a mobile device, the application may be formatted to be installed on a server such as a local server and/or a web server, the application may be formatted to be installed on a personal computer, and so forth. The application may be formatted to be displayed by a web browser and/or may dynamically change the type and/or format of the information displayed based on whether the web browser is operating on a personal computer, a virtual computer, a mobile device, and so forth. In an embodiment, the application may allow the user to choose how and/or what type of information is displayed to the user without regard to the type of device and/or the format of the application.

The health information application may be tailored to provide specific information that may correspond to the format and/or programming of the application. The tailoring may be the same for different application types, or the tailoring may be different for different application types. For example, health information about the patient provided via the mobile application 308a may be different than health information about the patient provided via the user portal 308b, the point of care engagement center application 308c, the medical practitioner application 308d, and/or the insurance provider portal 308e. Health information about the patient provided via the user portal 308b may be different than health information about the patient provided through the mobile application 308a, the point of care engagement center application 308c, the medical practitioner application 308d, and/or the insurance provider portal 308e. Health information about the patient provided via the point of care engagement center application 308c may be different than health information about the patient provided via the mobile application 308a, the user portal 308b, the medical practitioner application 308d, and/or the insurance provider portal 308e. Health information about the patient provided via the medical practitioner application 308d may be different than health information about the patient provided via the mobile application 308a, the user portal 308b, the point of care engagement center application 308c, and/or the insurance provider portal 308e. Health information about the patient provided via the insurance provider portal 308e may be different than health information about the patient provided via the mobile application 308a, the user portal 308b, the point of care engagement center application 308c, and/or the medical practitioner application 308d.

In an embodiment, input accepted via the application may be tailored based on the device type, the format and/or programming of the application, and/or the user. For example, the application may display the patient's medical chart to the patient via the user portal 308b and/or the user portal 308a may prevent the patient from editing the medical chart information. Continuing the example, the application may display the patient's medical chart to a healthcare provider via the mobile application 308a and/or the mobile application 308a may accept input from the healthcare provider which may add information to the patient's medical chart and/or change information in the patient's medical chart. In another example, the application may display health goals of the patient to the patient via mobile application 308a and/or may accept input from the patient via the mobile application 308a such as adding new goals and/or recording progress towards the goals, and so forth. Continuing the example, the application may display the patient's goals and/or progress towards the goals to a third party such as a family member of the patient via the mobile application 308a. The mobile application 308a may prevent the family member from editing the goals and/or adding progress to the goals.

The fifth network communication link 310e may enable and/or facilitate transmission of data between the cloud-based server 306 and the user device 308. The fifth network communication link 310e may be part of a LAN, CAN, MAN, WAN, IAN, and/or the internet. In various embodiments, the fifth network communication link 310e may include two or more forms of signal transmission and/or one or more intermediary devices. For example, the fifth network communication link 310e may include a hardlines, a network router, and/or a network switch between the cloud-based server 306 and a cellular network switch. The fifth network communication link 310e may further include a hardline between the cellular network switch and a cellular tower. The fifth network communication link 310e may further include a wireless link between the cellular tower and the user device 308. In another example, the fifth network communication link 310e may include a hardline connected to the cloud-based server 306 and a network switch, and a hardline connected to the network switch and the user device 308.

In various embodiments, the fifth network communication link 310e may include a direct link between the user device 308 and the cloud-based server 306. For example, the cloud-based server 306 and the user device 308 may be part of a LAN, and the cloud-based server 306 may be networked to the internet. The cloud-based server 306 may include a virtual server installed on a bare-metal server. The bare metal server may be located in an office with the user device 308. The user device 308 may be connected to the bare metal server by a hardline connection such as an ethernet cable. The bare metal server may be connected to the internet wirelessly and/or via a hardline connection.

The elements of the health device network configuration 300a, including the devices, the server, and/or the network communication links, may form an independent and/or isolated network. The independent and/or isolated network may include a LAN, CAN, MAN, IAN, and/or WAN. The health device network configuration 300a may be physically isolated from devices outside the health device network configuration 300a. For example, wireless and/or hardline connections may be limited to in-network devices. The health device network configuration 300a may be virtually isolated from devices outside the health device network configuration 300a. For example, wireless and/or hardline connections may extend to out-of-network devices, but communication with in-network devices by out-of-network devices may be restricted by a firewall, a paywall, network authentication, encryption, and so forth.

Within the health device network configuration 300a, devices may communicate in one or more of a variety of ways. In one embodiment, measurement data may be passed from one or more of the peripheral measurement device(s) 304 to the wearable device 100 over the first network communication link 310a. The wearable device 100 may combine the measurement data from the peripheral device with measurement data collected from the user by the wearable device 100, such as by the first sensor 112 and/or the second sensor 114. The combined measurement data may be communicated to the cloud-based server 306 over the second network communication link 310b and/or stored in the raw data database 306c. The raw combined measurement data may be processed by the data analytics application 306e and/or stored in the processed data database 306d. The user may request the processed combined measurement data through the mobile application 308a installed on the user device 308, which may include a mobile phone. The processed combined measurement data may be transmitted to the mobile phone over the fifth network communication link 310e and/or may be displayed to the user via the mobile application 308a.

In another embodiment, measurement data may be passed from one or more of the peripheral measurement device(s) 304 to the invasive analyte measurement device 302 over the third network communication link 310c. The user may input instructions into the invasive analyte measurement device 302 that the measurement data is to be processed by the cloud-based server 306. The instructions may include instructions to push a notification to the user device 308, which may include a personal computer, that the measurement data is available for access by the user device 308. The measurement data may be transmitted to the cloud-based server 306 over the fourth network communication link 310d. The cloud-based server 306 may store and/or process the measurement data. The cloud-based server 306 may transmit the notification to the user device 308 over the fifth network communication link 310e. The notification may be communicated to a user of the personal computer through the user portal 308b. The user of the personal computer may request the measurement data in raw and/or processed form through the user portal 308b. The cloud-based server 306 may transmit the measurement data to the personal computer over the fifth network communication link 310e. The user of the personal computer may view and/or manipulate the measurement data through the user portal 308b.

In yet another embodiment, the wearable device 100 and the invasive analyte measurement device 302 may take separate measurements approximately concurrently, where approximately concurrent may refer to measurements taken simultaneously and/or within a time period of each other, the time period less than a time period of change for a respective analyte. For example, the analyte may be glucose and approximately concurrent may refer to measurements taken within 1-5 minutes of each other. The measurement by the wearable device 100 may be communicated to the cloud-based server 306 over the second network communication link 310b. The wearable device 100 measurement may include a series of continuous, time-indexed blood glucose measurements. The measurement by the invasive analyte measurement device 302 may be communicated to the cloud-based server 306 over the fourth network communication link 310d. The invasive analyte measurement may include a time-indexed blood glucose measurement. The data analytics application 306e may correlate the time-indexed invasive blood glucose measurement with at least one of the series of continuous, time-indexed blood glucose measurements from the wearable device 100. The correlation may include a time correlation, where the two measurements have the same time index. The cloud-based server 306 may communicate the correlation to the wearable device over the second network communication link 310b. The cloud-based server 306 may communicate the correlation to the invasive analyte measurement device 302 over the fourth network communication link 310d. The cloud-based server 306 may communicate the correlation to the user device 308 over the fifth network communication link 310e.

The wearable device 100, the invasive analyte measurement device 302, the peripheral measurement device(s) 304, the cloud-based server 306, and/or the user device 308 may be physically located near each other. For example, the user device 308, the wearable device 100, the invasive analyte measurement device 302, the peripheral measurement device(s) 304, and/or the cloud-based server 306 may be located in the same room, in the same building, and/or on the same campus. In an embodiment, the user device 308, the wearable device 100, the invasive analyte measurement device 302, the peripheral measurement device(s) 304, and/or the cloud-based server 306 may be located on the same health care campus. In another embodiment, the user device 308, the wearable device 100, the invasive analyte measurement device 302, the peripheral measurement device(s) 304, and/or the cloud-based server 306 may be located in the same hospital.

The user device 308, the cloud-based server 306 the wearable device 100, the invasive analyte measurement device 302, and/or the peripheral measurement device(s) 304 may be physically located remotely from each other. For example, the user device 308, the cloud-based server 306, the wearable device 100, the invasive analyte measurement device 302, and/or the peripheral measurement device(s) 304 may be located in a different building, on a different campus, in a different metropolitan area, in a different country, and/or on a different continent from each other. In an embodiment, the wearable device 100, the invasive analyte measurement device 302, and/or the peripheral measurement device(s) 304 may be located at the user's home, the cloud-based server 306 may be located in a different city than the user's home, and the user device 308 may be located in a different city than the cloud-based server 306 and/or in a different city than the user's home. For example, the cloud-based server 306 may be physically located in a data center and the user device 308 may be located in a call center. In another embodiment, the peripheral measurement device(s) 304 may be located in a medical office and the wearable device 100 may be worn by the user and/or may accompany the user as the user travels from one location to another. The user may carry the invasive analyte measurement device 302 with the user, may leave the invasive analyte measurement device 302 at the user's home, and so forth. The cloud-based server 306 may be located in a data center and the user device 308 may be located in a call center.

The health device network configuration 300a may allow a user to aggregate data from a plurality of different measurement devices to perform data analysis. The aggregated data may provide health insights that separate measurements alone may not provide. For example, correlations between changes in blood glucose levels and changes in blood oxygen saturation may provide insights into treatment strategies for individuals with diabetes. Passing data from multiple devices through one device to the cloud-based server 306 may provide data integrity to ensure measurements are captured. For example, if each individual device communicates separately and directly with the cloud-based server 306, connectivity interruptions may not be caught and may result in missing data. However, if data is routed through one device, connectivity can be more easily monitored and repaired if there are issues, ensuring that more data is captured. Additionally, it may be more efficient to send data from multiple devices in a single data packet to prevent data loss due to data traffic congestion at the cloud-based server 306.

In an embodiment, wherein the wearable device 100 (i.e. a non-invasive glucometer) and/or the invasive analyte measurement device 302 may aggregate an invasive glucose measurement and a non-invasive glucose measurement into a data batch. The data analytics application 306e may: integrate the invasive glucose measurement and the non-invasive glucose measurement; identify correlation between the invasive glucose measurement and the non-invasive glucose measurement; or generate a predictive model based on the invasive glucose measurement and the non-invasive glucose measurement. The predictive model may predict corrections to the non-invasive glucose measurement based on the invasive glucose measurement. The user device may display to the user the invasive glucose measurement, the non-invasive glucose measurement, the data batch, and/or the processed data.

In an embodiment, the invasive analyte measurement device 302 or the wearable device may aggregate a physiological characteristic measurement by one or more of the peripheral measurement devices 304 with the invasive glucose measurement and the non-invasive glucose measurement in the data batch. The data analytics application 306e may be configured to: integrate the physiological characteristic measurement with the invasive glucose measurement and the non-invasive glucose measurement; identify a correlation between the physiological characteristic measurement, the invasive glucose measurement, and the non-invasive glucose measurement; and/or generate the predictive model based on the physiological characteristic measurement, the invasive glucose measurement, and/or the non-invasive glucose measurement.

In an embodiment, the processing component of the user device 308 or the data analytics application 306e may be configured to: identify a critical health event; and/or generate a request for a confirming measurement that confirms the critical health event. The critical health event may include the subject experiencing adverse symptoms. The critical health event may be identified based on: the invasive glucose measurement; the non-invasive glucose measurement; and/or the physiological characteristic measurement. The confirming measurement from may be taken from: the wearable device 100 and/or one or more of the peripheral measurement devices 304 if the critical health event is identified based on the invasive glucose measurement; the invasive analyte measurement device 302 and/or one or more of the peripheral measurement devices 304 if the critical health event is identified based on the non-invasive glucose measurement; and/or the invasive analyte measurement device 302 and/or the wearable device 100 if the critical health event is identified based on the physiological characteristic measurement.

In an embodiment, one or more of the peripheral measurement devices 304 may be configured to select whether to transmit the physiological characteristic measurement to the invasive analyte measurement device 302 or the wearable device 100 based on whichever glucometer: has a greatest battery life remaining; has a greatest power output; has a greatest signal strength with the cloud-based server 306 or the peripheral measurement device 304; is networked to the peripheral measurement device 304; and/or has a nearest physical proximity to the peripheral measurement device 304.

In an embodiment, the data analytics application 306e may be configured to: identify a critical health event based on the data batch; and communicate an alert to the invasive analyte measurement device 302, the wearable device 100, or the user device 308. The invasive analyte measurement device 302 and/or the wearable device 100 may communicate the alert to the subject. The user device 308 may communicate the alert to the user via the mobile application 308a, the user portal 308b, the point-of-care engagement center application 308c, the medical practitioner application 308d, and/or the insurance provider portal 308e.

In an embodiment, the raw data database 306c may store a plurality of the data batch having a plurality of the invasive glucose measurement and a plurality of the non-invasive glucose measurement. The plurality of the data batch may include a first sampling rate corresponding to the plurality of the invasive glucose measurement and a second sampling rate corresponding to the plurality of the non-invasive glucose measurement. The data analytics application 306e may be configured to determine whether the first sampling rate or the second sampling rate allows for smooth processed data to be output by the data analytics application 306e. The smooth processed data may include and/or be characterized by data from which periods of fasting can be distinguished from periods of eating. The cloud-based server 306 may be configured to automatically adjust the first sampling rate of the invasive analyte measurement device 302 or the second sampling rate of the wearable device 100 upon determining the first sampling rate or the second sampling rate is too low to distinguish the periods of fasting from the periods of eating.

In an embodiment, the data analytics application 306e may be configured to: identify a critical health event based on the non-invasive glucose measurement; and prompt the subject to take a check measurement using the invasive analyte measurement device 302. The prompting may be directed to: the subject via the invasive analyte measurement device 302; the subject via the wearable device 100; or the user via the user device 308.

In an embodiment, the invasive glucose measurement may include: a first value indicating a first electronic signal; and/or a first device tag correlating the first value with the invasive analyte measurement device 302. The non-invasive glucose measurement may include: a second value indicating a second electronic signal; and/or a second device tag correlating the second value with the wearable device 100. The data analytics application 306e may be hidden from the invasive analyte measurement device 302 and the wearable device 100; The data analytics application 306e may be configured to translate the first value to a first glucose level and the second value to a second glucose level.

In an embodiment, the processing component of the user device 308 may be configured to transmit a request for: the invasive glucose measurement from the invasive analyte measurement device 302 via the cloud-based server 306; and/or the non-invasive glucose measurement from the wearable device 100 via the cloud-based server 306. The user device 308 may further be configured to: receive the invasive glucose measurement and the non-invasive glucose measurement independent of the data batch via the cloud-based server 306; and/or generate an overlaid display of the invasive glucose measurement and the non-invasive glucose measurement.

In an embodiment, the processing component of the user device 308 may be configured to: obtain and store information regarding a first configuration of the invasive analyte measurement device 302 or the wearable device 100; identify a new configuration of the invasive analyte measurement device 302 or the wearable device based on a data request received by the user device 308; and/or transmit executable instructions to the invasive analyte measurement device 302 or the wearable device 100 via the cloud-based server 306 to update the first configuration to the new configuration. The data request may be input into the user device 308 by the user or communicated from the cloud-based server 306. The new configuration may change a sensitivity or sampling rate of the invasive analyte measurement device 302 or the wearable device.

In an embodiment, non-invasive analyte measurements may be taken by a desktop measurement device. The desktop measurement device may include: a housing ergonomically shaped to match a shape of a resting hand; a finger clasp coupled to the housing, the finger clasp comprising: a light source positioned in the finger clasp to emit light through a fingertip of the subject as the finger is inserted into the finger clasp; a miniaturized spectrometer positioned in the finger clasp to receive the light through the finger as the finger is inserted into the finger clasp; and a miniaturized impedance sensor positioned in the finger clasp to press against skin of the finger as the finger is inserted into the finger clasp.

In an embodiment, the invasive analyte measurement device 302 may include: measurement electronics configured to measure an amount of glucose in a blood sample on a test strip; a user interface; a communication component communicatively coupled to the cloud-based server 306 and directly communicatively coupled to a non-invasive glucometer such as the wearable device 100; and/or a processing component. The processing component may be configured to: take a first glucose measurement by the measurement electronics; receive a second glucose measurement directly from the non-invasive glucometer, the first glucose measurement and the second glucose measurement taken approximately concurrently; receive a set of subsequent glucose measurements from the non-invasive glucometer, the set subsequent to the second glucose measurement; aggregate into a data batch the first glucose measurement, the second glucose measurement, and the set of subsequent glucose measurements; send the data batch to the cloud-based server 306; and/or receive predictive analytics based on the data batch from the cloud-based server 306.

In an embodiment, the processing component of the invasive analyte measurement device 302 may be configured to: receive a physiological measurement from one or more of the peripheral measurement devices 304, the physiological measurement taken approximately concurrently with the first glucose measurement or approximately concurrently with one subsequent glucose measurement; and aggregate into the data batch the physiological measurement.

In an embodiment, the processing component of the invasive analyte measurement device 302 may be configured to relay reconfiguration instructions from the cloud-based server 306 to the non-invasive glucometer. The reconfiguration instructions may reconfigure a sensitivity or a sampling rate of the non-invasive glucometer. The processing component may also be configured to: update a size of the data batch to accommodate the sampling rate; and/or update a frequency at which the data batch is sent to the cloud-based server. The sampling rate may be reconfigured based on the reconfiguration instructions. The processing component may be configured to: take a third glucose measurement after receiving the set of subsequent glucose measurements from the non-invasive glucometer; assign the third glucose measurement to a new data batch. The processing component may be prompted to send the data batch upon receiving the third glucose measurement. The processing component may be configured to: receive a request from another device for an individual measurement; pull the individual measurement from the data batch; and send the individual measurement to the other device requesting the individual measurement, the individual measurement sent separately from the data batch. The other device may include the cloud-based server 306 or the user device 308. The individual measurement may include the first glucose measurement, the second glucose measurement, or one of the set of subsequent glucose measurements by the non-invasive glucometer.

Figure 3B:
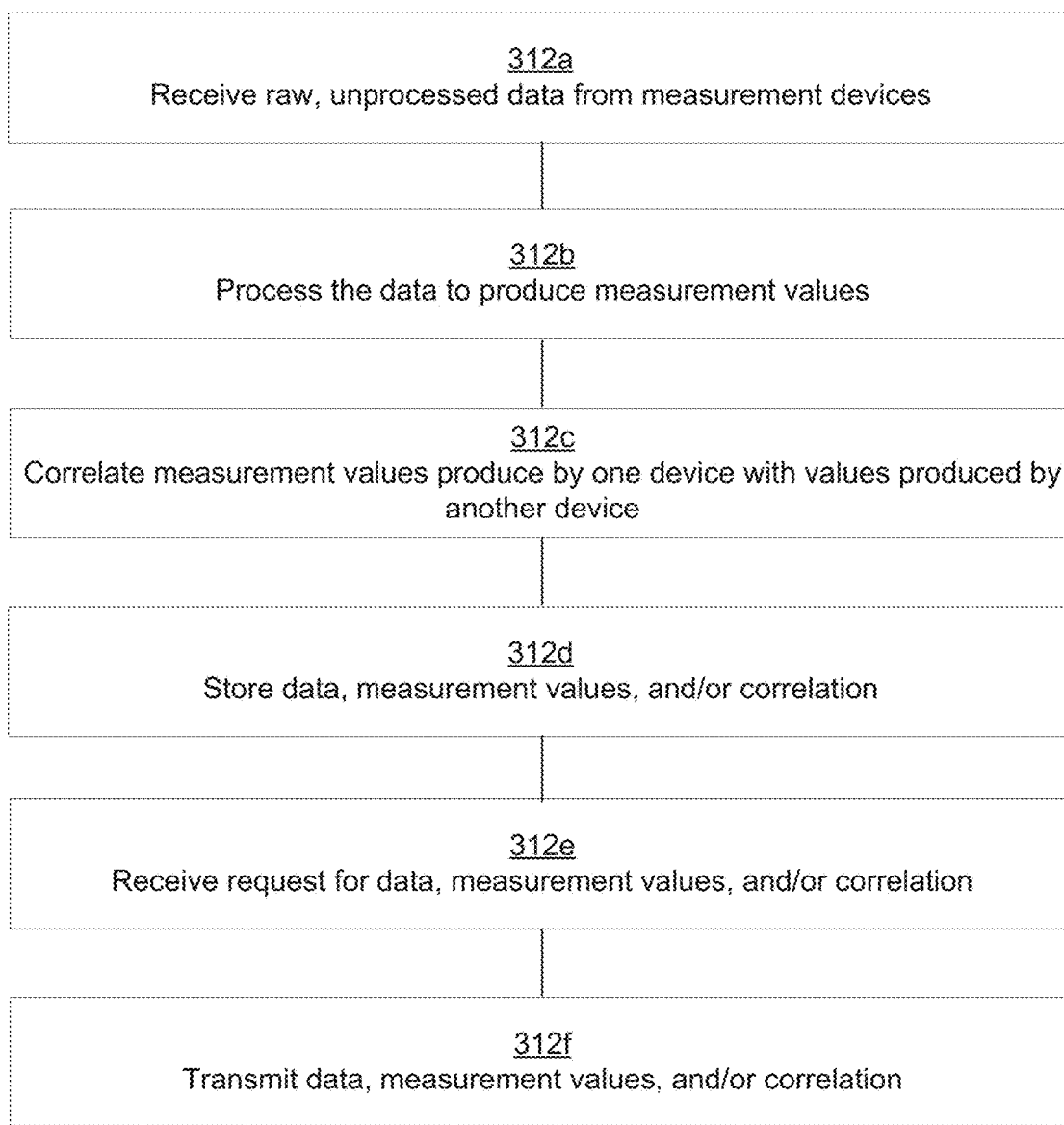
FIG. 3B illustrates a method of processing and/or correlating raw measurement data at a cloud-based server, the raw measurement data collected by measurement devices networked to the cloud-based server in a health device network such as the configuration described regarding FIG. 3A, according to an embodiment.

FIG. 3B illustrates a method 312 of processing and/or correlating raw measurement data at a cloud-based server 306, the raw measurement data collected by measurement devices networked to the cloud-based server in a health device network such as the configuration described regarding FIG. 3A, according to an embodiment. Some of the features in FIG. 3B are the same as or similar to some of the features in FIGS. 1A-3A as noted by same and/or similar reference characters, unless expressly described otherwise. Additionally, reference may be made to features shown in any of FIGS. 1A-3A and not shown in FIG. 3B. The cloud-based server may include the cloud-based server 306. The measurement devices may include the wearable device 100, the invasive analyte measurement device 302, and/or the peripheral measurement device(s) 304.

The method 312 may include receiving, at the cloud-based server 306, first data from a first measurement device and/or second data from a second measurement device (block 312a). The first data and/or the second data may include raw, unprocessed measurement data. For example, the first data and/or the second data may include electrical current and/or electrical potential data. The first data and/or the second data may include minimally processed measurement data. For example, the first measurement device may locally process raw data to yield a measurement value or values such as blood glucose level, weight, blood pressure, and so forth. The measurement value or values may form the first data. Similarly, the second measurement device may locally process raw data to yield a measurement value or values and/or compile the measurement value or values to form the second data.

The method 312 may include processing, at the cloud-based server, the first data to determine a first measurement value or set of values associated with the first data, and/or processing, at the cloud-based server, the second data to determine a second measurement value or set of values associated with the second data (block 312b). The cloud-based server may store the first data and/or the second data after processing or may discard the first data and/or the second data after processing. The cloud-based server may store the first measurement value or set of values. The cloud-based server may tag the first measurement value or set of values as being associated with the first measurement device. The cloud-based server may store the second measurement value or set of values. The cloud-based server may tag the second measurement value or set of values as being associated with the second measurement device.

The method 312 may include correlating, at the cloud-based server, the first measurement value or set of values with the second measurement value or set of values (block 312c). The first data and/or the second data may be time-indexed. The time indexing may enable correlation of the first data to the second data such that the cloud-based server may determine that a measurement by the first measurement device was taken at or proximate to a same time as a measurement by the second measurement device. Proximate may refer to a temporal proximity relative to measurement type. For example, the first measurement value may be weight and the second measurement value may be blood pressure. The time indexing may be daily. In another example, the first measurement device may include the invasive analyte measurement device 302 and the second measurement device may include the wearable device 100. The first measurement value may be blood glucose invasively measured and the second measurement value may be blood glucose non-invasively measured. The time indexing may be by minute, such that the first measurement was taken within one minute of the second measurement. Additionally, the time indexing may enable the cloud-based server to compare non-concurrent measurement data, such as correlating measurements taken by the first measurement device at a first time to measurements taken by the second measurement device at a second time subsequent to the first time.

The correlating of the first measurement value or set of values with the second measurement value or set of values may include multivariate analysis to determine a strength of a relationship between a first underlying physiological characteristic associated with the first measurement value or set of values and a second underlying physiological characteristic associated with the second measurement value or set of values. The cloud-based server may store the relationship strength and/or update the relationship strength as the cloud-based server receives more measurement data from the first measurement device and/or the second measurement device. The relationship strength may be correlative such that changes in the first underlying physiological characteristic are accompanied by changes in the second underlying physiological characteristic. The relationship strength may be causative such that changes in the first underlying physiological characteristic cause changes in the second underlying physiological characteristic. The relationship strength may show the first underlying physiological characteristic and the second underlying physiological characteristic are loosely related and/or unrelated.

The method 312 may include storing, on the cloud-based server, the first data, the second data, first measurement value or set of values, the second measurement value or set of values, and/or the correlation between the first measurement value or set of values and the second measurement value or set of values (block 312d). The method 312 may include receiving, at the cloud-based server, a request from a user device for the first data, the second data, first measurement value or set of values, the second measurement value or set of values, and/or the correlation between the first measurement value or set of values and the second measurement value or set of values (block 312e). The method 312 may include transmitting, from the cloud-based server, the first data, the second data, first measurement value or set of values, the second measurement value or set of values, and/or the correlation between the first measurement value or set of values and the second measurement value or set of values (block 312f).

The user device may include the wearable device 100, the invasive analyte measurement device 302, one or more of the peripheral measurement device(s) 304, and/or the user device 308. The request may be received by the cloud-based server before the first data and/or the second data is received by the cloud-based server. The request may include a standing request such that the cloud-based server automatically processes and transmits, upon receipt of the first data and/or the second data, the first data, the second data, the first measurement value or set of values, the second measurement value or set of values, and/or the correlation between the first measurement value or set of values and the second measurement value or set of values. The cloud-based server may transmit the first data, the second data, the first measurement value or set of values, the second measurement value or set of values, and/or the correlation between the first measurement value or set of values and the second measurement value or set of values without and/or before receiving the request. For example, the cloud-based server may include instructions to automatically transmit the first data, the second data, the first measurement value or set of values, the second measurement value or set of values, and/or the correlation between the first measurement value or set of values and the second measurement value or set of values.

The request may be received simultaneously with receiving the first data and/or the second data. For example, the first data and/or the second data may include the request. The request may be received before the cloud-based server processes the first data and/or the second data. For example, the cloud-based server may store the first data and/or the second data and may be prompted to process the first data and/or the second data upon receiving a request for the first data, the second data, the first measurement value or set of values, the second measurement value or set of values, and/or the correlation between the first measurement value or set of values and the second measurement value or set of values. The request may be received after the cloud-based server processes the first data and/or the second data.

The request may include a generic request for data. For example, the request may not specify a type of data requested, where type may refer to whether the data is raw data, processed data, correlated data, measurement values, and so forth. The request may include an identifier that may identify a type of device and/or a specific device requesting the data. The cloud-based server may include instructions on what data to transmit based on the type of device and/or the specific device requesting the data. For example, the identifier may indicate the requesting device is the wearable device 100. The cloud-based server may store instructions to transmit a packet of data including a correlation between a hydration measurement by the wearable device and a blood glucose measurement taken by the invasive analyte measurement device 302.

In another embodiment, a method of processing and/or correlating raw measurement data at a cloud-based server 306 may include: aggregating a set of raw data into a raw data batch; transmitting the raw data batch to the cloud-based server 306; receiving a confirmation the raw data batch is received by the cloud-based server 306; deleting the raw data batch from local memory after receiving the confirmation; and receiving processed data from the cloud-based server, the processed data based on the data batch and output by the data analytics application 306e. The raw data batch may include: a first measurement by the invasive analyte measurement device 302 and a second measurement by a non-invasive glucometer; and/or the first measurement, the second measurement, and a third measurement by a health measurement device such as one of the peripheral measurement devices 304. A data point of the set of raw data may include: an electronic signal correlated to a device tag indicating a measurement device outputting the electronic signal; an analyte level; or a value providing indication of a quality or a quantity of a physiological characteristic. The data analytics application 306e may be hidden on the cloud-based server 306 from the invasive analyte measurement device 302, the non-invasive glucometer, and the health measurement device.

In an embodiment, a method of processing and/or correlating raw measurement data at a cloud-based server 306 may include: taking the first measurement; and receiving, directly from the non-invasive glucometer, the second measurement. The invasive analyte measurement device 302 may aggregate the set of raw data. In an embodiment, a method may include: taking the second measurement; and receiving, directly from the invasive glucometer, the first measurement. The non-invasive glucometer may aggregate the set of raw data. Transmitting the raw data batch may be prompted by: the raw data batch occupying a threshold amount of physical memory; the raw data batch comprising a threshold number of the first measurement or the second measurement; a threshold amount of time passing after the first measurement is taken; a third measurement being taken by the invasive glucometer; and/or receiving a request for the raw data batch.

Figure 3C:
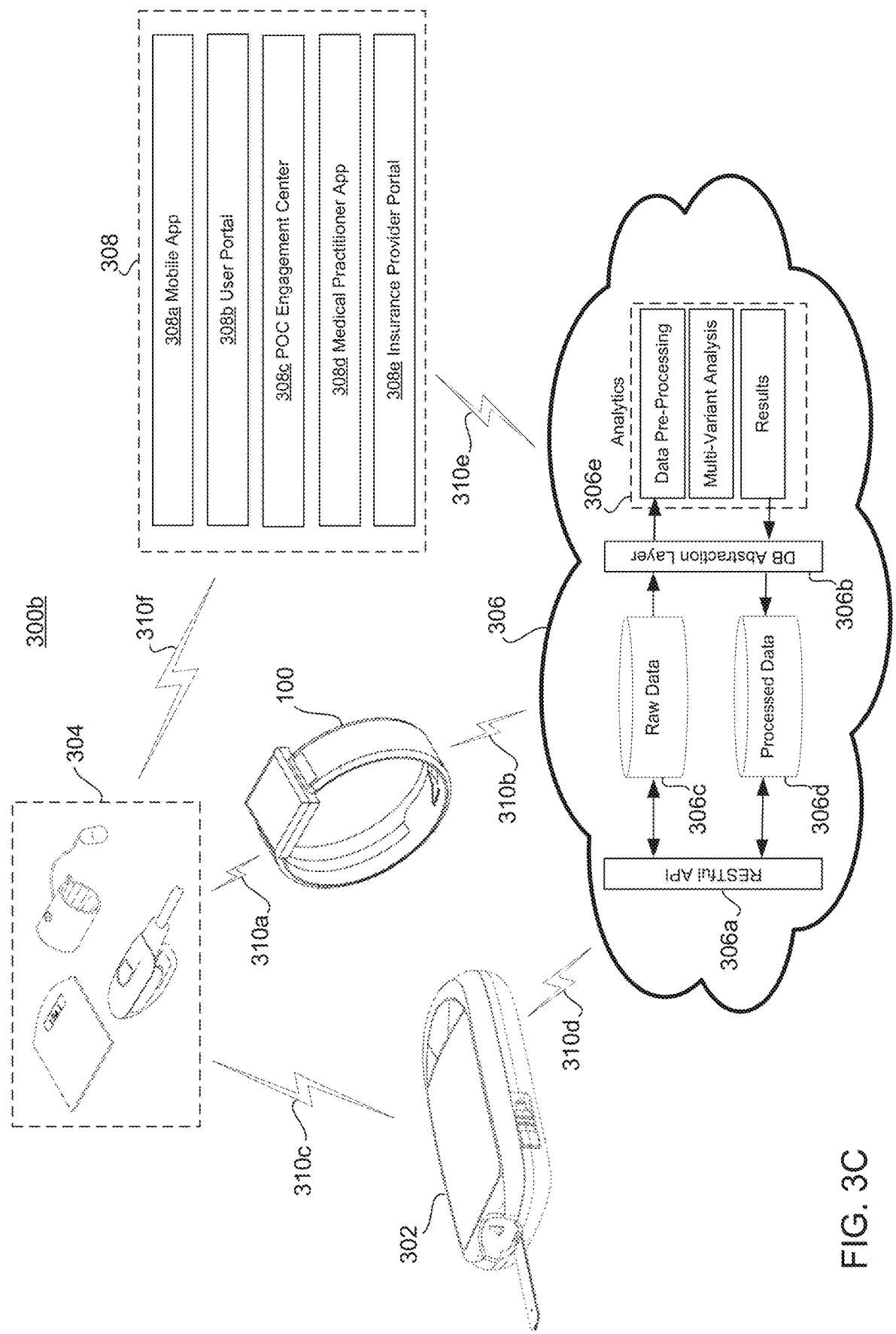
FIG. 3C illustrates a health device network configuration for communicating health data, including a network communication link between peripheral measurement devices and a user device, according to an embodiment.

FIG. 3C illustrates a health device network configuration 300b for communicating health data, including a sixth network communication link 310f between the peripheral measurement device(s) 304 and the user device 308, according to an embodiment. Some of the features in FIG. 3C are the same as or similar to some of the features in FIGS. 1A-3B as noted by same and/or similar reference characters, unless expressly described otherwise. Additionally, reference may be made to features shown in any of FIGS. 1A-3B and not shown in FIG. 3C. The health device network configuration 300b may include the wearable device 100, the invasive analyte measurement device 302, the one or more peripheral measurement device(s) 304, the cloud-based server 306, and the user device 308. The wearable device 100 and the peripheral measurement device(s) 304 may communicate over the first network communication link 310a. The wearable device 100 and the cloud-based server 306 may communicate over the second network communication link 310b. The invasive analyte measurement device 302 and the peripheral measurement device(s) 304 may communicate over the third network communication link 310c. The invasive analyte measurement device 302 and the cloud-based server 306 may communicate over the fourth network communication link 310d. The cloud-based server 306 and the user device 308 may communicate over the fifth network communication link 310e. The peripheral measurement device(s) 304 and the user device 308 may communicate over the sixth network communication link 310f.

The peripheral measurement device(s) 304 and the user device 308 may be networked in a PAN, a NAN, a LAN, a CAN, a WAN, an IAN, or via the Internet. In various embodiments, the sixth network communication link 310f may include a direct communication link. For example, the sixth network communication link 310f may include a Bluetooth™ connection. In another example, the seventh network communication link 310g may include a hardwire ethernet connection between an ethernet port on an individual peripheral measurement device and an ethernet port on the user device 308. In various embodiments, the sixth network communication link 310f may include an indirect communication link. For example, the sixth network communication link 310f may include a WiFi connection routed between the peripheral measurement device(s) 304 and the user device 308 via a network switch and/or WiFi router. In another example, the sixth network communication link 310f may include two or more physically different types of links, such as a wired link and a wireless link, routed over a local network or over the Internet. The peripheral measurement device(s) 304 may have Internet Protocol (IP) addresses which may be accessible by a device connected to the Internet.

In various embodiments, the health device network configuration 300b may be situated in a healthcare provider office or on a healthcare provider campus. The peripheral measurement device(s) 304 may include devices for obtaining physiological characteristics of a patient such as the patient's height, weight, blood pressure, resting pulse, blood oxygen saturation, blood sugar level, and so forth. The peripheral measurement device(s) 304 may be networked to the user device 308 via the sixth network communication link 310f, and the user device 308 may be networked to the cloud-based server 306 via the fifth network communication link 310e.

In some embodiments, data and/or measurements collected by the peripheral measurement device(s) 304 may be processed and/or analyzed at the peripheral measurement device taking the measurement and/or collecting the data. For example, a weight scale may determine a weight based on an output by a strain gauge sensor and display the weight on a display integrated into the weight scale.

In some embodiments, data and/or measurements collected by the peripheral measurement device(s) 304 may be communicated to the user device 308 via the sixth network communication link 310f and processed and/or analyzed at the user device 308. For example, a blood pressure monitor may transmit raw data to a handheld computing device such as a tablet. The tablet may process the raw data and determine a blood pressure corresponding to the raw data transmitted by the blood pressure monitor. The tablet may display the blood pressure to a user of the tablet such as a healthcare provider.

In some embodiments, data and/or measurements collected by the peripheral measurement device(s) 304 may be communicated to the user device 308 via the sixth network communication link 310f and communicated by the user device 308 to the cloud-based server 306 via the fifth network communication link 310e. The cloud-based server 306 may process and/or analyze the raw data. For example, a healthcare provider may evaluate a patient's health status over a period of time, such as over an hour, over several hours, over a day, over several days, and so forth. The evaluation may involve collecting time-indexed raw data by several peripheral measurement device(s) 304. The time-indexed raw data may be communicated to the cloud-based server 306 through the user device 308. Individual peripheral measurement devices may process the respective raw data collected by the individual peripheral measurement device and display values determined based on the raw data to the patient and/or a user viewing the individual peripheral measurement device. The user device 308 may process the raw data communicated from the peripheral measurement device(s) 304 and display the raw data from the peripheral measurement device(s) 304 to a user such as a healthcare provider. The cloud-based server 306 may aggregate the time-indexed raw data in the raw data database 306c, and the data analytics application 306e may process the time-indexed raw data to generate diagnostics of the patient's health status. For example, the data analytics application 306e may determine based on an EKG reading, sonographic heartbeat measurement data, and pulse oximetry measurement data that the patient has a leaky heart valve.

Direct communication of data between the user device 308 and the peripheral measurement device(s) 304 may allow a user greater control over and/or on-demand access to measurement data. For example, the user may require a weight measurement. The patient may stand on the scale and the patient's weight may automatically populate on the user device 308 as the weight measurement is received at the user device 308 directly from the weight scale. The weight may simultaneously be aggregated at, for example, the wearable device 100 with other measurement data and transmitted to and stored at the cloud-based server 306 for analysis. Thus, direct communication by the weight scale with the user device 308 makes the measurement immediately available to the user while aggregation of the weight measurement with other measurement data enables more detailed analysis of the patient's overall health.

Figure 3D:
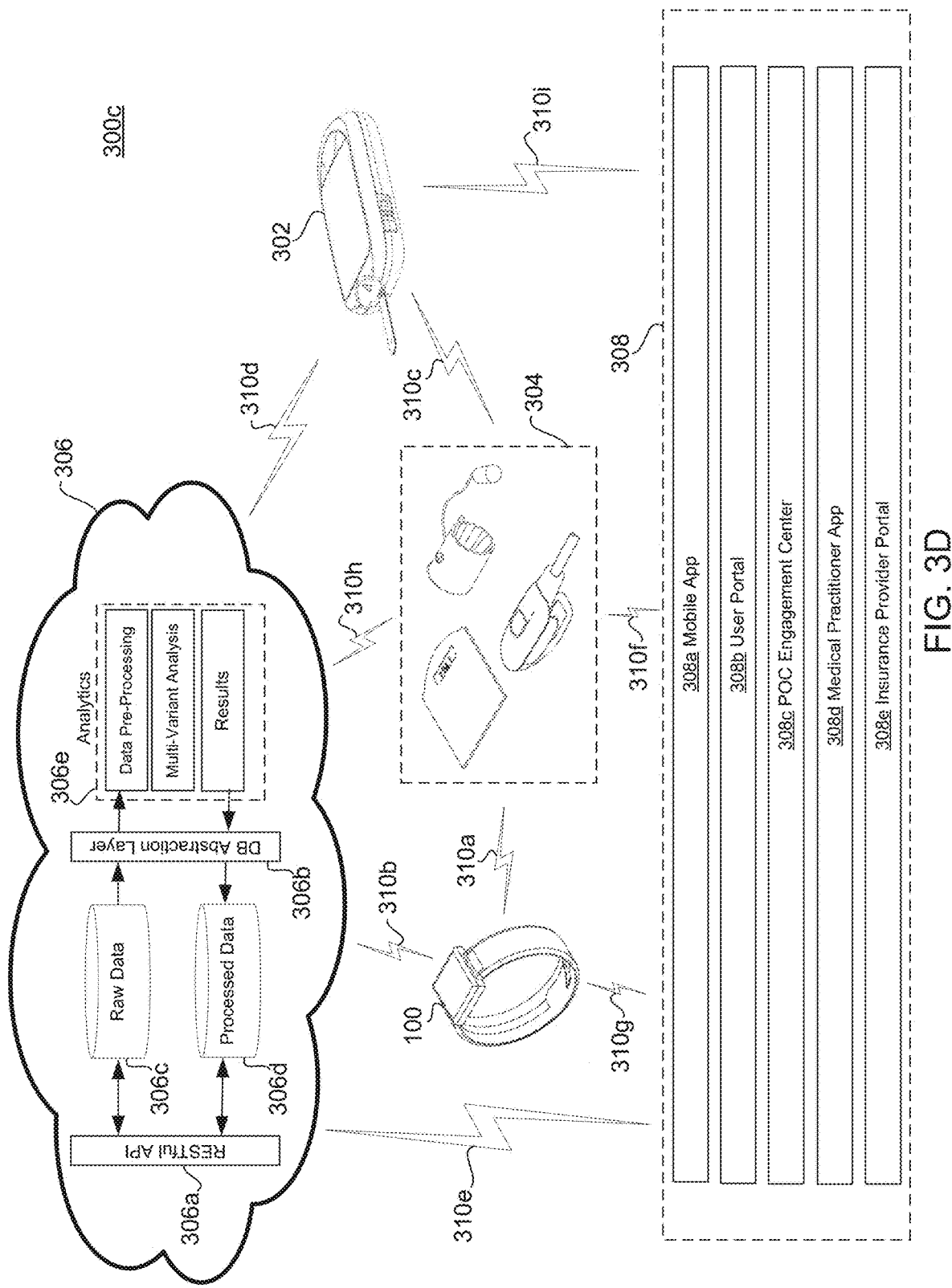
FIG. 3D illustrates a health device network configuration for communicating health data, including a network communication link between a wearable device and the user device, a network communication link between the peripheral measurement devices and a cloud-based server, and a network communication link between an invasive analyte measurement device and the user device, according to an embodiment.

FIG. 3D illustrates a health device network configuration 300c for communicating health data, including a seventh network communication link 310g between the wearable device 100 and the user device 308, an eighth network communication link 310h between the peripheral measurement device(s) 304 and the cloud-based server 306, and a ninth network communication link 310i between the invasive analyte measurement device 302 and the user device 308, according to an embodiment. Some of the features in FIG. 3D are the same as or similar to some of the features in FIGS. 1A-3C as noted by same and/or similar reference characters, unless expressly described otherwise. Additionally, reference may be made to features shown in any of FIGS. 1A-3C and not shown in FIG. 3D. The health device network configuration 300c may include the wearable device 100, the invasive analyte measurement device 302, the peripheral measurement device(s) 304, the cloud-based server 306, and/or the user device 308. The wearable device 100 and the peripheral measurement device(s) 304 may communicate over the first network communication link 310a. The wearable device 100 and the cloud-based server 306 may communicate over the second network communication link 310b. The invasive analyte measurement device 302 and the peripheral measurement device(s) 304 may communicate over the third network communication link 310c. The invasive analyte measurement device 302 and the cloud-based server 306 may communicate over the fourth network communication link 310d. The cloud-based server 306 and the user device 308 may communicate over the fifth network communication link 310e. The peripheral measurement device(s) 304 and the user device 308 may communicate over the sixth network communication link 310f. The wearable device 100 and the user device 308 may communicate over the seventh network communication link 310g. The peripheral measurement device(s) 304 and the cloud-based server 306 may communicate over the eighth network communication link 310h. The invasive analyte measurement device 302 and the user device 308 may communicate over the ninth network communication link 310i.

The wearable device 100 and the user device 308 may be networked in a PAN, a NAN, a LAN, a CAN, a WAN, an IAN, or via the Internet. In various embodiments, the seventh network communication link 310g may include a direct communication link. For example, the seventh network communication link 310g may include a Bluetooth™ connection. In another example, the seventh network communication link 310g may include a hardwire USB connection between a USB port on the wearable device 100 and a USB port on the user device 308. In various embodiments, the seventh network communication link 310g may include an indirect communication link. For example, the seventh network communication link 310g may include a WiFi connection routed between the wearable device 10 and the user device 308 via a network switch and/or WiFi router. In another example, the seventh network communication link 310g may include two or more physically different types of links, such as a wired link and a wireless link, routed over a local network or over the Internet. The wearable device 100 and the user device 308 may have respective IP addresses which may be accessible by devices connected to the Internet.

The peripheral measurement device(s) 304 and the cloud-based server 306 may be networked in a LAN, a CAN, a WAN, an IAN, or via the Internet. In various embodiments, the eighth network communication link 310h may include a direct communication link. For example, the eighth network communication link 310h may include a hardwire ethernet connection between an ethernet port on an individual peripheral measurement device and an ethernet port on a bare metal, locally situated implementation of the cloud-based server 306. In various embodiments, the eighth network communication link 310h may include an indirect communication link and/or two or more physically different types of links. For example, the eighth network communication link 310h may include a WiFi connection between the peripheral measurement device(s) 304 and a WiFi router. The WiFi router may be networked to the Internet. The cloud-based server 306 may also be networked to the Internet. The peripheral measurement device(s) 304 may have respective IP addresses, and the cloud-based server 306 may have an IP address. The peripheral measurement device(s) 304 and the cloud-based server 306 may accordingly communicate over the Internet using the respective IP addresses.

The invasive analyte measurement device 302 and the user device 308 may be networked in a PAN, a NAN, a LAN, a CAN, a WAN, an IAN, or via the Internet. In various embodiments, the ninth network communication link 310i may include a direct communication link. For example, the ninth network communication link 310i may include a Bluetooth™ connection. In another example, the ninth network communication link 310i may include a hardwire USB connection between a USB port on the invasive analyte measurement device 302 and a USB port on the user device 308. In various embodiments, the ninth network communication link 310i may include an indirect communication link. For example, the ninth network communication link 310i may include a WiFi connection routed between the invasive analyte measurement device 302 and the user device 308 via a network switch and/or WiFi router. In another example, the ninth network communication link 310i may include two or more physically different types of links, such as a wired link and a wireless link, routed over a local network or over the Internet. The invasive analyte measurement device 302 and the user device 308 may have respective IP addresses which may be accessible by devices connected to the Internet.

In various embodiments, the health device network configuration 300c may be situated across a variety of locations that may encompass a healthcare provider office, a hospital, a healthcare provider call center, a data center, and/or a patient's home. Indeed, the health device network configurations 300a and 300b may be similarly situated across a variety of locations. The peripheral measurement device(s) 304 may include individual devices located at the healthcare provider office, at the hospital, and in the patient's home. The patient may wear the wearable device 100, which may accompany the patient wherever the patient goes while wearing the wearable device 100. The patient may carry the invasive analyte measurement device 302 with the patient as the patient travels from one location to another, or the invasive analyte measurement device 302 may be left at the patient's home or another location frequented by the patient. The user device 308 may include a mobile phone and/or computer of the patient, a computer and/or tablet used by a healthcare provider and located in the healthcare provider office, and/or a computer used by a healthcare provider call center employee. The cloud-based server 306 may include a bare metal server located at the healthcare provider office, at the healthcare provider call center, and/or in a data center.

The healthcare provider office may be situated in the same and/or neighboring metropolitan area as the patient's home. The healthcare provider call center may be situated in the healthcare provider office, on the same campus as the healthcare provider office, in the same metropolitan area as the patient's home and/or the healthcare provider office, and/or in another metropolitan area as the patient's home and/or the healthcare provider office. The data center may be situated in or on the same campus as the healthcare provider office, in or on the same campus as the healthcare provider call center, in the same metropolitan area as the healthcare provider office, in the same metropolitan area as the healthcare provider call center, in the same metropolitan area as the patient's home, or in a different metropolitan area than the healthcare provider office, the healthcare provider call center, and/or the patient's home.

The elements of the health device network configuration 300c, including the wearable device 100, the invasive analyte measurement device 302, the peripheral measurement device(s) 304, the cloud-based server 306, and/or the user device 308 may be fully interconnected with each other such that the elements may be communicatively coupled to each other element. Accordingly, the health device network configuration 300c may be fully meshed, which may include another network communication link between the wearable device 100 and the invasive analyte measurement device 302. Elements of the health device network configuration 300c may be configured, i.e. via programming and/or instructions stored and executed on processors local to the elements, to process, store, and/or display data collected and/or measurements taken by the peripheral measurement device(s) 304, the wearable device 100, and/or the invasive analyte measurement device 302. The peripheral measurement device(s) 304, the wearable device 100, and/or the invasive analyte measurement device 302 may be configured to transmit the data and/or measurements to the cloud-based server 306. The cloud-based server 306 may be configured to analyze the data and/or measurements and transmit the analysis to the peripheral measurement device(s) 304, the wearable device 100, the invasive analyte measurement device 302, and/or the user device 308. Examples and/or embodiments described regarding the health device network configuration described herein may be implemented in health device network configurations where network communication links are provided to enable such examples and/or embodiments.

The health device network configuration 300c may represent a fully-meshed or semi-meshed network. In a fully-meshed embodiment, the health device network configuration 300c may include a network connection between the wearable device 100 and the invasive analyte measurement device 302. The fully-meshed network configuration may allow for network redundancy to ensure measurement data is not lost. For example, the cloud-based server 306 may prioritize storage of aggregated measurement data from the wearable device 100 and/or the invasive analyte measurement device 302. The peripheral measurement device(s) 304 may transmit measurement data to the wearable device 100 and/or the invasive analyte measurement device 302 for aggregation of the measurement data. Simultaneously, the peripheral measurement device(s) 304 may transmit the measurement data to the cloud-based server 306. The cloud-based server may silo the measurement data received directly from the peripheral measurement device(s) 304 for comparison with aggregated measurement data received from the wearable device 100 and/or the invasive analyte measurement device 302. If the aggregated measurement data includes all the siloed measurement data, then the siloed measurement data may be discarded. However, if the aggregated measurement data is missing data that is included in the siloed data, the aggregated measurement data may be supplemented with the missing data from the siloed data. Thus, the redundancy of the fully- or semi-meshed network configuration may ensure data is not lost.

Figure 3E:
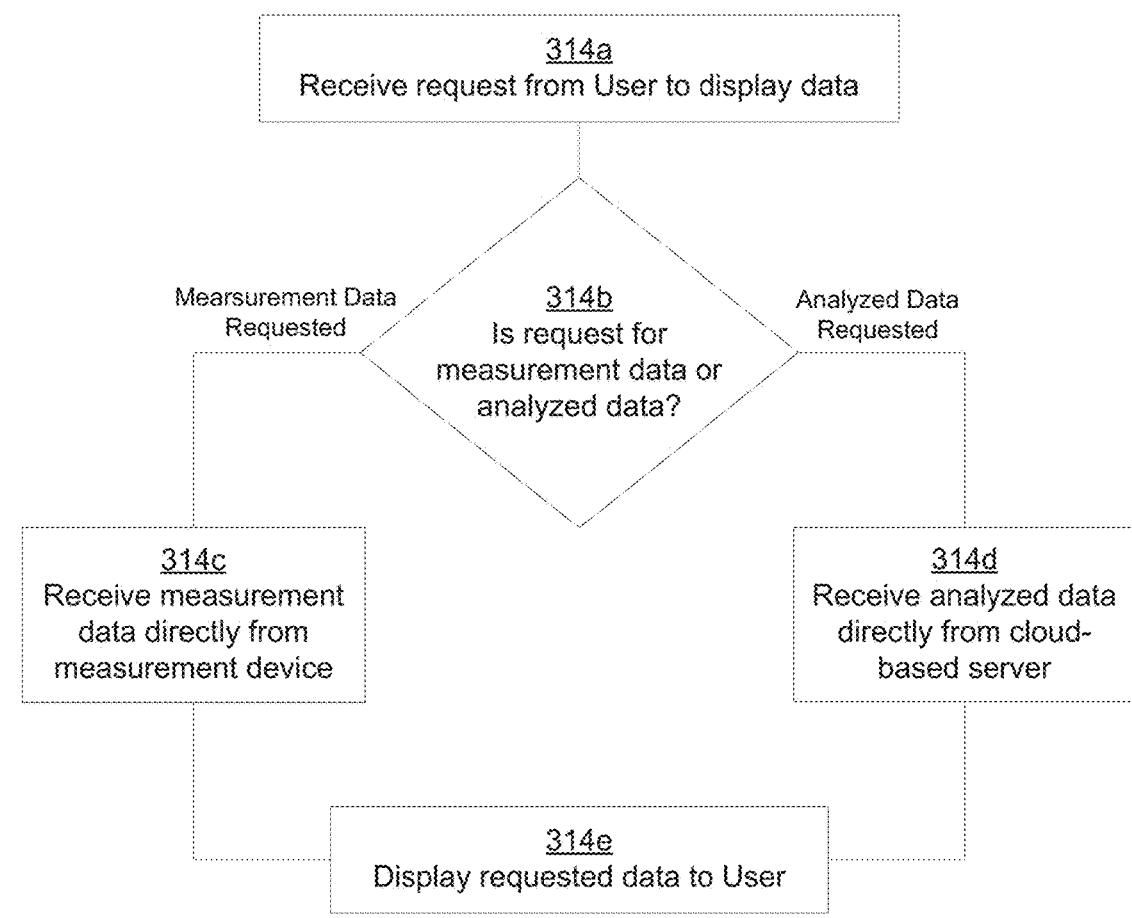
FIG. 3E illustrates a method of efficiently displaying data on a user device, the data collected by measurement devices and analyzed by a cloud-based server, according to an embodiment.

FIG. 3E illustrates a method 314 of efficiently displaying data on a user device, the data collected by measurement devices and analyzed by a cloud-based server, according to an embodiment. Some of the features in FIG. 3E are the same as or similar to some of the features in FIGS. 1A-3D as noted by same and/or similar reference characters, unless expressly described otherwise. Additionally, reference may be made to features shown in any of FIGS. 1A-3D and not shown in FIG. 3E. The user device may include the user device 308. The measurement devices may include the wearable device 100, the invasive analyte measurement device 302, and/or the peripheral measurement device(s) 304. The cloud-based server may include the cloud-based server 306. The user device, the measurement devices, and the cloud-based server may communicate via a health device network such as the configurations described regarding FIGS. 3A, 3C and/or 3D.

The method 314 may include receiving a request at the user device for data (block 314a). The request may be received by a direct user of the user device. The request may include instructions to display the data to the user by the user device. The method 314 may include determining whether the data requested is for measurement data or for analyzed data (block 314b). Measurement data may include raw measurement data such as electric current or potential data. Measurement data may include processed measurement data in the form of a measurement value such as blood glucose level, weight, blood pressure, and so forth. Analyzed data may include measurement trends, correlations between measurements taken by different devices, whether a measurement value indicates a healthy condition or an unhealthy condition, and so forth. The method 314 may include receiving measurement data directly from the measurement data (block 314c). The method 314 may include receiving analyzed data directly from the cloud-based server (block

314*d*). The method 314 may include displaying the requested data to the user (block 314*e*).

The method 314 may efficiently allocate device memory and/or processing capacity for devices in the health device network. Measurement devices may be subject to hardware constraints such as size and power constraints. Such constraints may make it inefficient to analyze data locally at the measurement device, especially when analysis may include analysis of data from other devices. Data analysis may place large demands on transitory memory and may consume significant amounts of power. Data analysis may process large amounts of data, and the measurement device may not have enough local memory to store the large amount of data. Accordingly, it may be most efficient for the measurement devices to communicate measurement data to the cloud-based server, for the cloud-based server to store and analyze the data, and for the user device to request the analyzed data from the cloud-based server. Additionally, it is more likely that requested analyzed data may include large amounts of data taken over relatively long time frames and not susceptible to strong variation over short time frames, such as a time frame over which a user may view the requested data, which may range from a few seconds to a few hours. A user may request measurement data to directly view live measurement data. Sending single measurements and/or live measurement data may have relatively low memory and/or power requirements and may therefore be more efficiently communicated directly to the user device as opposed to routing the data through the cloud-based server.

Figure 3F:
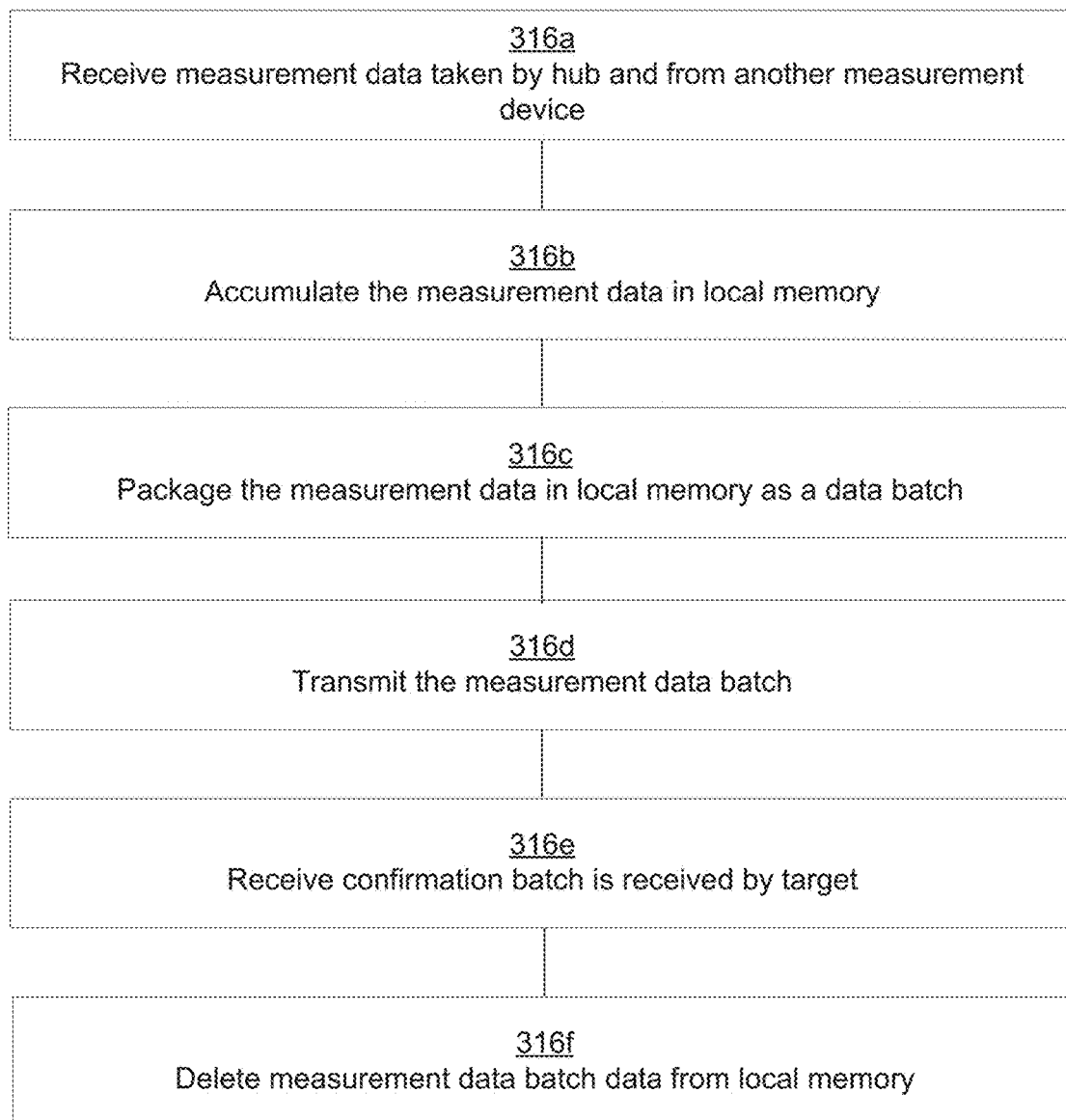
FIG. 3F illustrates a method of routing measurement data through a measurement device hub in a health device network such as the configurations described regarding FIGS. 3A, 3C and/or 3D, according to an embodiment.

FIG. 3F illustrates a method 316 of routing measurement data through a measurement device hub in a health device network such as the configurations described regarding FIGS. 3A, 3C and/or 3D, according to an embodiment. Some of the features in FIG. 3F are the same as or similar to some of the features in FIGS. 1A-3E as noted by same and/or similar reference characters, unless expressly described otherwise. Additionally, reference may be made to features shown in any of FIGS. 1A-3E and not shown in FIG. 3F. The measurement device hub may include an analyte measurement device such as the invasive analyte measurement device 302 and/or a non-invasive analyte measurement device such as the wearable device 100. In an embodiment, the invasive analyte measurement device 302 may include an invasive glucometer and the non-invasive analyte measurement device may include a non-invasive glucometer. The wearable device 100 may be referred to as a non-invasive glucometer. The measurement data may be collected by the measurement device hub and/or a peripheral device such as the peripheral measurement device(s) 304. The data may be routed to a server such as the cloud-based server 306 and/or a user device such as the user device 308.

The method 316 may include receiving measurement data at the measurement device hub (block 316*a*). The measurement data may be collected by the measurement device hub or the peripheral device. The measurement data may include raw data and/or minimally processed data. The measurement data may include time indexing of the raw and/or minimally processed data. The measurement data may be indexed to a calendar and/or clock time, as opposed to an internal clock and/or time of the measurement device hub and/or the peripheral device. The method 316 may include accumulating the measurement in local memory of the measurement device hub (block 316*b*). The method may include packaging the measurement data in local memory as a data batch (block 316*c*). The data batch may include a time index for the measurement data in the data batch. For example, the data batch may include measurement data from a blood pressure cuff, a weight scale, and an invasive glucometer. The data batch may include a first data column for blood pressure data, a second data column for weight, a third data column for blood glucose, and a fourth data column for time. The data batch may include a row for a time corresponding to a measurement. Columnar entries in a row may include measurements taken at the time corresponding to the row.

The method 316 may include transmitting the data batch from the measurement device hub to the server and/or the user device (block 316*d*). The measurement device hub may be prompted to transmit the data batch periodically, such as upon expiration of an amount of time since a previous data batch transmission. The measurement device hub may be prompted to transmit the data batch by a request. The request may be made by a user of the measurement device hub. For example, the measurement device hub may include an invasive glucometer with a user interface. The user may request, via the user interface the data batch be transmitted to the server and/or the user device. The request may be made from the server and/or the user device. The request may be automatic based on a maximum and/or minimum data batch size. For example, the measurement device hub may include instructions to transmit the data batch after the data batch reaches a threshold size. Upon receiving the request, the measurement device hub may "close" the data batch by redirecting measurement data received after the request to a different data batch.

The method 316 may include listening for and/or receiving at the measurement device hub a confirmation the data batch is received by a target (block 316*e*). For example, the target may include the server and/or the user device. The server and/or the user device may transmit a receipt confirmation to the measurement device hub after the data batch is received by the server and/or the user device. The method 316 may include deleting the data batch from the measurement device hub local memory (block 316*f*). The measurement device hub may include instructions to delete the data batch after the confirmation is received from the target.

The method 316 may ensure measurement data security, minimize the necessity of storage at the measurement device, and/or prevent reverse-engineering of proprietary data analytics programs. Health data privacy may be a great concern for patients. Local memory in measurement devices may be susceptible to attacks to obtain a patient's private health data. Thus, aggregating measurement data, transmitting the measurement data to a secure device, and deleting the data from local memory may protect against attempts to steal data from a local measurement device. Additionally, deleting historical measurement data may minimize memory requirements, thus allowing electronic components of measurement devices to be smaller, more compact, and/or more efficient. Sequestering analytics programming and/or instructions to a secure cloud-based server (e.g. the cloud-based server 306) may enhance the security of the programming and/or instructions and allow for the use of proprietary and/or trade secret analytics programming and/or instructions while minimizing the risk the programming and/or instructions are uncovered and stolen by a competitor.

Figure 4A:
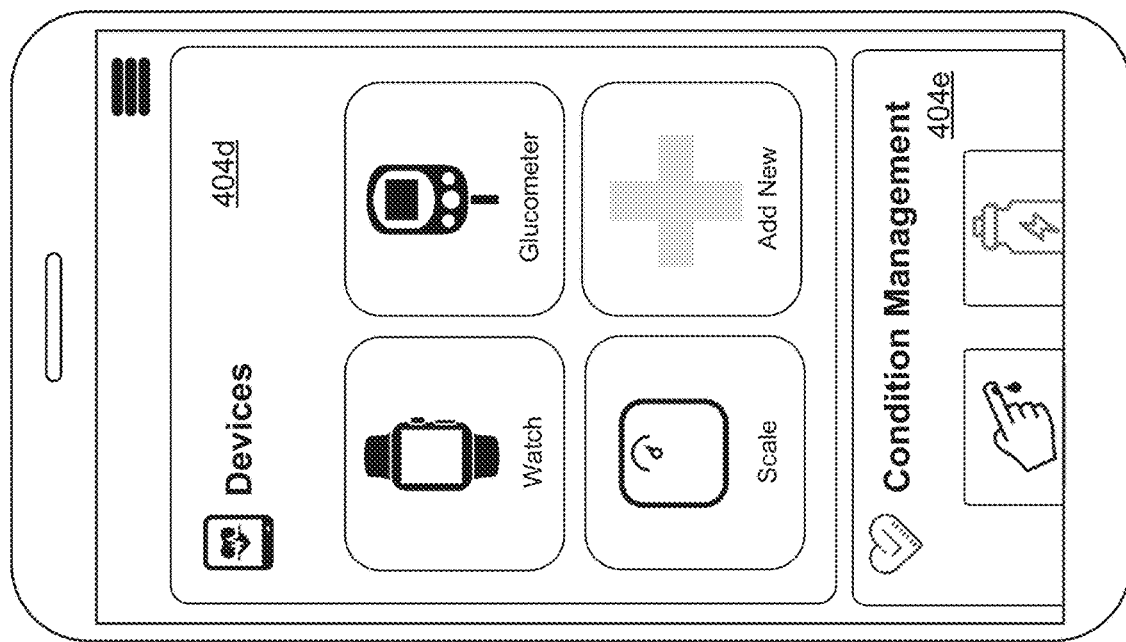
FIG. 4A illustrates the user device described regarding FIGS. 3A-C as a mobile phone running a mobile application, according to an embodiment.
Figure 4A:
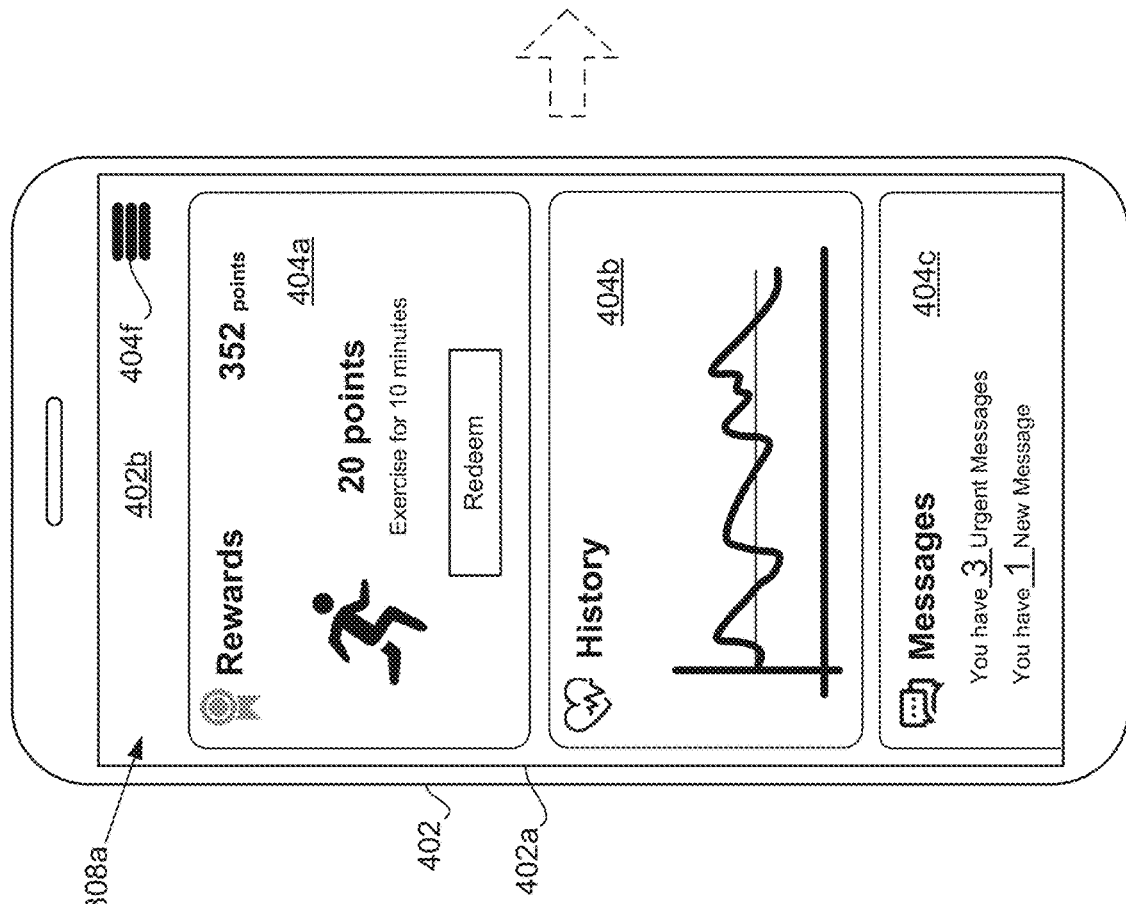

FIG. 4A illustrates the user device 308 described regarding FIGS. 3A-C as a mobile phone 402 running the mobile application 308*a*, according to an embodiment. Some of the features in FIG. 4A are the same as or similar to some of the features in FIGS. 1A-3F as noted by same and/or similar reference characters, unless expressly described otherwise. Additionally, reference may be made to features shown in any of FIGS. 1A-3F and not shown in FIG. 4A. The mobile phone 402 may include a touchscreen 402*a* displaying a GUI 402b. Via the GUI 402b, the mobile application 308a may display information to the user and may accept input from the user. The information may be displayed to the user via one or more modules. The modules may, in an embodiment, include a rewards module 404a, a history module 404b, a messages module 404c, a devices module 404d, a condition management module 404e, and/or a menu module 404f. Various other embodiments may include these and/or other modules, including an appointment module, a share module, a healthcare provider finder module, a social networking module, a disease selection module, and so forth. For example, in an embodiment, the social networking module may allow the patient to share health information such as progress towards goals in disease management. In an embodiment, the disease module may allow the patient to select a disease to manage with the mobile application 308a, and the GUI 402b may adjust according to the selected disease, such as in what data is displayed, what goals are displayed, a color theme associated with the disease, and so forth.

In one embodiment, the mobile application 308a may be tailored for the patient, the third party, a non-medical user, and so forth. The tailoring may be the same for different users, or the tailoring may be different for different users. For example, a first instance of the mobile application 308a may be tailored for use by the patient and a second instance of the mobile application 308a may be tailored for use by a healthcare provider such as a nurse, doctor, practice manager, and so forth. In another example, a first instance of the mobile application 308a may be tailored for use by the patient and a second instance of the mobile application 308a may be tailored for use by a third party. The third-party may, for example, be a friend of the patient, a family member of the patient, or a care provider of the patient. The first instance of the mobile application 308a may display detailed personal information about the patient such as the patient's demographic information, the patient's vitals, the patient's goals and/or progress towards those goals, the patient's medications, the patient's medical history, information about the patient's medical provider, information about the patient's medical insurer, and so forth. The second instance of the mobile application 308a may display limited information about the patient. For example, the second instance of the mobile application 308a may display some of the patient's live vitals such as the patient's heart rate, the patient's electrocardiograph, the patient's glucose levels, the patient's hydration level, and so forth. The second instance of the mobile application 308a may display the patient's goals and/or progress towards those goals. In one embodiment, the patient may select via the first instance of the mobile application 308a what information is visible via the second instance of the mobile application 308a, up to and including all information available to the patient via the first instance of the mobile application 308a.

The modules may include programming and/or instructions for receiving inputs from the user via the GUI 402b and/or programming and/or instructions for generating outputs. The outputs may be displayed to the user via the GUI 402b, stored in memory of the user device 308, and/or sent from the user device 308 to another device such as the cloud-based server 306. The outputs may correspond to the inputs received from the user and/or the outputs may correspond to data received by the user device 308 from another device such as the cloud-based server 306. For example, the user may input information into one of the modules via the GUI 402b. The module may cause the information to be stored in the memory of the user device 308. The module may additionally and/or alternatively cause the information to be communicated to another device such as the cloud-based server 306. The module may additionally and/or alternatively cause the information to be displayed to the user. In another example, the user device 308 may receive information from another device such as the cloud-based server. The programming and/or instructions of the module may cause the information to be stored in the memory of the user device. The programming and/or instructions of the module may cause the information to be displayed via the GUI 402b to the user. The information may prompt an input from the user.

The GUI 402b may show a display generated by, for example, a processing device of the user device 308. The display may be tailored to show particular information for a particular user and/or type of user. In various embodiments, the cloud-based server 306 may include a wide array of information that may be useful to a variety of different users. However, not all the information may be useful and/or of interest to all the different users. Thus, the display may be tailored for the particular user to include information relevant to the particular user and/or to exclude information irrelevant to the particular user. For example, the cloud-based server 306 may store information about insurance costs associated with an individual and a medical chart associated with the individual. A display tailored for an insurance provider user may include the insurance costs and may exclude the medical chart. A display tailored for a healthcare provider may include the medical chart and may exclude the insurance costs.

The rewards module 404a may record the user's goals and/or track the user's progress towards the goals. The goals may be health-related goals. For example, the goals may include an exercise goal, a sleep goal, a blood glucose goal, a stress level goal, and so forth. The exercise goal may include exercising for a certain amount of time, exercising a certain number of times, having a heart rate over a certain level, and so forth. The sleep goal may include sleeping for a certain amount of time, achieving a certain amount of rapid eye movement (REM) sleep, and so forth. The blood glucose goal may include regular glucose measurement with a glucometer, wearing the wearable device 100 for a number of days in a row, and so forth. The blood glucose goal may include decreasing the user's fasting hemoglobin $A_{1c}$ ($A_{1c}$) level, decreasing a range of variation of the user's blood glucose level, and so forth. The stress level goal may include decreasing the user's average resting heart rate, decreasing the user's average resting blood pressure, and so forth. In an embodiment, the goal may be associated with an insurance provider. For example, the goal may relate to decreasing a cost of disease management by the insurance provider, such as by decreasing the patient's $A_{1c}$ level. A decreased $A_{1c}$ level may lead to decreased costs for the insurance provider, such as by decreasing doctor or hospital visits and/or decreasing payment for measurement supplies, medicine, and/or insulin supplies. The rewards module 404a may include programming and/or instructions for awarding one or more rewards as the user records progress towards the user's goals. The rewards may include points. The points may be added as the user progresses towards the goals and/or may be removed as the user digresses from the goals. In an embodiment, the user may redeem the points, such as for a gift card, a rebate, a prize, and so forth.

The history module 404b may include programming and/or instructions to store and/or display past and/or present data regarding one or more physiological characteristics of the user. The past and/or present data may include a graph, a table, a list, a current value, a past value, a maximum value, a minimum value, an average value, an optimal value, an amount of time within a particular and/or specified range, a coefficient of variation, information about trends in the data, a rate of change of the data, and so forth. For example, the past and/or present data may include a graph of physiological characteristic measurements indexed to a time stamp and/or indexed over a time interval. The physiological characteristics may include a heart rate, a blood pressure level, a hydration condition, a blood glucose level, and so forth. The blood glucose level may include a distinction between an invasively measured blood glucose level and a non-invasively measured blood glucose level. In one embodiment, the history module 404b may be programmed to display a graph showing continuous blood glucose measurements taken non-invasively from the user. The blood glucose measurements may be taken by the wearable device and communicated to the user device 308 via the cloud-based server 306.

The messages module 404c may include programming and/or instructions to display a message, a message notification, a message drafting interface, a journal interface, and so forth. The message may include a message from another user of another instance of the user device 308 application. For example, the message may be from a customer service agent using the point of care engagement center application 308c. In another example, the message may be from a family member, friend, and/or acquaintance with whom the patient shares health information. The family member, friend, and/or acquaintance may have access to a separate instance or the same instance of the user device 308 application than the patient. The message may be from a health care provider using the medical practitioner application 308d, and so forth. The message may be from an insurance provider using the insurance provider portal 308e. The message may include an automated message sent by an entity such as a healthcare provider company, a health insurance company, and so forth. The message notification may include a new message notification, an unread message notification, and so forth. The messages module 404c may include programming and/or instructions to receive input from the user and/or generate a message based on the user input. The message may be sent via the mobile application 308a to another instance of the user device 308 application. The message may include an email message, a text message, an internet message, and so forth. The message drafting interface may accept the user input to generate the message based on the user input.

The devices module 404d may include a list of one or more measurement devices that may be managed by the user via the mobile application 308a and/or which may interface with the user device 308. The measurement devices may include physiological characteristic measurement devices such as the peripheral measurement device(s) 304, the invasive analyte measurement device 302, the wearable device 100, and so forth. The devices module 404d may include programming and/or instructions which may correlate measurement data received by the user device 308 with a corresponding measurement device. The programming and/or instructions may include assigning an identifying tag to the corresponding measurement device, searching received measurement data for the identifying tag, and/or categorizing the received measurement data with the corresponding measurement device.

The condition management module 404e may include a list of health conditions that may be managed by the user via the mobile application 308a. The health conditions may be conditions of the user or of others associated with the user. For example, the user may manage the user's hydration via the mobile application 308a and may monitor the glucose levels of another person, such as the user's child, via the mobile application 308a. Selecting a condition in the condition management module 404e may enable a display to be generated on the GUI 402b which may include information tailored to the condition selected and the person for whom the condition is being managed. For example, the user may wish to see the last time the user's child performed a finger-stick glucose measurement. The user may select a diabetes condition icon in the condition management module 404e. The mobile application 308a may load a display and information corresponding to the child's glucose measurements. In an embodiment, a user may monitor the same condition for two or more people. For example, the user may monitor the user's hydration level and a hydration level of the user's child. Selecting a hydration icon in the condition management module 404e may cause a pop-up window to be generated which may prompt the user to select the person for whom the user wishes to see hydration information.

The menu module 404f may include programming and/or instructions that may display to the user a list of the modules associated with the mobile application 308a. The modules may include, the rewards module 404a, the history module 404b, the messages module 404c, the devices module 404d, a profile module, an appointment module, a share module, a healthcare provider finder module, and so forth. The user may select a module via the menu module 404f. The menu module 404f may include programming and/or instructions which may redirect the user in the mobile application 308a to the selected module. In an embodiment, the user may select the profile module in the menu module 404f. The profile module may be displayed to the user via the GUI 402b. The user may edit the profile module. The profile module may include demographic and/or identifying information about the user. The profile module may include an identifier that may identify a type of user the user is. For example, the user may include a patient, a healthcare provider, a third party granted access to the patient's health information, and so forth.

Figure 4B:
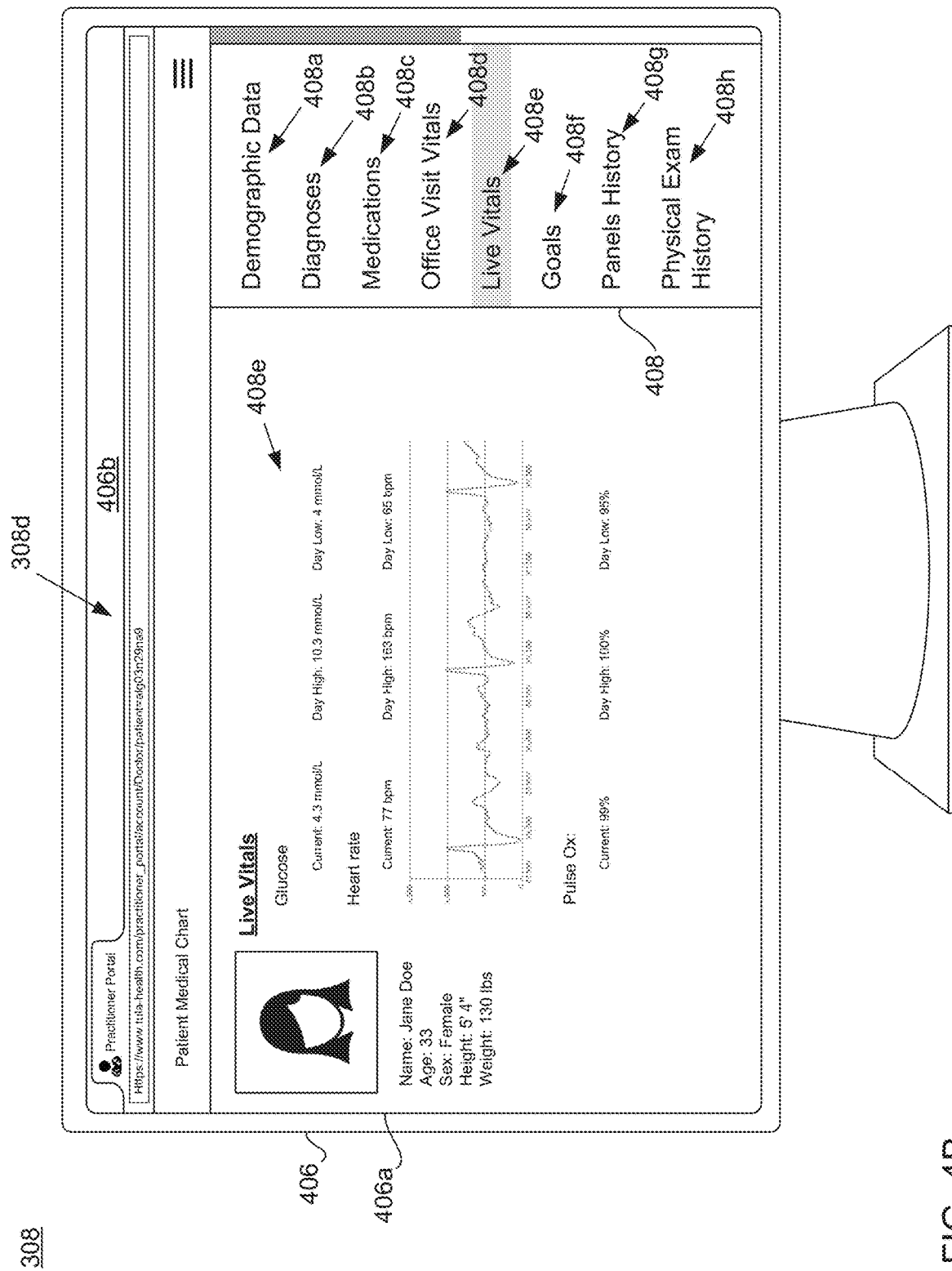
FIG. 4B illustrates the user device described regarding FIGS. 3A-C as a personal computer running a web browser displaying a medical practitioner application, according to an embodiment.

FIG. 4B illustrates the user device 308 as a personal computer 406 running a web browser 406b which may display the medical practitioner application 308d, according to an embodiment. Some of the features in FIG. 4B are the same as or similar to some of the features in FIGS. 1A-4A as noted by same and/or similar reference characters, unless expressly described otherwise. Additionally, reference may be made to features shown in any of FIGS. 1A-4A and not shown in FIG. 4B. The personal computer 406 may include a screen 406a displaying the web browser 406b. Via the web browser 406b, the medical practitioner application 308d may display information to the user and may accept input from the user. The information may be displayed to the user via one or more modules. The modules may include at least some of the same modules which may be displayed via the mobile application 308a. The modules may include a patient medical chart 408. The patient medical chart 408 may include patient demographics 408a, patient diagnoses 408b, patient medications 408c, office visit vitals 408d, patient live vitals 408e, patient health goals 408f, patient blood panels history 408g, patient physical exam history 408h, and so forth.

The patient demographics 408a may include information about the patient such as the patient's name, age, gender, ethnicity, address, contact information, family information, and so forth. The patient diagnoses 408b may include one or more diseases the patient has been diagnosed with such as hypertension, type 2 diabetes, heart disease, and so forth. The patient medications 408c may include past and/or present medications prescribed to the patient. The office visit vitals 408d may include vitals measurements taken at a doctor's office visit by the patient, such as the patient's weight, height, blood pressure, temperature, pulse, $A_{1c}$, glucose level, hydration level, arrhythmia, and so forth. The patient live vitals 408e may include vitals of the patient being continuously monitored such as a heart rate of the patient, a blood oxygen content of the patient, a blood glucose level of the patient, an estimated $A_{1c}$ of the patient, a hydration level of the patient, and so forth. The patient health goals 408f may be similar to the goals discussed above regarding the rewards module 404a. The patient blood panels history 408g may include blood panel results for the patient. The patient physical exam history 408h may include the patient's weight, height, observation of the patient's skin coloration, lungs, other organs, and so forth.

Using the web browser 406b displayed on the personal computer 406, the user may navigate to a website. The website may display information to the user which may allow the user to select an application. In an embodiment, the application may include the user portal 308b, the point of care engagement center application 308c, the medical practitioner application 308d, and/or the insurance provider portal 308e. In one embodiment, the user may log in to the website. The website may recognize the user as a patient, a healthcare provider such as a medical practitioner, a point of care engagement center agent, a health insurer, and so forth. The website may recognize the user by login credentials of the user. The web browser may load an instance of the health information application based on the login credentials. For example, the login credentials may indicate the user is the patient, and the web browser may load the user portal 308b. The login credentials may indicate the user is a point of care engagement center agent, and the web browser may load the point of care engagement center application 308c. The login credentials may indicate the user is a medical practitioner and the web browser may load the medical practitioner application 308d. The login credentials may indicate the user is an insurance provider and the web browser may load the insurance provider portal 308e.

Figure 4C:
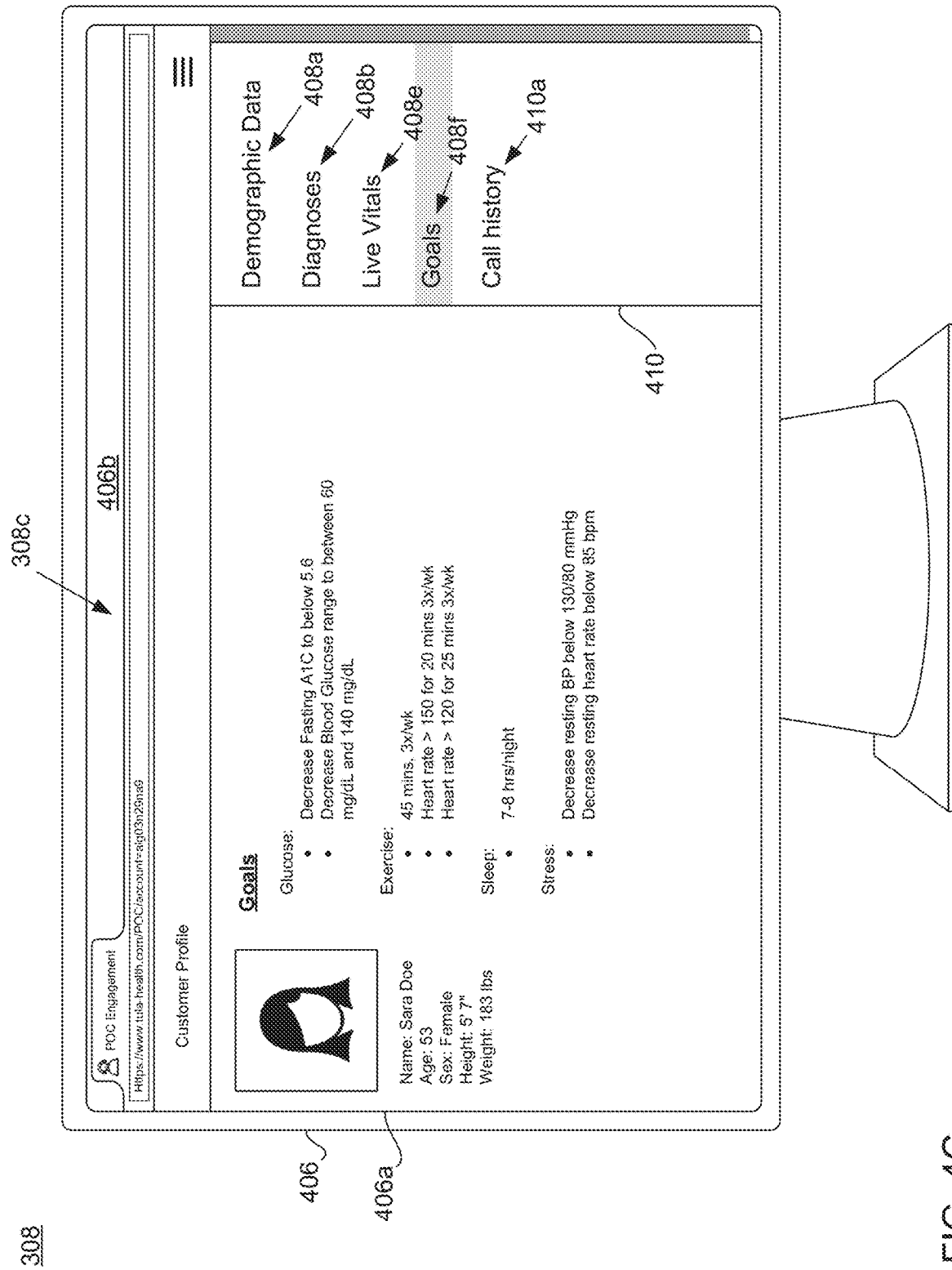
FIG. 4C illustrates the user device described regarding FIGS. 3A-C as a personal computer running a web browser displaying a point-of-care engagement center application, according to an embodiment.

FIG. 4C illustrates the user device 308 as the personal computer 406 running the web browser 406b which may display the point of care engagement center application 308c, according to an embodiment. Some of the features in FIG. 4C are the same as or similar to some of the features in FIGS. 1A-4B as noted by same and/or similar reference characters, unless expressly described otherwise. Additionally, reference may be made to features shown in any of FIGS. 1A-4B and not shown in FIG. 4C. The personal computer 406 may display the point of care engagement center application 308c on the screen 406a via the web browser 406b. Via the web browser 406b, the point of care engagement center application 308c may display information to the user and may accept input from the user. The information may be displayed to the user via one or more modules. The modules may include at least some of the same modules which may be displayed via the mobile application 308a and/or the medical practitioner application 308d. The modules may include a patient health overview 410. The patient health overview 410 may include the patient demographics 408a, the patient diagnoses 408b, the patient live vitals 408e, patient health goals 408f, a record of calls 410a between the patient and the point of care engagement center, and so forth. The patient health overview 410 may be tailored for the point of care engagement center application 308c, where the patient health overview 410 may provide information to employees of the point of care engagement center that may enable the employees to consult with the patient regarding the patient's health outcomes.

The insurance provider portal 308e may display information tailored to services provided by the insurance provider to the patient and objectives of the insurance provider related to the patient's health. For example, the insurance provider portal 308e may include information about the frequency of visits by the patient to the doctor or hospital, information about medications the patient takes, and detailed information about costs associated with the patient's health care. The insurance provider portal 308e may include a module that may allow the insurance provider to set health care cost goals for the patient and communicate with the patient about those goals. The insurance provider portal 308e may include data about changes over time in the cost of health care for the patient. The insurance provider portal 308e may include profitability data associated with the patient and/or with particular healthcare providers. For example, the insurance provider portal 308e may display information about the lowest-cost providers. The insurance provider portal 308e may include a module that may recommend providers to the patient based on costs and/or health outcomes of other patients that use the providers.

Figure 5A:
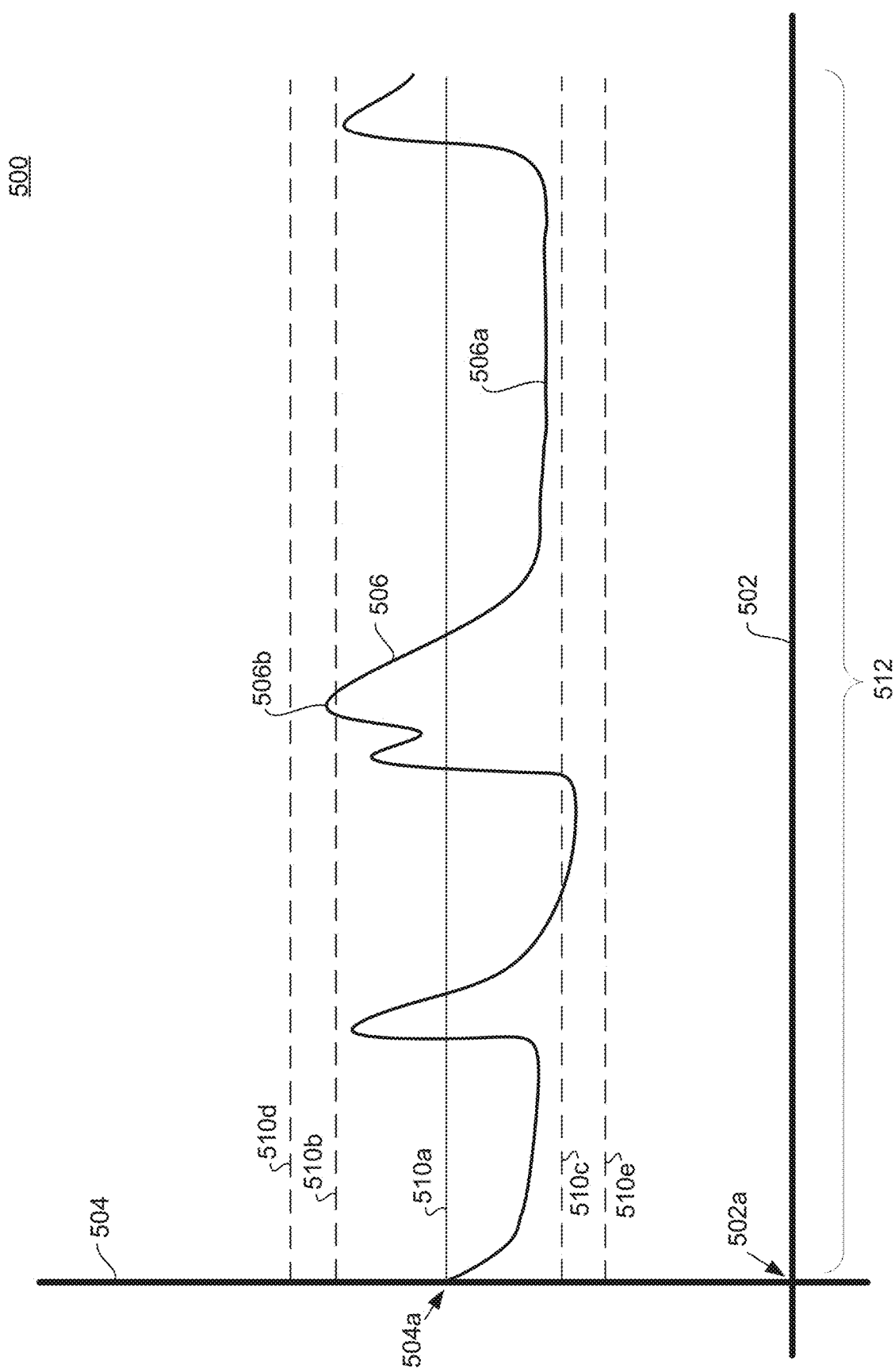
FIG. 5A illustrates a graph of analyte measurements taken continuously from a user over a period of time, according to an embodiment.

FIG. 5A illustrates a graph 500 of analyte measurements taken continuously from a user over a period of time period 512, according to an embodiment. Some of the features in FIG. 5A are the same as or similar to some of the features in FIGS. 1A-4C as noted by same and/or similar reference characters, unless expressly described otherwise. Additionally, reference may be made to features shown in any of FIGS. 1A-4C and not shown in FIG. 5A. The analyte measurements may be taken by a continuous measurement device, such as the wearable device 100. The first sensor 112 and/or the second sensor 114 may take continuous measurements of physiological characteristics of a patient wearing the wearable device 100. The measurements may be processed as described herein to determine a health status of the patient. In one embodiment, the continuous measurements may relate to a blood glucose level of the patient. Indeed, the graph 500 may show changes in the patient's blood glucose levels over a period of time.

The graph 500 may include a time axis 502, an analyte level axis 504, and a curve 506 generated by analyte level measurements taken at particular points in time. An initial analyte level 504a may be measured at a beginning time 502a. The curve 506 may include local valleys 506a and local peaks 506b. In various embodiments, the graph 500 may be displayed to a user such as the patient, a healthcare provider, an insurance provider, another third party, and so forth. The graph 500 may accordingly include boundary indicators based on an initial measurement line 510a. The boundary indicators may delineate a range of analyte levels from the initial analyte level 504a that may be acceptable and/or healthy for the patient. The boundary indicators may include an upper warning line 510b, a lower warning line 510c, an upper danger line 510d, and a lower danger line 510e.

The time axis 502 may be referenced to an absolute time, such as a clock and/or calendar time. The time axis 502 may be referenced to a relative time. For example, the beginning time 502a may include a clock time, such as 8:00 am, or a relative time of zero minutes. Subsequent times along the time axis 502 may be referenced from the beginning time 502a. The time axis 502 may include intervals in seconds, minutes, hours, days, and so forth. Similarly, the analyte level axis 504 may reference an absolute analyte level with a minimum of zero analyte. The analyte level axis 504 may reference a relative analyte level. The relative analyte level may be set at zero for a starting analyte measurement level and may include positive and negative values corresponding to changes in the analyte level from the starting analyte measurement level. The starting analyte measurement level may include a safe analyte level and/or an initial analyte level. In one embodiment, the initial analyte level 504a may be set as a "zero" mark, the upper warning line 510b and the upper danger line 510d may represent positive changes from the initial analyte level 504a represented by positive values, and the lower warning line 510c and the lower danger line 510e may represent negative changes from the initial analyte level 504a represented by negative values.

The beginning time 502a may start when a first measurement is taken. The first measurement may determine an absolute value for the initial analyte level 504a. The initial measurement line 510a may be set to the initial analyte level 504a. The first measurement may be taken by the wearable device 100. The first measurement may be taken by an invasive measurement device such as the invasive analyte measurement device 302. In an embodiment, the first measurement may include a glucose measurement taken by an invasive glucometer using blood drawn by, for example, a finger prick. Subsequent measurements that may fill out the curve 506 for a remainder of the time period 510 after the beginning time 502a may be taken by a miniaturized spectrometer and/or a bioimpedance sensor embedded in the wearable device 100. The miniaturized spectrometer may be aligned with a blood vessel such as a vein or artery. A light source embedded in the wearable device 100 may shine light through the blood vessel. The miniaturized spectrometer may determine an amount of glucose in the blood vessel based on relative intensities of constituent wavelengths of the light that pass through and/or reflect off of blood within the blood vessel.

In various embodiments, the curve 506 may include a sequence of discreet measurements conjoined by a line to form a continuous representation of the discreet measurements. The discreet measurements may be demarked by one or more indicators, such as symbols, which may indicate a precise time and level for the measurement. The indicators may be conjoined by the line. In various embodiments, the curve 506 may include the indicators and may omit the line conjoining the indicators. The curve 506 may be smoothed by a smoothing algorithm. In various embodiments, the curve 506 may include continuous measurements represented by a continuous line. The curve 506 may be displayed to a user, such as the patient via the wearable device 100, a healthcare provider via the user device 308, and so forth. The curve 506 may be displayed as the curve 506 is being generated. For example, the time period 512 may include a fixed time period, such as a current day, and hour, a week, a month, and so on. The graph 500 may display the time period 512 and may show analyte measurements as the analyte measurements are taken, indexed to the time during the day the measurements are taken. A user may view the graph at 8:00 am and see measurements taken between 12:00 am and 8:00 am. The user may review the graph at 10:00 am and see measurements taken between 12:00 am and 10:00 am, and so on. Accordingly, the curve 506 may be updated in real-time.

In various embodiments, the upper danger line 510d may indicate a dangerously high amount of analyte in the patient at and/or over which the patient is more likely than not to experience adverse and/or severe symptoms due to the patient's analyte level being too high. In various embodiments, the upper danger line 510d may indicate a dangerous difference in analyte level above the initial analyte level 504a. The dangerously high amount of analyte may include an absolute level of the analyte based on data gathered from a population of individuals. The dangerously high amount of analyte may include an absolute level of the analyte based on data gathered from the patient on the amount of analyte at and/or above which the patient experiences adverse and/or severe symptoms. The adverse and/or severe symptoms may correspond to a condition related to the analyte. For example, in embodiments where the analyte is glucose, glucose levels at and/or above the upper danger line 510d may indicate the patient is hyperglycemic. The adverse and/or severe symptoms may include dizziness, nausea, light-headedness, profuse sweating, irregular heartbeat, loss of consciousness, and so forth. The patient may experience symptoms of hyperglycemia at and/or above the upper danger line 510d.

In various embodiments, the lower danger line 510e may indicate a dangerously low amount of analyte in the patient at and/or below which the patient is more likely than not to experience adverse and/or severe symptoms due to the patient's analyte level being too low. In various embodiments, the lower danger line 510e may indicate a dangerous difference in analyte level below the initial analyte level 504a. The dangerously low amount of analyte may include an absolute level of the analyte based on data gathered from a population of individuals. The dangerously low amount of analyte may include an absolute level of the analyte based on data gathered from the patient on the amount of analyte below the initial analyte level 504a at which the patient experiences adverse and/or severe symptoms. The adverse and/or severe symptoms may correspond to a condition related to the analyte. For example, in embodiments where the analyte is glucose, glucose levels at and/or below the lower danger line 510e may indicate the patient is hypoglycemic. The patient may experience symptoms of hypoglycemia at and/or below the lower danger line 510e.

In various embodiments, the upper danger line 510d and the lower danger line 510e may correspond to statistically abnormal amounts of the analyte. In various embodiments, the upper danger line 510d and the lower danger line 510e may correspond to statistically abnormal variations in the amount of analyte from the initial analyte level 504a. The statistically abnormal amounts of the analyte and/or the statistically abnormal variations in the amount of analyte from the initial analyte level 504a may be based on data taken from a population of individuals and/or from data taken from the patient. The statistically abnormal amounts of the analyte and/or the statistically abnormal variations in the amount of analyte from the initial analyte level 504a may correspond to a number of standard deviations from the initial analyte level 504a. For example, the statistically abnormal amounts of the analyte and/or the statistically abnormal variations in the amount of analyte from the initial analyte level 504a may define a range of amounts of analyte above and below the initial analyte level 504a at or within two standard deviations from the initial analyte level 504a.

The upper warning line 510b may indicate an amount of analyte in the patient within a threshold of the dangerously high amount of analyte. The threshold may be within a certain percentage of the dangerously high amount of analyte indicated by the upper danger line 510d. The threshold may be within an absolute amount of the dangerously high amount of analyte. The threshold may be within a percentage of the dangerously high amount of analyte. The percentage may be based on a difference between the initial analyte level 504a and the dangerously high amount of analyte. The upper warning line 510b may indicate an amount of analyte in the patient at and/or above which the patient is more likely than not to experience minor adverse symptoms. The minor adverse symptoms may correspond to a condition related to the analyte. For example, the analyte may include blood glucose. The minor adverse symptoms may include increased resting heart rate, increased resting blood pressure, sweating, excessive thirst, and so forth. The upper warning line 510b may indicate the patient is close enough to experiencing hyperglycemia to take mitigating steps to avoid hyperglycemia. The mitigating steps may include taking a shot of insulin.

The lower warning line 510c may indicate an amount of analyte in the patient within a threshold of the dangerously low amount of analyte. The threshold may be within a certain percentage of the dangerously low amount of analyte indicated by the lower danger line 510e. The threshold may be within an absolute amount of the dangerously low amount of analyte. The threshold may be within a percentage of the dangerously low amount of analyte. The percentage may be based on a difference between the initial analyte level 504a and the dangerously low amount of analyte. The lower warning line 510c may indicate an amount of analyte in the patient at and/or above which the patient is more likely than not to experience minor adverse symptoms. The minor adverse symptoms may correspond to a condition related to the analyte. For example, the analyte may include blood glucose. The lower warning line 510c may indicate the patient is close enough to experiencing hypoglycemia to take mitigating steps to avoid hypoglycemia. The mitigating steps may include drinking a sugary beverage.

In various embodiments, the upper warning line 510b and the lower warning line 510c may correspond to statistically significant amounts of the analyte. In various embodiments, the upper danger line 510d and the lower danger line 510e may correspond to statistically significant variations in the amount of analyte from the initial analyte level 504a. The statistically significant amounts of the analyte and/or the statistically significant variations in the amount of analyte from the initial analyte level 504a may be based on data taken from a population of individuals and/or from data taken from the patient. The statistically significant amounts of the analyte and/or the statistically significant variations in the amount of analyte from the initial analyte level 504a may correspond to a number of standard deviations from the initial analyte level 504a. For example, the statistically significant amounts of the analyte and/or the statistically significant variations in the amount of analyte from the initial analyte level 504a may define a range of amounts of analyte above and below the initial analyte level 504a at or within one standard deviation from the initial analyte level 504a.

The curve 506 may represent continuous measurements of the patient's analyte levels during the time period 512. The continuous measurements may be monitored and/or compared to the dangerously high amount of analyte and the dangerously low amount of analyte. For example, the processor of the wearable device 100 may be programmed to generate a warning as the patient's analyte level reaches and/or exceeds the upper warning line 510b, and/or as the patient's analyte level reaches and/or dips below the lower warning line 510c. The warning may include an audible and/or visual signal communicated via a user interface of the wearable device 100. The warning may include a signal communicated to another device such as the cloud-based server 306 and/or the user device 308.

The cloud-based server 306 may store the warning and/or use the warning in an analytics process. An individual patient's tolerance ranges for a given analyte, such as glucose, may differ from statistically average tolerance ranges for a population. A tolerance range may include a range of analyte levels outside of which the patient is more likely than not to experience adverse symptoms. The data analytics application 306e may determine the individual patient's tolerance ranges by correlating the patient's analyte levels with other concurrent physiological characteristics of the patient. For example, the data analytics application 306e may correlate the patient's analyte levels with concurrent heart rate data and concurrent sweat rate data. The data analytics application 306e may determine a statistical correlation between the analyte levels and the onset of adverse symptoms. The data analytics application 306e may determine a statistical correlation between the analyte levels and relief from the adverse symptoms. In a specific embodiment, the data analytics application 306e may compare blood glucose data to heart rate data, blood pressure data, and/or sweat rate data. The data analytics application 306e may correlate a sudden drop in blood pressure and a sudden increase in sweating with a blood glucose level. The data analytics application 306e may set the measured blood glucose level corresponding to the sudden drop in blood pressure and sudden increase in sweating as a danger level and may set a warning level between a safe level and the danger level. The warning level may include a percentage of a difference between the safe level and the danger level, such as 75 percent, 80 percent, 85 percent, 90 percent, and so forth. The safe level may be based on a fasting blood glucose level and/or on a postprandial blood glucose level for the patient and/or for a population of which the patient is a member.

The cloud-based server 306 may store information regarding tolerable rates of change of the patient's analyte levels. For example, a too-rapid drop in blood glucose level may indicate an imminent onset of severe hypoglycemic symptoms, including shock, severe nausea, loss of consciousness, and so forth. The cloud-based server 306 may include alerts associated with maximum and/or minimum rates of change of the patient's analyte levels and generate alerts when the patient's current rate of change in the analyte exceeds the maximum or minimum threshold. For example, the patient may experience a rapid increase in blood alcohol content, and the patient's blood alcohol content may sustain at a high level and/or continue increasing over time. The cloud-based server may generate an alert that the patient is consuming too much alcohol. The alert may be transmitted to another user associated with the patient and/or to the patient, such as via the wearable device 100, to alert the patient and/or the other user that the patient's alcohol consumption is too high. This may help prevent alcohol poisoning and/or another alcohol-related injury.

A shape of the curve 506 may vary depending on the type of analyte measured to generate the analyte levels. The shape of the curve 506 may indicate a behavior of the patient corresponding to the analyte. In various embodiments, the analyte may be blood glucose. The shape of the curve 506 may include sharp increases corresponding with mealtimes, followed by less sharp decreases corresponding to metabolizing of the blood glucose. The shape of the curve 506 may include local valleys 506a corresponding to periods of fasting and sharp local peaks 506b corresponding to mealtimes. In various embodiments, the analyte may be blood cells, electrolytes, serum albumin, immunoglobulins, proteins, blood-clotting factors, and so forth. The shape of curves corresponding to these analytes, respectively, may vary according to how the analytes individually vary with time.

In an embodiment, the information displayed in the graph 500, such as the initial measurement line 510a, the upper warning line 510b, the lower warning line 510c, the upper danger line 510d, and/or the lower danger line 510e may be stored in a device and compared to real-time analyte measurements taken from the patient. The device may include the wearable device 100, the invasive analyte measurement device 302, the cloud-based server 306, and/or the user device 308. As a real-time analyte measurement exceeds a warning level and/or a danger level, an alert may be communicated via the device. The alert may be communicated via the wearable device 100 and/or the invasive analyte measurement device 302. The cloud-based server 306 may generate the alert and communicate the alert to the wearable device 100, the invasive analyte measurement device 302, and/or the user device 308. The alert may be generated by the user device 308 and/or communicated to the user and/or the patient via the user device 308. The user device 308 may communicate the alert to the cloud-based server 306, the wearable device 100, and/or the invasive analyte measurement device 302.

In one example, the wearable device 100 may determine a real-time measurement exceeds a danger level. The wearable device 100 may communicate an alert to the patient and send the alert to the user device 308 via the cloud-based server 306. For example, the alert communicated to the patient may instruct the patient to take an analyte measurement such as an invasive glucose measurement (i.e. a finger prick measurement). A healthcare provider may view the alert on the user device 308, such as through one of the applications 308a-d. The alert may prompt the user to attempt to contact the patient to determine the patient's health status. For example, the alert may prompt the user to call the patient or contact the patient via a message on the wearable device 100. Based on an urgency of the alert, such as a warning alert or a danger alert, the user may be prompted to contact emergency personnel if the user is unable to contact the patient.

Figure 5B:
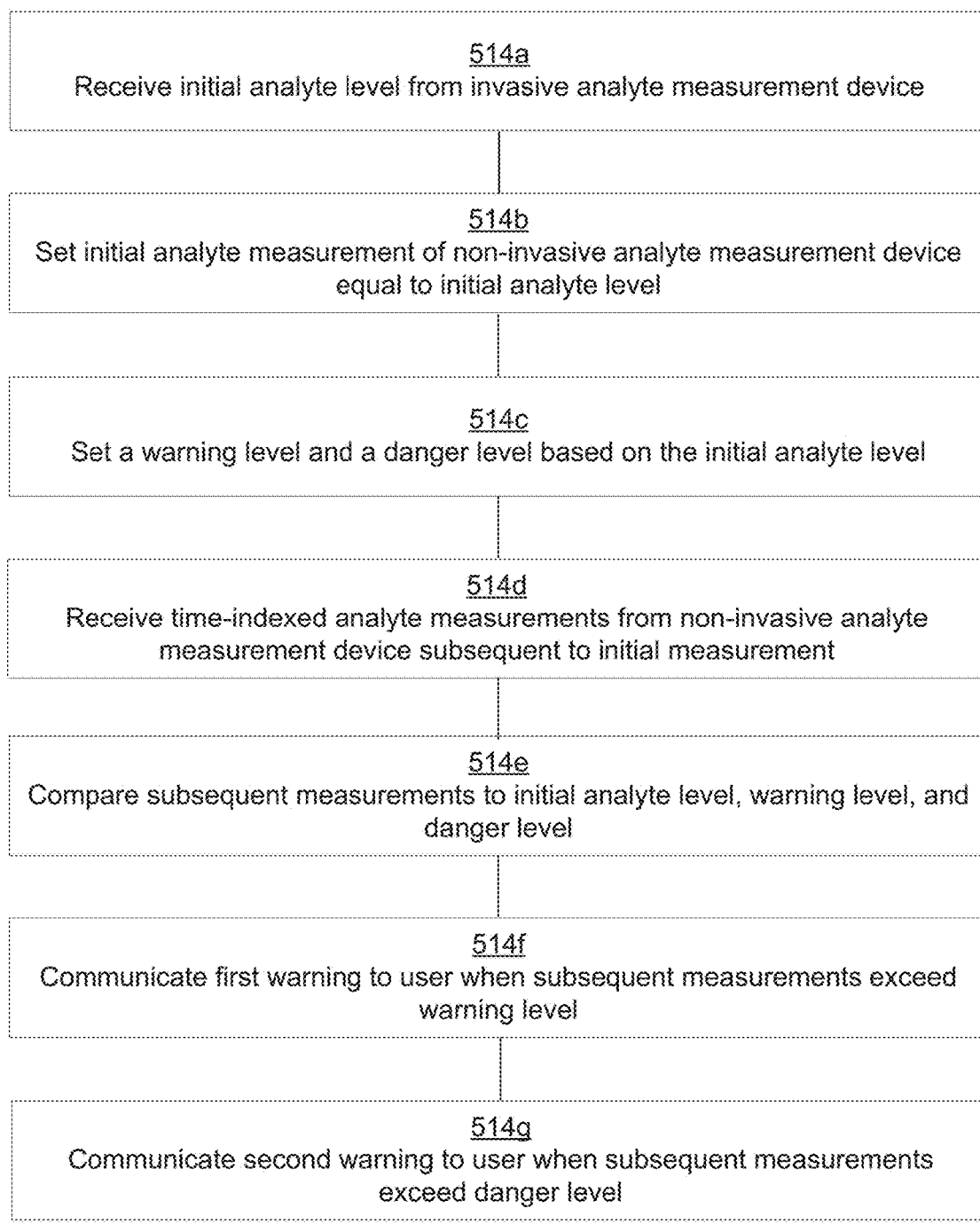
FIG. 5B illustrates a method of taking time-indexed analyte measurements and communicating warnings to a user when the measurements exceed set levels, according to an embodiment.

FIG. 5B illustrates a method 514 of taking time-indexed analyte measurements and communicating warnings to a user when the measurements exceed set levels, according to an embodiment. Some of the features in FIG. 5B are the same as or similar to some of the features in FIGS. 1A-5A as noted by same and/or similar reference characters, unless expressly described otherwise. Additionally, reference may be made to features shown in any of FIGS. 1A-5A and not shown in FIG. 5B. In various embodiments, the method 514 may be performed on one device such as the wearable device 100, the invasive analyte measurement device 302, the cloud-based server 306, the user device 308, and so forth. In various embodiments, elements of the method 514 may be performed on separate devices, where the devices form a health device network.

The method 514 may include receiving an initial analyte level from an invasive analyte measurement device such as the invasive analyte measurement device 302 (block 514a). In an embodiment, the analyte may be glucose and the invasive analyte measurement device may include an invasive glucometer. The method 514 may include setting an initial analyte measurement of a non-invasive analyte measurement device equal to the initial analyte level (block 514b). In an embodiment, the non-invasive analyte measurement device may include the wearable device 100. The method 514 may include setting a warning level and a danger level based on the initial analyte level and/or based on a coefficient of variation of the patient's analyte levels. (block 514c). The warning level may include the upper warning line 510b and/or the lower warning line 510c. The danger level may include the upper danger line 510d and/or the lower danger line 510e. The warning level and/or the danger level may be based on a statistical amount of expected change from a base analyte level, i.e. the coefficient of variation. The base analyte level may include, for example, a fasting glucose level. The coefficient of variation may be based on statistical data calculated from measurements taken over time from the patient. Accordingly, the coefficient of variation may be specific to the patient. In an embodiment, the danger level and/or the warning level may be determined based on a combination of the coefficient of variation and the initial analyte level.

The method 514 may include receiving time-indexed analyte measurements from the non-invasive analyte measurement device subsequent to the initial analyte measurement by the non-invasive analyte measurement device (block 514d). The time indexing may be relative to an initial time at which the initial analyte level was taken, where the initial time is a zero time. The time indexing may be relative to an absolute time such as a calendar time and/or a clock time. The method 514 may include comparing the subsequent measurement to the initial analyte level, the warning level, and/or the danger level (block 514e). The method 514 may include communicating a first warning to a user when a subsequent measurement exceeds the warning level (block 514f). For example, the first warning may be communicated when the subsequent measurement is higher than the upper warning line 510b or lower than the lower warning line 510c. The method 514 may include communicating a second warning to the user when the subsequent measurement exceeds the danger level (block 514g). For example, the second warning may be communicated when the subsequent measurement is higher than the upper danger line 510d or lower than the lower danger line 510e.

In an embodiment, the device may include the wearable device 100 and the user may include a patient wearing the wearable device 100 from whom the measurements may be taken. The wearable device 100 may generate the first warning and/or the second warning via the display device 104. The first warning and/or the second warning may include visual communication such as words, flashing lights, and colors. The first warning and/or the second warning may include audible communication such as a sound and/or tone. The first warning and/or the second warning may include tactile communication such as vibration. In an embodiment, the device may include the cloud-based server 306. The user may include the patient and/or a healthcare provider. The cloud-based server 306 may send the first warning and/or the second warning as an alert to the patient's mobile phone. The cloud-based server 306 may send the first warning and/or the second warning as an alert via the mobile application 308a, the user portal 308b, the point of care engagement center application 308c, and/or the medical practitioner application 308d.

Figure 6:
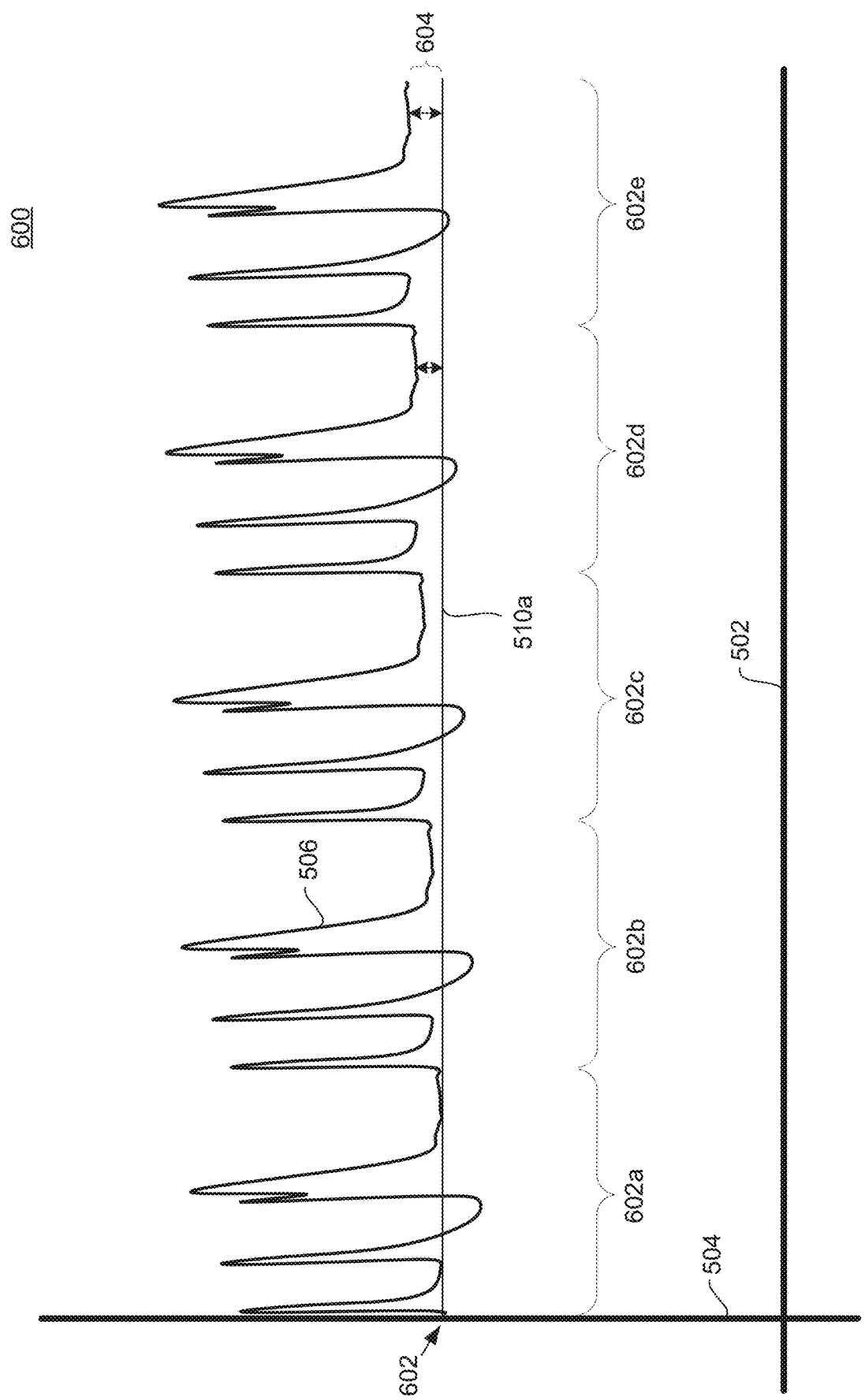
FIG. 6 illustrates a graph of analyte measurements taken over consecutive time periods and drifting from an initial reference, according to an embodiment.

FIG. 6 illustrates a graph 600 of analyte measurements taken over consecutive time periods 602a-e and drifting from an initial reference measurement 602, according to an embodiment. Some of the features in FIG. 6 are the same as or similar to some of the features in FIGS. 1A-5B as noted by same and/or similar reference characters, unless expressly described otherwise. Additionally, reference may be made to features shown in any of FIGS. 1A-5B and not shown in FIG. 6. The graph 600 includes the curve 506 referenced to the time axis 502 and the analyte level axis 504. The curve 506 includes measurements take over a first time period 602*a*, a second time period 602*b*, a third time period 602*c*, a fourth time period 602*d*, and a fifth time period 602*e*. Over the consecutive time periods 602*a-e*, the curve 506 includes a drift 604 from the initial reference measurement 602. The drift 604 may be indicated by a difference between the initial measurement line 510*a* and the curve 506 during the first time period 602*a* as compared with a difference between the initial measurement line 510*a* and the curve 506 during the fifth time period.

In various embodiments, the drift 604 may reflect a change in a range of measurements for the analyte in the patient. For example, the analyte may include glucose. The drift may indicate glucose is not being removed from the patient's blood efficiently and/or effectively and the patient's average blood glucose levels are rising. In various embodiments, the drift 604 may reflect a change in a physiological element related to the analyte being measured that affects the measurement of the analyte. For example, the analyte may include glucose and the physiological element may include water. The analyte may be measured by in vivo optical spectroscopy, such as by using the wearable device 100 with the first sensor 112 being a miniaturized spectrometer. Optical spectroscopy may yield a concentration of the glucose in the patient's blood as opposed to an absolute amount of glucose in the patient's blood. As a hydration condition of the patient changes, a concentration of glucose in the user's blood may change even as an absolute level of glucose in the user's blood may remain consistent within a pattern of variation for the level of glucose. The drift 604 may therefore indicate a change in the patient's hydration condition. In embodiments where optical spectroscopy is performed for analyte measurement, the drift 604 may indicate a change in an amount of interference in the patient's blood by another analyte than the analyte of interest. The other analyte may absorb the same wavelengths of light as absorbed by the analyte of interest. For example, as the patient's blood contains more water, which may absorb the same wavelengths of light as glucose in the blood.

In various embodiments, the drift 604 may be caused by a physiological element having a significantly longer change period than a change period for the analyte. For example, the analyte may be glucose and the physiological element may be water. Glucose in the patient's blood may change dramatically over a period of a few minutes as the patient eats. Water in the patient's blood may change dramatically over a period of hours as the patient becomes dehydrated, such as during an extended period of physical exertion where the patient sweats. The decrease in water in the patient's blood may result in an overall increase in a concentration of glucose in the patient's blood. A device that measures concentration may output a measurement that gives an appearance blood glucose is increasing even though it may actually be decreasing, maintaining at a level, or increasing slower than it appears to be increasing.

Figure 7A:
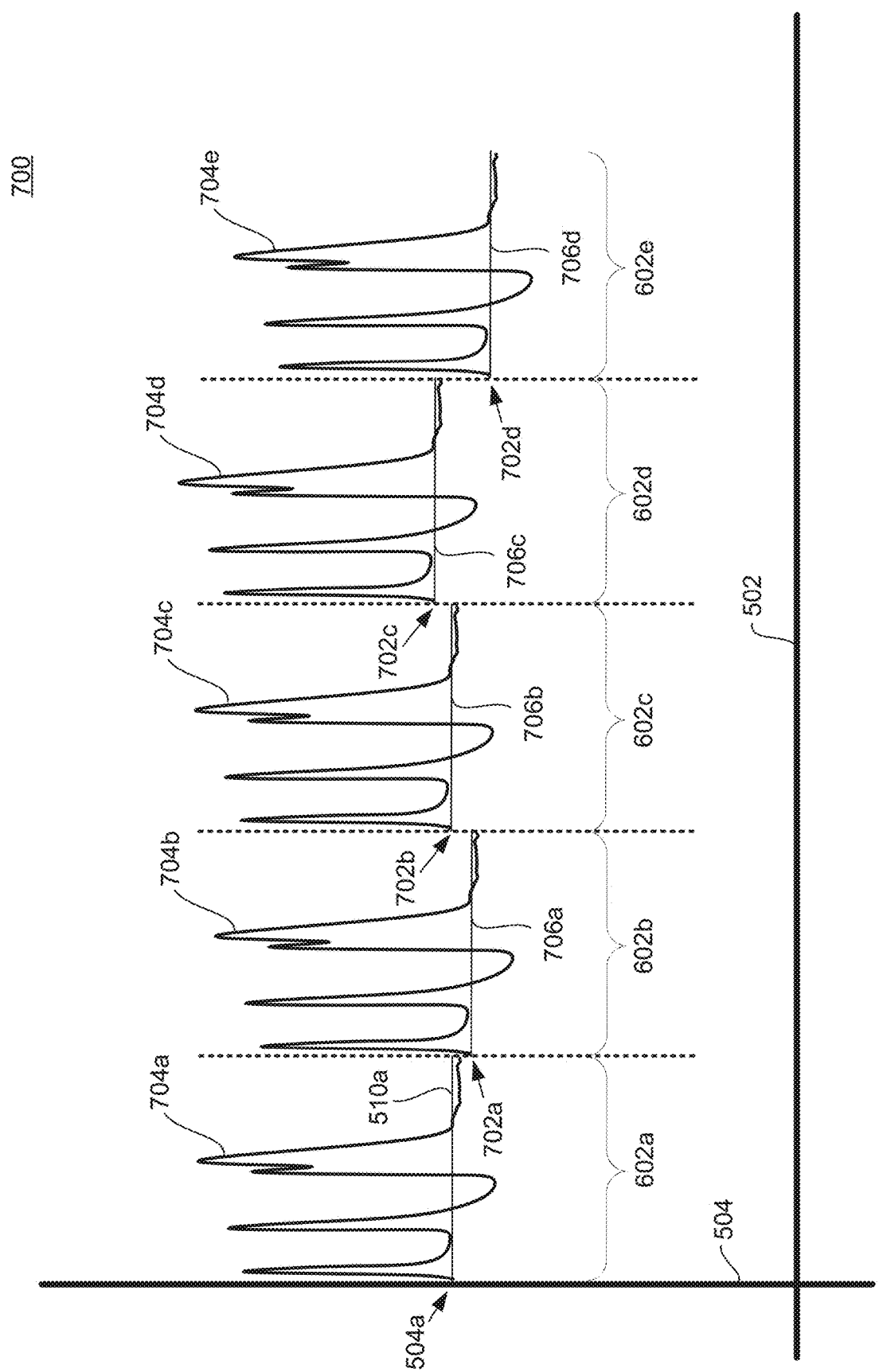
FIG. 7A illustrates a graph of analyte measurements taken over the consecutive time periods with indictors for the initial analyte level and subsequent validated and/or reinitialized analyte levels, according to an embodiment.

FIG. 7A illustrates a graph 700 of analyte measurements taken over the consecutive time periods 602*a-e* with indicators for the initial analyte level 504*a* and subsequent validated and/or reinitialized analyte levels 702*a-d*, according to an embodiment. Some of the features in FIG. 7A are the same as or similar to some of the features in FIGS. 1A-6 as noted by same and/or similar reference characters, unless expressly described otherwise. Additionally, reference may be made to features shown in any of FIGS. 1A-6 and not shown in FIG. 7A. A first analyte measurement curve 704*a* extends over the first time period 602*a*. A first measurement of the first analyte measurement curve 704*a* may be set equal to the initial analyte level 504*a*, and subsequent analyte measurements that fill out the first analyte measurement curve 704*a* may be referenced to the initial analyte level 504*a* as changes from the initial analyte level 504*a*. The initial measurement line 510*a* may provide a visual indication across the first time period 602*a* of the initial analyte level 504*a* and differences between subsequent measurements, as indicated by the first analyte measurement curve 704*a*, and the initial analyte level 504*a*.

In various embodiments, the initial analyte level 504*a* may be validated and/or reinitialized to identify and/or compensate for drift in the analyte measurements attributable to another physiological element that may skew the analyte measurements. The initial analyte level 504*a* may be validated at an end of the first time period 602*a*. For example, the first time period 602*a* may be 24 hours. At the end of 24 hours, the initial analyte level 504*a* may be validated. In an embodiment, the initial analyte level 504*a* may be set by a measurement taken by an invasive analyte measurement device, such as the invasive analyte measurement device 302. The subsequent analyte measurements that fill out the first analyte measurement curve 704*a* may be taken by a non-invasive analyte measurement device such as the wearable device 100. The initial analyte level 504*a* may be validated by a second measurement taken by the invasive analyte measurement device. The measurement taken by the invasive analyte measurement device may be less susceptible to skewing by the other physiological element than measurements taken by the non-invasive analyte measurement device. Accordingly, the second measurement by the invasive analyte measurement device may not reflect drift, such as the drift 604, that accrues over the first time period 602*a* in the first analyte measurement curve 704*a*.

The second measurement by the invasive analyte measurement device may yield a first validated and/or reinitialized analyte measurement level 702*a*. The first validated and/or reinitialized analyte measurement level 702*a* may be discontinuous with the first analyte measurement curve 704*a*. A time along the time axis 502 at which the second measurement by the invasive analyte measurement device is taken may demark an end of the first time period 602*a* and a beginning of a second time period 602*b*. The first validated and/or reinitialized analyte measurement level 702*a* may demark a starting analyte level against which non-invasive analyte measurements taken during the second time period 602*b* may be referenced. The non-invasive analyte measurements taken during the second time period 602*b* may be represented on the graph 700 by a second analyte measurement curve 704*b*. A first measurement of the second analyte measurement curve 704*b* may be set equal to the first validated and/or reinitialized analyte measurement level 702*a*. A first validated and/or reinitialized measurement line 706*a* may provide a visual indication across the second time period 602*b* of the first validated and/or reinitialized analyte measurement level 702*a*.

In various embodiments, the non-invasive analyte measurements may be validated and/or reinitialized periodically by invasive analyte measurements to identify and/or compensate for the drift. Accordingly, a third measurement by the invasive analyte measurement device may yield a second validated and/or reinitialized analyte measurement level 702*b*. A time along the time axis 502 at which the third measurement by the invasive analyte measurement device is taken may demark an end of the second time period 602*b* and a beginning of a third time period 602*c*. The second validated and/or reinitialized analyte measurement level 702*b* may demark a starting analyte level against which non-invasive analyte measurements taken during the third time period 602*c* may be referenced. The non-invasive analyte measurements taken during the third time period 602*c* may be represented on the graph 700 by a third analyte measurement curve 704*c*. A first measurement of the third analyte measurement curve 704*c* may be set equal to the second validated and/or reinitialized analyte measurement level 702*b*. A second validated and/or reinitialized measurement line 706*b* may provide a visual indication across the third time period 602*c* of the second validated and/or reinitialized analyte measurement level 702*b*.

Periodic validation and/or reinitialization may occur continuously. Accordingly, a fourth measurement by the invasive analyte measurement device may yield a third validated and/or reinitialized analyte measurement level 702*c*; a fifth measurement by the invasive analyte measurement device may yield a fourth validated and/or reinitialized analyte measurement level 702*d*; and so forth. The third validated and/or reinitialized analyte measurement level 702*c* may demark a starting analyte level against which non-invasive analyte measurements taken during a fourth time period 602*d* may be referenced; the fourth validated and/or reinitialized analyte measurement level 702*d* may demark a starting analyte level against which non-invasive analyte measurements taken during a fifth time period 602*e* may be referenced; and so forth. The non-invasive analyte measurements taken during the fourth time period 602*d* may be represented on the graph 700 by a fourth analyte measurement curve 704*d*; the non-invasive analyte measurements taken during the fourth time period 602*d* may be represented on the graph 700 by a fourth analyte measurement curve 704*d*; and so forth. A first measurement of the fourth analyte measurement curve 704*d* may be set equal to the third validated and/or reinitialized analyte measurement level 702*c*; a first measurement of the fifth analyte measurement curve 704*e* may be set equal to the fourth validated and/or reinitialized analyte measurement level 702*d*; and so forth. A third validated and/or reinitialized measurement line 706*c* may provide a visual indication across the fourth time period 602*d* of the third validated and/or reinitialized analyte measurement level 702*c*; a fourth validated and/or reinitialized measurement line 706*d* may provide a visual indication across the fifth time period 602*e* of the fourth validated and/or reinitialized analyte measurement level 702*d*; and so forth.

The validation and/or reinitialization of the analyte measurements (validation) may be distinguished from a calibration and/or baselining process. Calibration may generally refer to a process by which device settings are tuned to a particular standard. Baselining may generally refer to a process by which measurements are compared to a standard, or baseline, for differences between the measurements and the standard. The validation may include a process by which effects of a physiological element on a set of measurements directed toward an analyte are subtracted to yield a precise indication of the analyte. The validation may include calibration of the non-invasive analyte measurement device using the invasive analyte measurement device. For example, the processor of the non-invasive analyte measurement device may set an initial measurement by the non-invasive analyte measurement device to be equal to a measurement by the invasive analyte measurement device. The validation may include baselining by setting a standard measurement taken by the invasive analyte measurement device against which non-invasive analyte measurement device measurements are compared. The validation may additionally include extraneous validation of non-invasive analyte measurements using periodic invasive analyte measurements. The validation may additionally include resetting the one or more values stored in the non-invasive analyte measurement device to compensate for physiological changes in the patient. The validation may additionally include determining whether an invasive analyte measurement taken to validate the non-invasive analyte measurements is discontinuous with the non-invasive analyte measurements. The validation may additionally include keeping the invasive analyte measurement and validating the non-invasive analyte measurements if there is a discontinuity. The validation may additionally include discarding the invasive analyte measurement and continuing the non-invasive analyte measurements if the invasive analyte measurement is continuous with the non-invasive analyte measurements.

In various embodiments, a processor associated with the invasive analyte measurement device and/or the non-invasive analyte measurement device, such as the processor of the invasive analyte measurement device 302, the processing unit of the wearable device 100, the processor of the cloud-based server, and/or the processor of the user device 308, may determine a pattern in discontinuities between the analyte measurement curves 704*a-e*. The pattern may be periodic in time. The pattern may be predictable. For example, the processor may determine a likelihood of a size and/or time of a next discontinuity and may update the likelihood based on an actual size and/or time of the next discontinuity. For example, the patient may exercise daily, causing the patient to sweat and skewing non-invasive measurements of the patient's blood glucose. The skewing may be temporary within one time period or may extend across two or more consecutive time periods, causing discontinuity between the analyte measurement curves corresponding to the two or more consecutive time periods. The processor may recognize a pattern in the skewing and may include one or more algorithms to predict and/or compensate for the skewing. For example, the processor may recognize the discontinuity has an average size in a same direction between the time periods. The processor may correlate a slope of the analyte measurement curves within the time periods to the average size of the discontinuity. The processor may subtract the slope and corresponding discontinuity from the analyte measurement curves to generate a corrected analyte measurement curve.

In an embodiment, the wearable device 100 may include one or more sensors and/or programming that may determine when the patient is engaged or about to become engaged in an activity that may lead to drift in the analyte measurement. For example, the wearable device 100 may interface with a calendar of the patient. The patient's calendar may indicate the patient plans to engage in strenuous physical activity, such as playing a sport and/or otherwise exercising. In another example, the wearable device 100 may include a GPS tracker. The GPS tracker may interface with a map which may indicate the patient's location at a given time. The patient may be located at a gym, and the wearable device 100 may infer that the patient is about to exercise. The wearable device 100 may anticipate a change in the patient's hydration condition corresponding with the calendar event and/or the patient's location and may thereby anticipate a drift in the patient's analyte measurements. The wearable device 100 may locally compensate for the anticipated and/or actually-measured drift or the wearable device

100 may communicate the anticipated drift to the cloud-based server 306 and the cloud-based server 306 may adjust the analyte measurements based on the measured and/or anticipated drift.

Figure 7B:
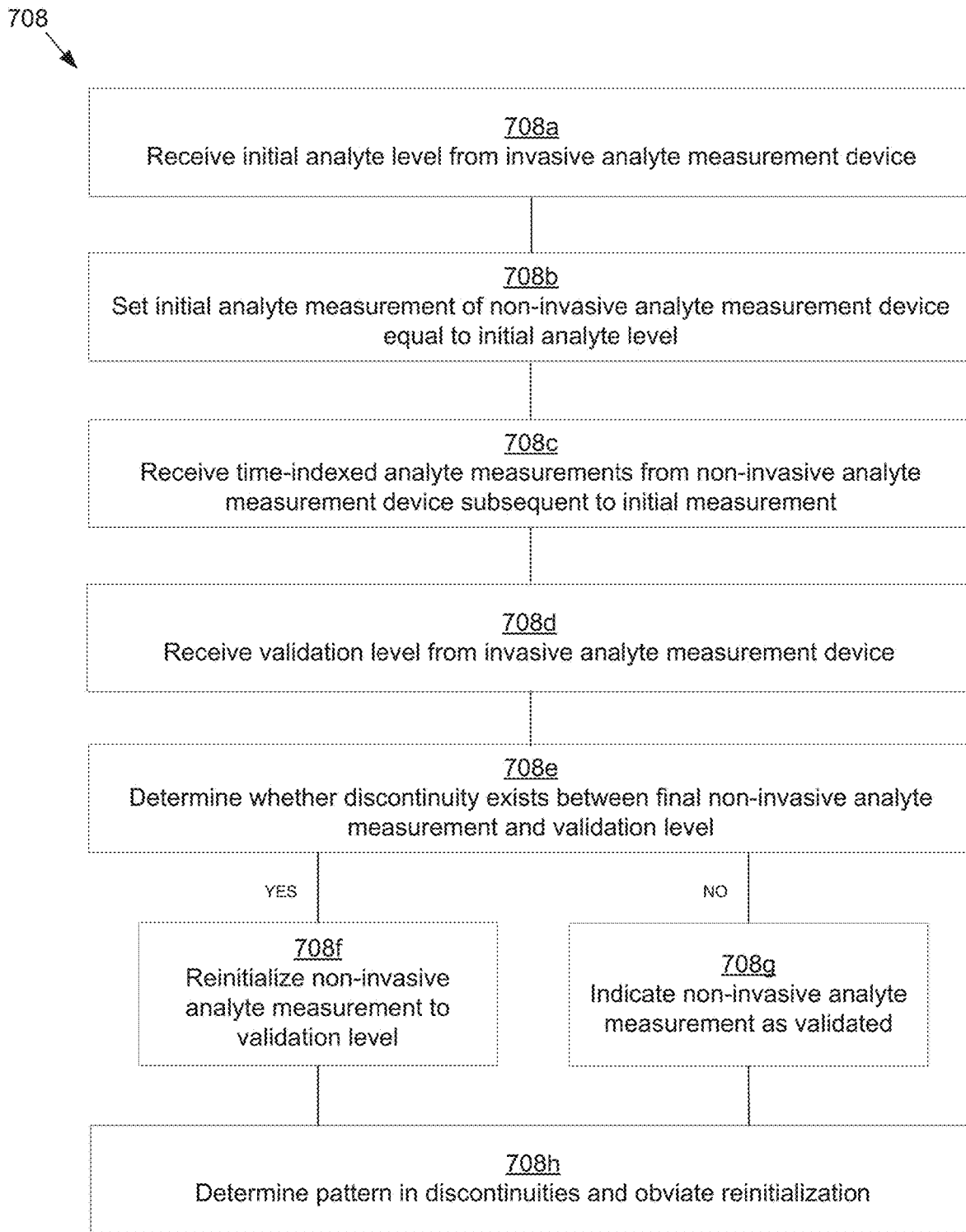
FIG. 7B illustrates a method of validating non-invasive analyte measurements with an invasive analyte measurement after expiration of a time period, according to an embodiment.

FIG. 7B illustrates a method 708 of validating non-invasive analyte measurements with an invasive analyte measurement after expiration of a time period, according to an embodiment. Some of the features in FIG. 7B are the same as or similar to some of the features in FIGS. 1A-7A as noted by same and/or similar reference characters, unless expressly described otherwise. Additionally, reference may be made to features shown in any of FIGS. 1A-7A and not shown in FIG. 7B. In various embodiments, the method 708 may be performed on one device such as the wearable device 100, the invasive analyte measurement device 302, the cloud-based server 306, the user device 308, and so forth. In various embodiments, elements of the method 708 may be performed on separate devices, where the devices from a health device network.

The method 708 may include receiving an initial analyte level from an invasive analyte measurement device (block 708*a*). The method 708 may include setting an initial analyte measurement of a non-invasive analyte measurement device equal to the initial analyte level (block 708*b*). The method 708 may include receiving time-indexed analyte measurements from the invasive analyte measurement device subsequent to the initial measurement (block 708*c*). The method may include receiving a validation level from the invasive analyte measurement device (block 708*d*). The validation level may be based on an invasive analyte measurement. The validation level may be acquired at an end of a time period such as the first time period 602*a*. The validation level may be acquired approximately concurrently with a final non-invasive analyte measurement taken at the end of the time period. The validation level may be acquired approximately concurrently with a most-recent non-invasive analyte measurement taken during the time period. The validation level may be acquired within a threshold time frame of a subset of non-invasive analyte measurements taken during the time period and/or at the end of the time period.

The method 708 may include determining whether a discontinuity exists between the level of the final non-invasive analyte measurement and the validation level (block 708*e*). If a discontinuity exists between the validation level and the final non-invasive analyte measurement, the method 708 may include reinitializing the non-invasive analyte measurements to the validation level (block 708*f*). If there is no discontinuity between the validation level and the final non-invasive analyte measurement, the method 708 may include validating the non-invasive analyte measurements as accurate (block 708*g*). Reinitializing the non-invasive analyte measurements may include setting an initial non-invasive analyte measurement of a second time period to the validation level. After a number of time periods of reinitialization, the method 708 may include determining whether a pattern exists in the discontinuity data and obviating validation based on invasive analyte measurements (block 708*h*). A size, direction, and/or time of the discontinuities may be stored sequentially in memory. If a pattern is determined, a prediction model of future discontinuities may be generated. Based on the prediction model, discontinuity may be anticipated and/or accounted for in non-invasive measurements. This may be done continuously. For example, a slope may be determined for predicted changes in actual analyte levels compared to non-invasively-measured analyte levels over a time period. The non-invasive analyte measurements may be adjusted to fit the slope. Validation measurements may be taken less frequently depending on a performance of the predictive model. Validation measurements may initially be taken daily, then weekly, then monthly, then annually based on a performance of the predictive model.

In various embodiments, a method of creating a predictive model may include: collecting a set of past data elements; predicting a future data element based on the set of past data elements; generating instructions for displaying the future data to a user; and/or transmitting the instructions to a user device, a non-invasive glucometer, or an invasive glucometer. The set of past data elements may include: a history of glucose levels of a subject; a corresponding measurement value of another physiological characteristic of the subject; and/or an activity of the subject during the time interval. The history of glucose levels of the subject may include: a first invasively-measured glucose level of the subject measured at a first time; a second invasively-measured glucose level of the subject measured at a second time after the first time; a time interval from the first time to the second time; and/or a set of non-invasively-measured glucose levels of the subject measured during the time interval. The set of non-invasively-measured glucose levels may include an individual non-invasively measured glucose level measured approximately concurrently with the second invasively-measured glucose level. The corresponding measurement value may be measured during the time interval. The future data element may include: a future glucose level of the subject; a trend of a future set of glucose levels of the subject; a difference between a future invasively-measured glucose level of the subject and a future non-invasively-measured glucose level of the subject; a difference between a future non-invasive glucose measurement reading and a future actual glucose level during a future activity of the subject; a correlation between the future activity and a future corresponding measurement value, the future glucose level, or the future set of glucose levels; and/or a correlation between the future corresponding measurement value of the subject and the future glucose level or the future set of glucose levels. The user may include the subject or another person.

In various embodiments, a method of creating a predictive model may include determining a past data characteristic based on two or more of the past data elements and predicting the future data element based on the past data characteristic. The data characteristic may include: a prediction of a rate of change among glucose measurements during the time interval when the measurement data excludes the set of non-invasively-measured glucose levels; a prediction of a trend in the non-invasively-measured set of glucose levels when the measurement data excludes the non-invasively-measured set of glucose levels; a prediction of the second invasively-measured glucose level when the measurement data excludes the second invasively-measured glucose level; a prediction of the corresponding measurement value when the measurement data excludes the corresponding measurement value; and/or a prediction of the activity when the measurement data excludes the activity.

In various embodiments, a method of creating a predictive model may include: validating the future glucose level or the future set of glucose levels by a validation measurement; training a predictive algorithm with a validation glucose level; in response to the validation glucose level being outside a threshold range of the future glucose level, increasing a future frequency of validating the future glucose level or the set of glucose levels; and/or in response to the validation glucose level being within the threshold range, decreasing the future frequency of validating the future glucose level or the set of glucose levels. The validation measurement may include an invasive glucose measurement. The validation measurement may yield a validation glucose level. The future glucose level or the future set of glucose levels may be measured non-invasively. The predictive algorithm may generate a predicted measurement of the future glucose level or the future set of glucose levels.

In various embodiments, the physiological characteristic of the subject may include: a hydration condition; a blood oxygenation; a heart rate; a blood pressure; a skin complexion; and/or an intensity of a wellness feeling. The wellness feeling may be indicated by: dizziness; nausea; sweating; and/or fatigue. The physiological characteristic may be measured by a non-invasive glucometer that also may measure the non-invasively measured glucose level of the subject. The non-invasive glucometer may include two or more sensors. The non-invasive glucometer may measure the physiological characteristic and the non-invasively measured glucose level using the two or more sensors. Readings by the two or more sensors may be compared to determine a physiological characteristic measurement and/or the non-invasively measured glucose level.

In various embodiments, a method of creating a predictive model may include identifying a trend in historical differences between historical non-invasive glucose measurements of the subject and historical invasive glucose measurements of the subject. Each of the historical differences may be between two approximately concurrent measurements during the time interval of the history of glucose levels The difference between the future invasively-measured glucose level and the future non-invasively-measured glucose level may be predicted based on an individual historical difference of the historical differences. The future invasively-measured glucose level and the future non-invasively measured glucose level may be predicted for approximately concurrent future times. The approximately concurrent future times may occur during a future time interval analogous to the time interval of the history of glucose levels.

In various embodiments, a method of creating a predictive model may include adjusting the future glucose level or the future set of glucose levels. The adjustment may be based on the correlation between the future corresponding measurement value and the future glucose level or the future set of glucose levels. The adjustment may be based on the correlation between the future activity and the future glucose level or the future set of glucose levels. A measured future glucose level may be skewed from the future glucose level due to the physiological characteristic. A measured future set of glucose levels may be skewed from the future set of glucose levels due to the physiological characteristic.

In various embodiments, a method of creating a predictive model may include: collecting a set of data elements; predicting a future data element of a second time interval based on the set of data elements; and/or generating instructions for displaying the future data element to a user. The set of data elements may include: a first set of analyte levels of a subject; a first time interval during which the first set of analyte levels is measured; a first indicator that is indicative of an activity of the subject during the first time interval; and/or a first measurement reading of a physiological characteristic of the subject. The first set of analyte levels may include a first invasively-measured analyte level and/or a first non-invasively measured analyte level. The physiological characteristic may be measured during the first time interval. The future data element may include: a difference between a second non-invasive analyte measurement reading and an actual analyte level during the second time interval; and/or a correlation. The correlation may be between two or more of: the second non-invasive analyte measurement reading; the actual analyte level; a second invasive analyte measurement reading measured during the second time interval; a second indicator that is indicative of an activity of the subject during the second time interval; and/or a second measurement reading of the physiological characteristic measured during the second time interval.

In various embodiments, a method of creating a predictive model may include scheduling a validation of the second non-invasive analyte measurement reading during the second time interval. A prompt may be scheduled to notify the user during the second time interval to validate the second non-invasive analyte measurement reading using the second invasive analyte measurement reading. The second non-invasive analyte measurement reading and the second invasive analyte measurement reading may be taken approximately concurrently. A method of creating a predictive model may include: scheduling a set of validations for a set of non-invasive analyte measurements taken during the second time interval; setting the frequency to increase when individual non-invasive analyte measurement exceeds a threshold difference from the individual invasive analyte measurement; and/or setting the frequency to decrease when the individual non-invasive analyte measurement taken during the second time interval is within the threshold difference. An individual non-invasive analyte measurement of the set of non-invasive analyte measurements taken during the second time interval may be validated against an individual invasive analyte measurement taken approximately concurrently with the individual non-invasive analyte measurement. The set of validations may include a frequency during the second time interval of validation measurements. The set of validations may include a set of randomized validation prompts for the user. The validation prompts are generated at randomly-selected future times during the second time interval.

In various embodiments, a method of creating a predictive model may include setting an alert to be communicated to the subject. The physiological characteristic may include a symptom of an imbalance of an analyte in the subject. A correlation between the second non-invasive analyte measurement reading and the activity during the second time interval may indicate the subject will experience the symptom. The alert may be set to be communicated to the subject when the correlation between the second non-invasive analyte measurement reading and the activity during the second time interval indicates the subject will experience the symptom. A predictive algorithm that predicts the data element may be isolated from a wearable device worn by the subject such that the predictive algorithm is inaccessible through the wearable device. The wearable device may be configured to non-invasively measure an analyte level of the subject.

In various embodiments, a system may include: an invasive analyte measurement device; a non-invasive analyte measurement device; and/or a processing device communicatively networked to the invasive analyte measurement device and the non-invasive analyte measurement device. The processing device may be configured to: collect a set of data elements from the invasive analyte measurement device and the non-invasive analyte measurement device; and/or predict an individual data element based on the set of data elements. The set of data elements may include a first set of analyte levels of a subject and/or a time interval during which the first set of analyte levels is measured. The first set of analyte levels may include a first invasively-measured analyte level and a first non-invasively measured analyte level. The individual data element may include a difference between two or more of: a second non-invasive analyte measurement reading; a second invasive analyte measurement reading; and an actual analyte level.

In various embodiments, the processing device may be configured to: continuously or iteratively monitor a current incoming non-invasive analyte measurement readings; and/or continuously or iteratively generate predicted values for the incoming non-invasive analyte measurement readings. The predicted values may be based on: the first set of analyte levels; the time interval; and/or times at which the current incoming non-invasive analyte measurement readings are measured. The times at which the current incoming non-invasive analyte measurement readings are measured may be analogous to times during the time interval at which the set of analyte levels were measured.

In various embodiments, the processing device may be configured to adjust a prediction of the second non-invasive analyte measurement reading based on a validation of a previous non-invasive analyte measurement reading with a previous invasive analyte measurement reading. The previous non-invasive analyte measurement reading and the previous invasive analyte measurement reading may be measured approximately concurrently. The previous non-invasive analyte measurement reading and the previous invasive analyte measurement reading may be taken previous to the second non-invasive analyte measurement reading.

In various embodiments, the analyte may include glucose. A hydration condition of the subject may skew the second non-invasive analyte measurement reading from the actual analyte level. Predicting the individual data element may include predicting the hydration condition and/or adjusting the second non-invasive analyte measurement reading to the actual analyte level. The set of data elements may include an activity of the subject performed during the time interval. The individual data element may include an influence of the activity of the subject on the actual analyte level. The processing device may be configured to prompt the subject to take an invasive analyte measurement reading. The set of data elements may include data indicative of an adverse symptom experienced by the subject during the time interval. The individual data element may include a trend in a set of the second non-invasive analyte measurement reading. Prompting the subject may be triggered by identifying the trend.

Figure 8A:
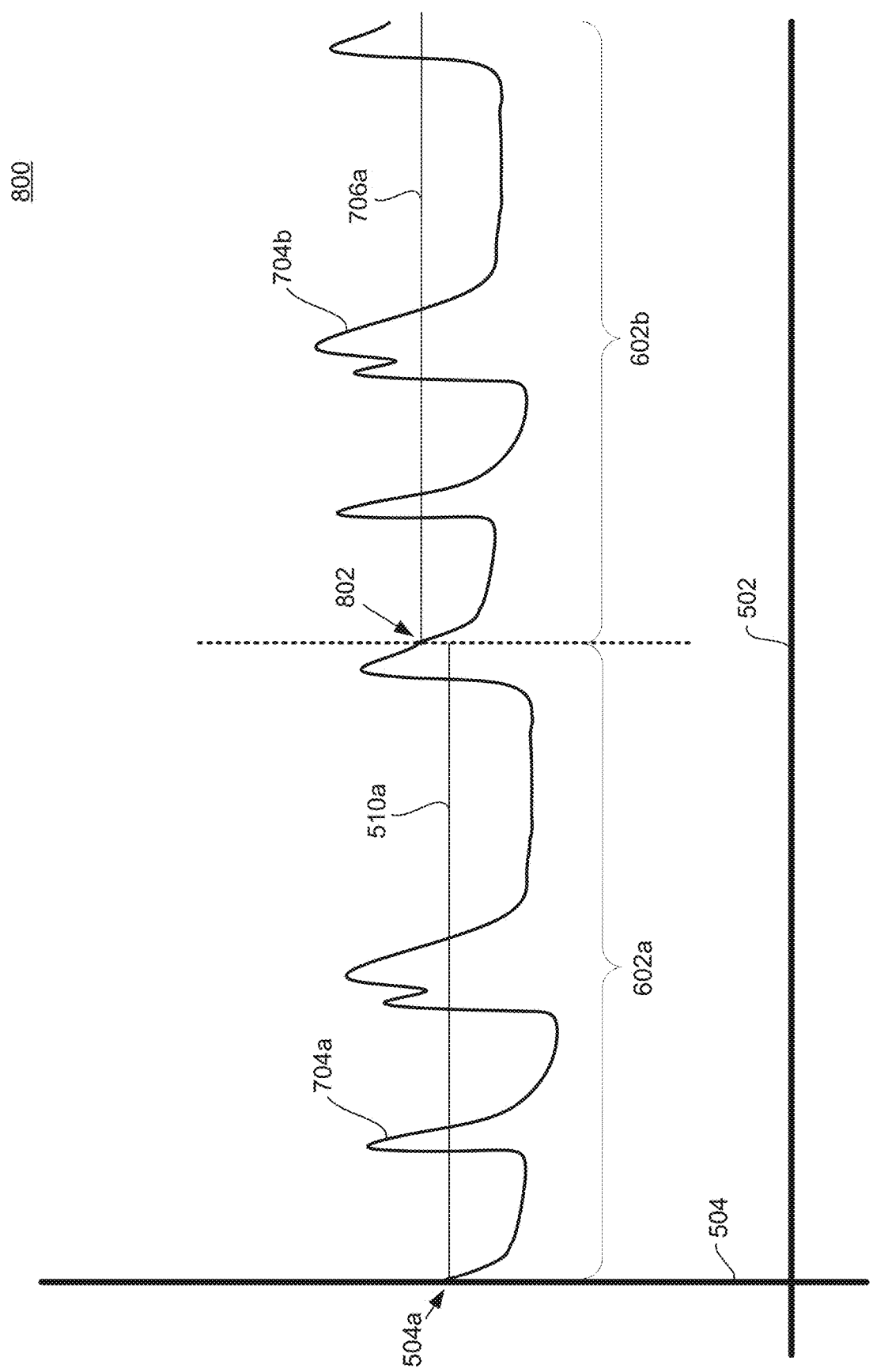
FIG. 8A illustrates a graph showing a continuity between a first analyte measurement curve corresponding to a first time period and a second analyte measurement curve corresponding to a second time period, according to an embodiment.

FIG. 8A illustrates a graph 800 showing a continuity between the first analyte measurement curve 704a corresponding to the first time period 602a and the second analyte measurement curve 704b corresponding to the second time period 602b, according to an embodiment. Some of the features in FIG. 8A are the same as or similar to some of the features in FIGS. 1A-7B as noted by same and/or similar reference characters, unless expressly described otherwise. Additionally, reference may be made to features shown in any of FIGS. 1A-7B and not shown in FIG. 8A. The continuity may be confirmed by a validating analyte measurement 802 taken by an invasive analyte measurement device. The validating analyte measurement 802 may include a reinitialized analyte measurement. The validating analyte measurement 802 may match a final measurement taken by the non-invasive analyte measurement device during the first time period 602a. The validating analyte measurement may confirm the final measurement taken by the non-invasive analyte measurement device is accurate. In an embodiment, the validating analyte measurement may match one or more measurements of a set of final measurements taken during the first time period 602a. Match may refer to being exactly the same or falling within a threshold range of each other.

Continuity between the final measurement or a final data set of the non-invasive analyte measurement device and the validating analyte measurement 802 by the invasive analyte measurement device may indicate a trend. If the validating analyte measurement 802 matches the initial analyte level 504a, the processor may determine the patient's analyte levels may be periodically consistent. The processor may further make such a determination if the first analyte measurement curve 704a and the second analyte measurement curve 704b have similar shapes. If there is a difference between the validating analyte measurement 802 and the initial analyte level 504b, the processor may determine the patient's average analyte levels are changing. The processor may further make such a determination based on periodic differences between the first analyte measurement curve 704a and the second analyte measurement curve 704b, and or average differences between other analyte measurement curves corresponding to past time periods.

Continuous may be used to refer to obtaining analyte measurements. Continuous analyte measurement may refer to an uninterrupted progression of measurements. Continuous analyte measurements may refer to analyte measurements taken consecutively at significantly smaller time scales than a length of the consecutive time periods 602a-e. For example, continuous analyte measurements during a time period of 24 hours may include analyte measurements taken 1 minute to 30 minutes apart, 1 minute to 15 minutes apart, 1 minute to 10 minutes apart, 1 minute to 5 minutes apart, 1 second to 1 minute apart, 1 second to 30 seconds apart, 1 second to 15 seconds apart, 1 second to 10 seconds apart, 1 second to 5 seconds apart, less than one second apart, and so forth. In another example, continuous analyte measurements during a time period of one week may include analyte measurements taken 1 hour to 4 hours apart, 1 minute to 1 hour apart, 1 minute to 30 minutes apart, and so forth. Whether analyte measurements may be considered continuous may depend on a time scale over which changes in the level of the analyte may occur. For example, when the level of the analyte may change dramatically over the course of a few minutes, continuous analyte measurement may refer to analyte measurements taken 1 second to 5 seconds apart, 1 second apart, less than 1 second apart, and so forth. When a minimum time period for dramatic change in the level of the analyte may include a few days, continuous analyte measurement may refer to analyte measurements taken 1 minute to 60 minutes apart, 1 minute to 30 minutes apart, 1 minute to 15 minutes apart, and so forth.

Continuous and discontinuous may refer to changes between analyte levels of consecutive analyte measurements. Continuous may refer to zero change between simultaneous analyte measurements taken by different analyte measurement devices. Continuous may refer to changes between consecutive measurements taken by the same measurement device that follow a curve such as the analyte measurement curves 704a-e. Continuous may refer to changes between consecutive measurements taken by the same measurement device, where the consecutive measurements are within a threshold range of each other. Continuous may be contrasted with discontinuous. Discontinuous may refer to a non-zero change between simultaneous analyte measurements taken by different analyte measurement devices. Discontinuous may refer to atypical, unexpected, and/or uncharacteristic changes between consecutive measurements taken by the same measurement device. Discontinuous may refer to changes between consecutive measurements taken by the same measurement device that depart from a local slope and/or shape of a curve such as the analyte measurement curves 704a-e.

Figure 8B:
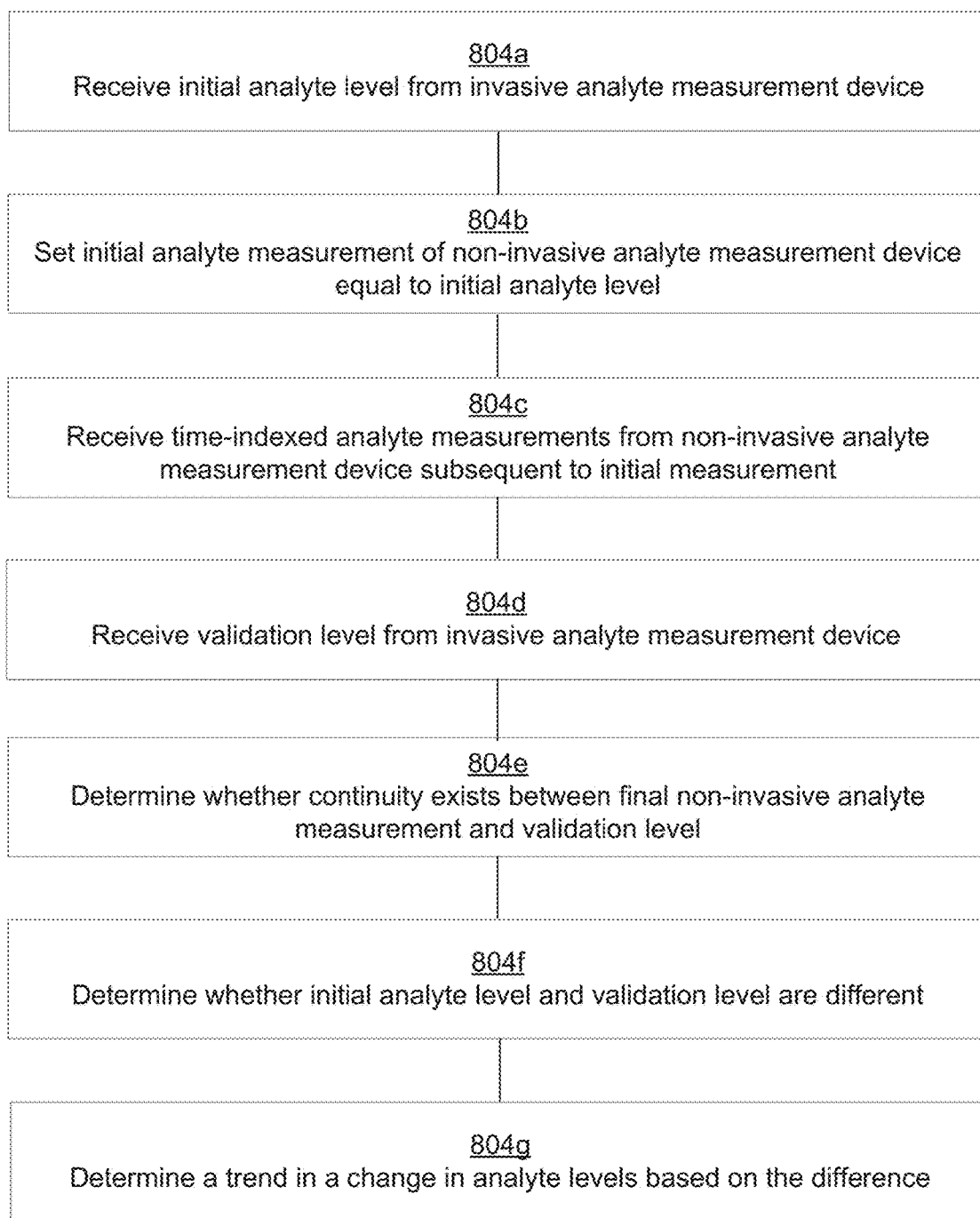
FIG. 8B illustrates a method of determining a change in a physiological feature based on a discontinuity between an initial analyte level and a validation level, according to an embodiment.

FIG. 8B illustrates a method 804 of determining a change in a physiological feature based on a discontinuity between an initial analyte level and a validation level, according to an embodiment. Some of the features in FIG. 8B are the same as or similar to some of the features in FIGS. 1A-8A as noted by same and/or similar reference characters, unless expressly described otherwise. Additionally, reference may be made to features shown in any of FIGS. 1A-8A and not shown in FIG. 8B. In various embodiments, the method 804 may be performed on one device such as the wearable device 100, the invasive analyte measurement device 302, the cloud-based server 306, the user device 308, and so forth. In various embodiments, elements of the method 804 may be performed on separate devices, where the devices from a health device network.

The method 804 may include receiving an initial analyte level from an invasive analyte measurement device (block 804a). The method 804 may include setting an initial analyte measurement of a non-invasive analyte measurement device equal to the initial analyte level (block 804b). The method 804 may include receiving time-indexed analyte measurements from the non-invasive analyte measurement device subsequent to the initial measurement (block 804c). The method may include receiving a validation level from the invasive analyte measurement device (block 804d). The validation level may be based on an invasive analyte measurement. The validation level may be acquired at an end of a time period such as the first time period 602a. The validation level may be acquired concurrently with a final non-invasive analyte measurement or set of measurements taken at the end of the time period. In an embodiment, the validation level may be acquired whenever the user takes the invasive analyte measurement. In another embodiment, the user may be prompted to take the invasive analyte measurement to validate the measurements from the non-invasive analyte measurement device when the non-invasive analyte measurement device, the invasive analyte measurement device, the user device, and/or the server determines one or more of the non-invasive analyte measurements may be inaccurate and that measurement by the non-invasive analyte measurement device should be validated with the invasive analyte measurement.

The method 804 may include determining whether a continuity exists between the level of the final non-invasive analyte measurement or set of measurements and the validation level (block 804e). If a continuity exists between the level of the final non-invasive analyte measurement or set of measurements and the validation level, the final non-invasive analyte measurement or set of measurements may be set as an initial non-invasive analyte measurement or set of measurements of a subsequent time period, such as the second time period 602b. The method 804 may include determining whether the initial analyte level and the validation level are different (block 804f). If the difference is non-zero and the final non-invasive analyte measurement and validation level are continuous, then the difference may include an indication of a change in the analyte level at times when no change might otherwise be expected. For example, the analyte may include blood glucose, and the invasive measurements may be taken during periods of fasting. A change in the invasive analyte measurements during periods of fasting may indicate a trending change in the analyte levels. Accordingly, the method 804 may include determining the trending change in the analyte levels based on the difference (block 804g). The trending change may indicate an improving and/or worsening health of the patient. For example, the analyte may be blood glucose. The trending change may indicate a decrease in the patient's $A_{1c}$ levels from diabetic levels towards non-diabetic levels.

In various embodiments, a method of validating a set of non-invasively measured glucose levels may include: receiving a first set of non-invasively measured glucose levels from a wearable device (e.g. the wearable device 100); receiving a validation level from an invasive glucometer (e.g. the invasive analyte measurement device 302); determining a measurement difference between the validation level and the final level; receiving a second set of non-invasively measured glucose levels from the wearable device; and validating the final level by a validation process. The wearable device may include a light source and a miniaturized spectrometer. The light source may be positioned in the wearable device to emit light through an artery of a subject (e.g. the muscular-walled tube 206a or 206b) as the subject wears the wearable device. The miniaturized spectrometer may be positioned in the wearable device to receive the light through the artery as the subject wears the wearable device. The wearable device may include a processing device that determines an amount of blood glucose of the subject based on the light received through the artery. The validation level may be measured approximately concurrently with a final level of the first set of non-invasively measured glucose levels. Validating the final level may be based on the measurement difference between the validation level and the final level or a measurement of another physiological characteristic. The validation process may include, in response to the measurement difference being greater than or equal to a first threshold difference, adjusting the second set of non-invasively measured glucose levels. The validation process may include, in response to the measurement difference being less than or equal to the first threshold difference, disregarding the measurement difference. In an embodiment, a change in the other physiological characteristic may correspond to a change in the amount of blood glucose of the subject. The validation process may include adjusting the second set of non-invasively measured glucose levels based on the measurement of the other physiological characteristic.

In various embodiments, a method of validation may include: measuring an initial hydration condition of the subject; measuring a final hydration condition of the subject; and identifying a drift in the first set of non-invasively measured glucose levels. The drift may be attributable to a difference between the initial hydration condition and the final hydration condition. In various embodiments, a method of validation may include: continuously or iteratively monitoring the other physiological characteristic for the change in the other physiological characteristic; and/or continuously or iteratively adjusting incoming non-invasively measured glucose levels when the change in the other physiological characteristic indicates the incoming non-invasively measured glucose levels are drifted from actual glucose levels of the subject.

In various embodiments, a method of validation may include generating a prompt designated for the subject. The prompt may request that the subject measure the validation level. The prompt may be generated after a fixed number of individual levels of the first set of non-invasively measured glucose levels is received. The prompt may be generated after a fixed period of time after initial non-invasively measured glucose level of the first set of non-invasively measured glucose levels is received. A second threshold difference may be calculated between two of the individual levels of the first set of non-invasively measured glucose levels.

In various embodiments, a method of validation may include: detecting a drift in the first set of non-invasively measured glucose levels; eliminating the other physiological characteristic as an influencing factor in the drift; prompting the subject to recalibrate the wearable device; prompting the subject to adjust a position of the wearable device on the subject to align the miniaturized spectrometer or the light source with the artery; prompting the subject to take a revalidation measurement comprising an invasively-measured glucose reading; receiving a confirmation from the subject that the subject has adjusted the wearable device; receiving the revalidation measurement; receiving a test non-invasive measurement reading; determining a revalidation difference between the revalidation measurement and the test non-invasive measurement reading; comparing the revalidation difference to a threshold revalidation difference; in response to determining the revalidation difference is within the threshold revalidation difference, confirming the test non-invasive measurement reading is accurate; and/or in response to determining the revalidation difference is outside the threshold difference, prompting the subject to perform another adjustment action or a calibration.

In various embodiments, a device for validating non-invasive analyte (e.g. glucose) measurements may include: networking hardware communicatively coupled to an invasive analyte measurement device, a non-invasive analyte measurement device, and a user device (e.g. the user device 308); and a processing device. For example, the device may include a cloud-based server (e.g. the cloud-based server 306). The processing device may be configured to (e.g. include instructions that, when executed, cause the processing device to perform various tasks): receive an initial invasively measured analyte level of a subject; receive an initial non-invasively measured analyte level of the subject; calculate a first difference; adjust the initial non-invasively measured analyte level based on the first difference; receive a first set of subsequent non-invasively measured analyte levels; and/or adjust individual levels of the first set of subsequent non-invasively measured analyte levels based on the first difference. The initial invasively measured analyte level and/or the initial non-invasively measured analyte level may be measured approximately concurrently. The first difference may be between the initial invasively measured analyte level and the initial non-invasively measured analyte level. The first set of subsequent non-invasively measured analyte levels may be measured by the non-invasive analyte measurement device after the initial non-invasively measured analyte level.

In various embodiments, a processor of a validation device may be configured to: receive a validation level from the invasive analyte measurement device; calculate a second difference; calculate a third difference; validate the final level to be equal to the validation level; receive a second set of subsequent non-invasively measured analyte levels from the non-invasive analyte measurement device; adjust the second set of subsequent non-invasively measured analyte levels based on the third difference; transmit the initial non-invasively measured analyte level, the first set of subsequent non-invasively measured analyte levels, and/or the second set of subsequent non-invasively measured analyte levels to the user device; and/or transmit the initial invasively measured analyte level and the validation level to the user device. The validation level may be measured approximately concurrently with a final level of the first set of subsequent non-invasively measured analyte levels. The final level may be previously adjusted based on the first difference. The second difference may be between the final level and the validation level. The third difference may be between the first difference and the second difference. The final level may be adjusted based on the third difference.

In various embodiments, the initial invasively measured analyte level and the validation level may be measured by the invasive analyte measurement device. The initial non-invasively measured analyte level, the first set of subsequent non-invasively measured analyte levels, and/or the second set of subsequent non-invasively measured analyte levels may be measured by a wearable non-invasive analyte measurement device. The initial invasively measured analyte level, the initial non-invasively measured analyte level, the first set of subsequent non-invasively measured analyte levels, the validation level, and/or the second set of subsequent non-invasively measured analyte levels may be routed through a hub. The hub may include the invasive analyte measurement device and/or the wearable non-invasive analyte measurement device.

In various embodiments, a processor of a validation device may be configured to: compile the initial non-invasively measured analyte level, the first set of subsequent non-invasively measured analyte levels, the second set of subsequent non-invasively measured analyte levels, the initial invasively measured analyte level, and/or the validation level into a time-indexed graph; and/or transmit the time-indexed graph to the user device. The time-indexed graph may include: a first indicator for the initial non-invasively measured analyte level; a second indicator for the initial invasively measured analyte level; a first curve for the first set of subsequent non-invasively measured analyte levels; a second curve for the second set of subsequent non-invasively measured analyte levels; a third indicator for the validation level; a fourth indicator for the final level; and/or a delineating line between the first curve and the second curve.

In various embodiments, the user device may be configured to compile measurement data into a graphical display. The measurement data may include: the initial non-invasively measured analyte level; the initial invasively measured analyte level; the first set of subsequent non-invasively measured analyte levels; the second set of subsequent non-invasively measured analyte levels; and/or the validation level. The processing device is configured to transmit the individual levels to the user device as the individual levels are received by the processing device, wherein the user device is configured to display the graphical display to a user and update the graphical display with the individual levels in real-time as the graphical display is displayed to the user and as the individual levels are received at the user device. In various embodiments, the second difference may indicate a drift in a concentration of an analyte in the subject. The analyte may be indicated by the initial non-invasively measured analyte level, the initial invasively measured analyte level, the first set of subsequent non-invasively measured analyte levels, the second set of subsequent non-invasively measured analyte levels, and/or the validation level. The validation level may reflect an absolute level of the analyte in the subject.

In various embodiments, a processor of a validation device may be configured to: compare the initial non-invasively measured analyte level, the initial invasively measured analyte level, the first set of subsequent non-invasively measured analyte levels, the second set of subsequent non-invasively measured analyte levels, and/or the validation level to a baseline analyte level; and/or calibrate the invasive analyte measurement device or the non-invasive analyte measurement device based on a target output of the invasive analyte measurement device or the non-invasive analyte measurement device. The baseline analyte level may include: a starting level of an analyte for a subject from a first time analyte levels of the subject started being tracked; a time-averaged level of the analyte for the subject; and/or a population-averaged level of the analyte for a population of which the subject is a part. A hardware element or a software element of the invasive analyte measurement device or the non-invasive analyte measurement device may be changed by the calibration. The processing device may generate a prompt or an instruction for the subject to change the invasive analyte measurement device or the non-invasive analyte measurement device. The target output may be determined by a calibration measurement and/or may be designated by the subject. The calibration measurement may be taken by the non-invasive analyte measurement device and/or by the invasive analyte measurement device.

In various embodiments, a method of validation may include: receiving a first set of non-invasively measured analyte levels; receiving a validation level; determining whether the validation level and the final level are different; validating the final level to be equal to the validation level; receiving a second set of non-invasively measured analyte levels from a non-invasive analyte measurement device; and/or adjusting the second set of non-invasively measured analyte levels based on a difference. The validation level may be measured approximately concurrently with a final level of the first set of non-invasively measured analyte levels. The difference may be calculated between the final level and the validation level. The final level may be adjusted by the difference.

In various embodiments, a method of validation may include: receiving an initial invasively measured analyte level of a subject; and/or setting an initial non-invasively measured analyte level of the subject equal to the initial invasively measured analyte level. The initial invasively measured analyte level and the initial non-invasively measured analyte level may be measured approximately concurrently. A second difference may be calculated. The second difference may be between the initial invasively measured analyte level and the initial non-invasively measured analyte level. The initial non-invasively measured analyte level may be adjusted based on the second difference.

In various embodiments, a method of validation may include identifying a fasting glucose level of the subject is changing and/or generating a notification that the fasting glucose level is changing. The initial non-invasively measured analyte level, the initial invasively measured analyte level, the first set of non-invasively measured analyte levels, the second set of non-invasively measured analyte levels, and/or the validation level may measure glucose in blood of the subject. The initial non-invasively measured analyte level and/or the validation level may be measured during a fasting period of the subject. Identifying the fasting glucose level of the subject is changing may include: calculating a third difference and/or a fourth difference; and/or determining the third difference is less than a threshold amount and the fourth difference is greater than the threshold amount. The third difference may be between the validation level and the final level. The fourth difference may be between the initial invasively measured analyte level and the validation level. The threshold amount may be an error margin of measurements by an invasive analyte measurement device measuring the validation level and/or a non-invasive analyte measurement device measuring the final level.

In various embodiments, a method of validation may include comparing a measured analyte level of the subject to a baseline analyte level; and/or generating an output that indicates a difference between the baseline analyte level and the measured analyte level. The measured analyte level may include: the initial non-invasively measured analyte level; the initial invasively measured analyte level; the first set of non-invasively measured analyte levels; the second set of non-invasively measured analyte levels; and/or the validation level. The baseline analyte level may include: a starting level of the analyte for the subject from a first time analyte levels of the subject started being tracked; a time-averaged level of the analyte levels for the subject; and/or a population-averaged level of the analyte for a population of which the subject is a part. A final individual measurement may produce the final level. Validating the final level may remove a non-analyte portion from the final individual measurement such that: the final level less the difference between the final level and the validation level may equal an absolute analyte level of the subject; and/or the second difference may equal the absolute analyte level of the subject. The non-analyte portion of the final individual measurement may be attributable to a physiological characteristic of the subject other than an analyte level of the subject.

Figure 9A:
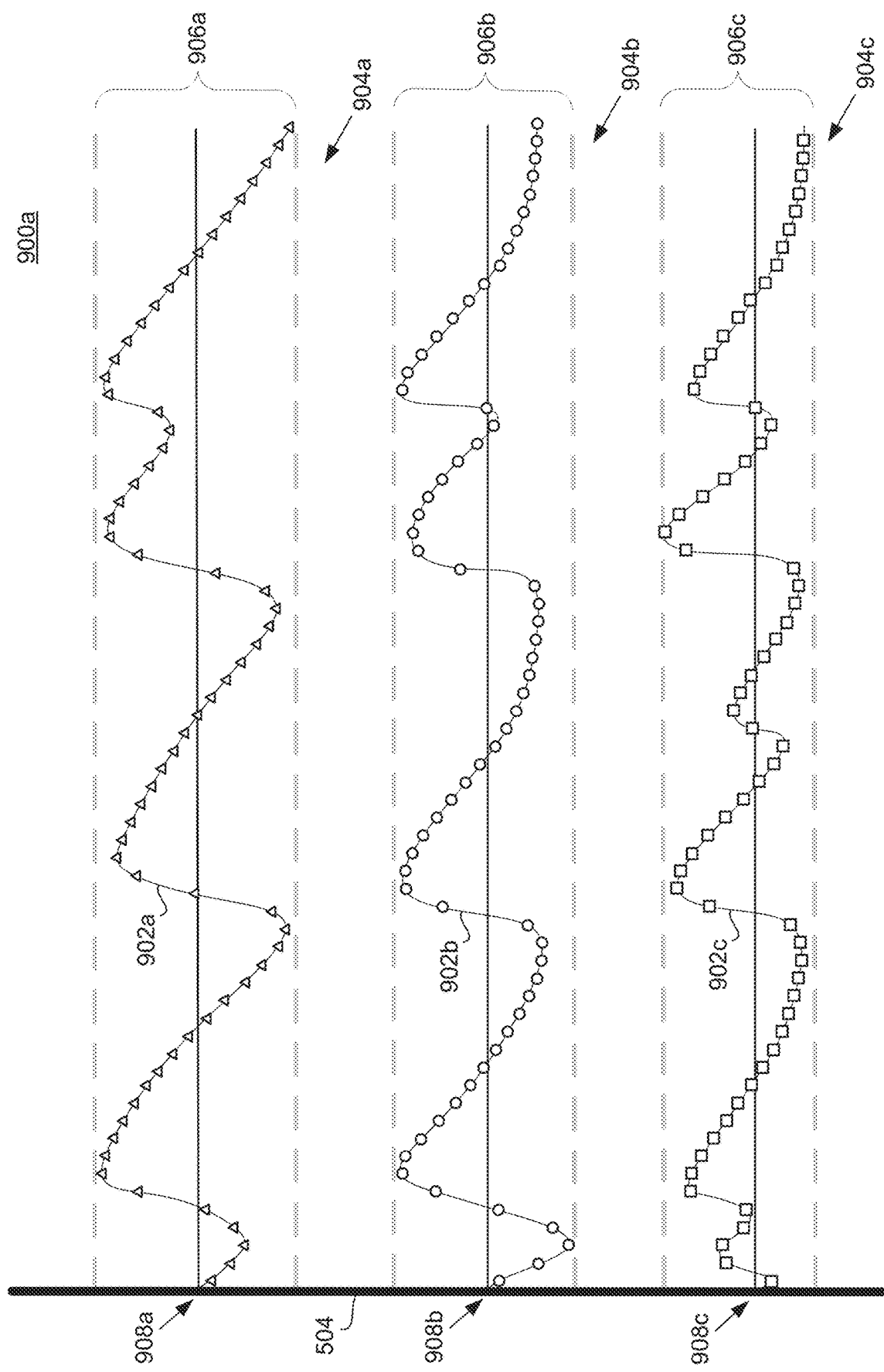
FIG. 9A illustrates a graph of three analyte measurement curves corresponding to three non-consecutive time periods, according to an embodiment.

FIG. 9A illustrates a graph 900a of three analyte measurement curves 902a-c corresponding to three non-consecutive time periods 904a-c, according to an embodiment. Some of the features in FIG. 9A are the same as or similar to some of the features in FIGS. 1A-8B as noted by same and/or similar reference characters, unless expressly described otherwise. Additionally, reference may be made to features shown in any of FIGS. 1A-8B and not shown in FIG. 9A. A first analyte measurement curve 902a corresponds to a first time period 904a. A second analyte measurement curve 902b corresponds to a second time period 904b. A third analyte measurement curve 902c corresponds to a third time period 904c. The second time period 904b occurs after the first time period 904a with one or more other time periods occurring between the first time period 904a and the second time period 904b. The third time period 904c occurs after the second time period 904b with one or more other time periods occurring between the second time period 904b and the third time period 904c. The first analyte measurement curve 902a may have a first range of analyte levels 906a and a first initial analyte level 908a. The second analyte measurement curve 902b may have a second range of analyte levels 906b and a second initial analyte level 908b. The third analyte measurement curve 902c may have a third range of analyte levels 906c and a third initial analyte level 908c.

The second initial analyte level 908b may be lower along the analyte level axis 504 than the first initial analyte level 908a. Analyte measurements along the second analyte measurement curve 902b may fall below analyte measurements along the first analyte measurement curve 902a. A highest analyte level of the second range of analyte levels 906b may be lower than a lowest analyte level of the first range of analyte levels 906a. The second range of analyte levels 906b may be narrower than the first range of analyte levels 906a. The third initial analyte level 908c may be lower along the analyte level axis 504 than the second initial analyte level 908b. Analyte measurements along the third analyte measurement curve 902c may fall below analyte measurements along the second analyte measurement curve 902b. A highest analyte level of the third range of analyte levels 906c may be lower than a lowest analyte level of the second range of analyte levels 906b. The third range of analyte levels 906c may be narrower than the second range of analyte levels 906b.

The graph 900a may reflect that the patient had lower analyte levels during the second time period 904b than during the first time period 904a. The graph 900a may reflect that the patient had a narrower variation in analyte levels during the second time period 904b than during the first time period 904a. The graph 900a may reflect that the patient had lower analyte levels during the third time period 904c than during the second time period 904b. The graph 900a may reflect that the patient had a narrower variation in analyte levels during the third time period 904c than during the second time period 904b. The change in analyte levels and in the range of variation of the analyte levels from the first time period 904a to the third time period 904c may reflect changes in the patient's behavior affecting the analyte levels. In various embodiments, the analyte may include blood glucose. As the patient adopts healthy behaviors, the patient's blood glucose levels may decrease, and variations in the patient's blood glucose levels may decrease.

In an embodiment, the graph 900a may be referenced to the coefficient of variation instead of the analyte levels. For example, the first range of analyte levels 906a may instead be a first coefficient of variation and/or a multiple of the coefficient of variation, etc. The first analyte measurement curve 902a may be plotted relative to the first coefficient of variation, etc. In another embodiment, the graph 900a may be referenced to a standard deviation of the user's analyte measurements from a representative analyte measurement such as a mean or media measurement, a fasting measurement, an average fasting measurements, an average postprandial measurement, and so forth. For example, the first range of analyte levels 902a may instead be the standard deviation and/or a multiple of the standard deviation, etc. The first analyte measurement curve 902a may be plotted relative to the standard deviation, etc.

Figure 9B:
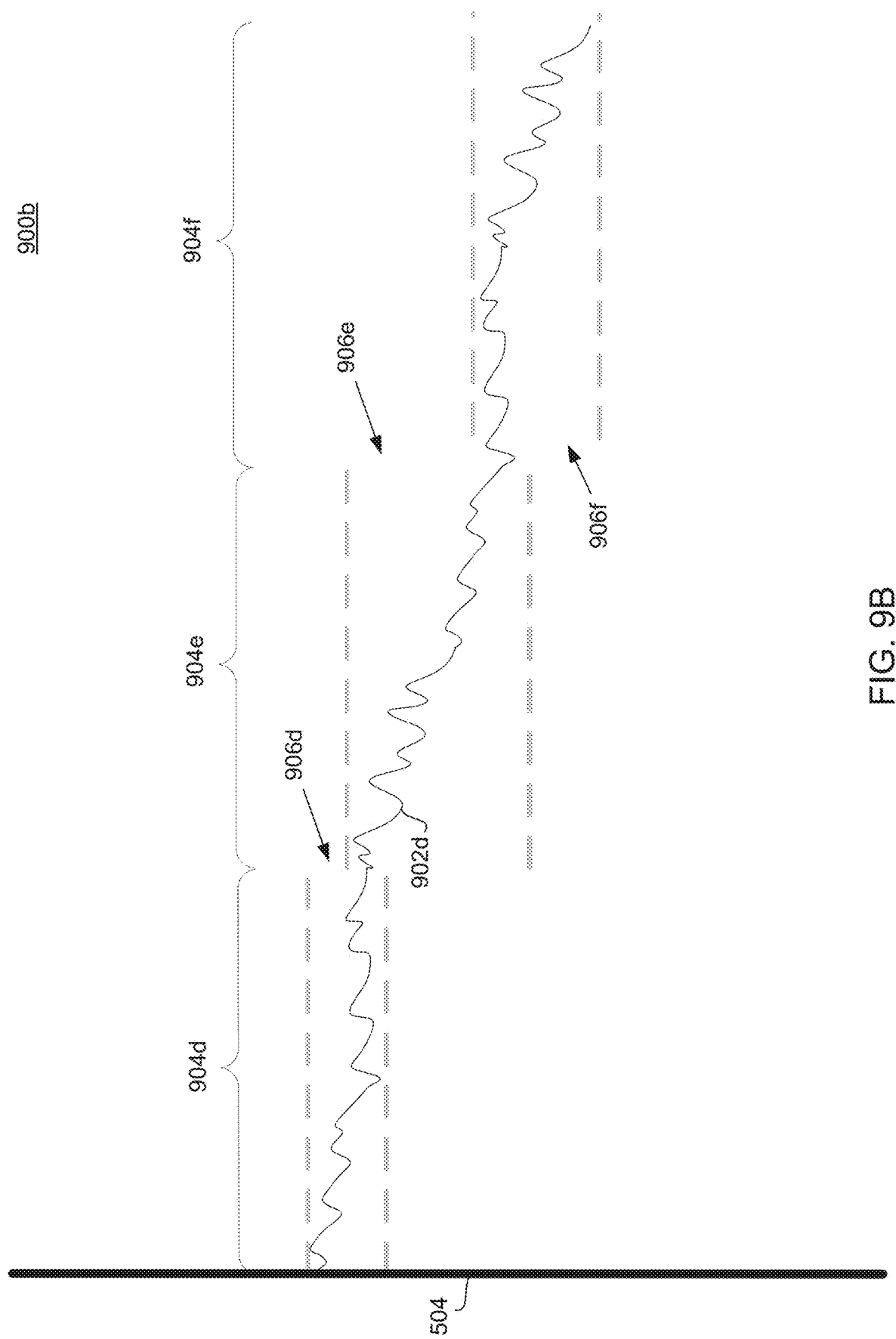
FIG. 9B illustrates a graph of a continuous analyte measurement curve over three consecutive time periods, according to an embodiment.

FIG. 9B illustrates a graph 900b of a continuous analyte measurement curve 902d over three consecutive time periods 904d-f, according to an embodiment. Some of the features in FIG. 9A are the same as or similar to some of the features in FIGS. 1A-8B as noted by same and/or similar reference characters, unless expressly described otherwise. Additionally, reference may be made to features shown in any of FIGS. 1A-8B and not shown in FIG. 9A. the graph 900b demonstrates a similar principle to the graph 900a, except in a linear fashion. In an embodiment, the curve 902d may be characterized by three consecutive time periods, a fourth time period 904d (continuing the nomenclature of FIG. 9A), a fifth time period 904e, and a sixth time period 904f. The curve 902d has a fourth range 906d during the fourth time period 904d, a fifth range 906e during the fifth time period 904e, and a sixth range 906f during the sixth time period 904f.

In an embodiment, a diabetic patient may have goals for improving the diabetic patient's health. The goals may include decreasing an amount of variation in the patient's glucose measurements, such as shrinking the patient's coefficient of variation and/or standard deviation for measurements during a given time period. Shrinking the coefficient of variation and/or standard deviation may include reducing a difference between a minimum measurement value and a maximum measurement value corresponding to the coefficient of variation and/or standard deviation. For example, the amount of variation in the patient's glucose measurements decreases from the fifth time period 904e to the sixth time period 904f. The fifth range 906e and the sixth range 906f may correspond directly to the patient's coefficient of variation during the fifth time period 904e and the patient's coefficient of variation during the sixth time period 904f. Accordingly, the patient's coefficient of variation may shrink from the fifth time period 904e to the sixth time period 904f.

The goals may include decreasing an average value for measurements during the time period. Decreasing the average value may include decreasing the maximum and minimum measurement values associated with the coefficient of variation and/or standard deviation. For example, the average value of the curve 902d during the sixth time period is less than the average value of the curve 902d during the fifth time period 904e. Accordingly, the patient's coefficient of variation and/or standard deviation occupies a lower place on the graph 900b relative to the analyte level axis 504 during the sixth time period 904f than during the fifth time period 904e.

The goals may include decreasing an average value for measurements during the time period and decreasing the amount of variation. Accomplishment of both goals is reflected in the difference in the analyte measurements and ranges, and therefore the coefficients of variation and/or standard deviations, between the fifth time period 904e and the sixth time period 904f. The goals may include decreasing the average value for the measurements without regard for decreasing the amount of variation, which may be represented by the difference between the analyte measurements, and therefore the coefficients of variation and/or standard deviations, between the fourth time period 904d and the fifth time period 904e. The goals may include decreasing the amount of variation without regard for the for decreasing the average value for the measurements, which may be represented by the difference between the analyte measurements, and therefore the coefficients of variation and/or standard deviations, between the fifth time period 904e and the sixth time period 904f. In various other embodiments, the goals may include increasing and/or decreasing, over time, the average value for the measurements and/or the amount of variation, and therefore the coefficients of variation and/or standard deviations.

The graphs 500, 600, 700, 800, 900a and/or 900b may provide a visual depiction of data collected by a device in a health device network. The graphs 500, 600, 700, 800, 900a and/or 900b may provide a visual depiction of how data collected by the device may be processed to provide useful information to a user of the device. The device may include a measurement device such as the wearable device 100, the invasive analyte measurement device 302, and/or the peripheral measurement device(s) 304. The device may include the cloud-based server 306, and/or the user device 308. The user may include the patient, a healthcare provider, and/or a third party with permission to access the patient's health information and/or use the device. Data depicted by the graphs 500, 600, 700, 800, 900a and/or 900b may be displayed to the user by the device and/or by another device. In various embodiments, the graphs 500, 600, 700, 800, 900a and/or 900b may be displayed to the user by the device. The user may utilize the data and/or the graphs 500, 600, 700, 800, 900a and/or 900b to diagnose disease in the patient. The user may utilize the data and/or the graphs 500, 600, 700, 800, 900a and/or 900b to track progress towards goals of the patient. The user may utilize the data and/or the graphs 500, 600, 700, 800, 900*a*, and/or 900*b* to monitor the patient's health in real-time.

Figure 9C:
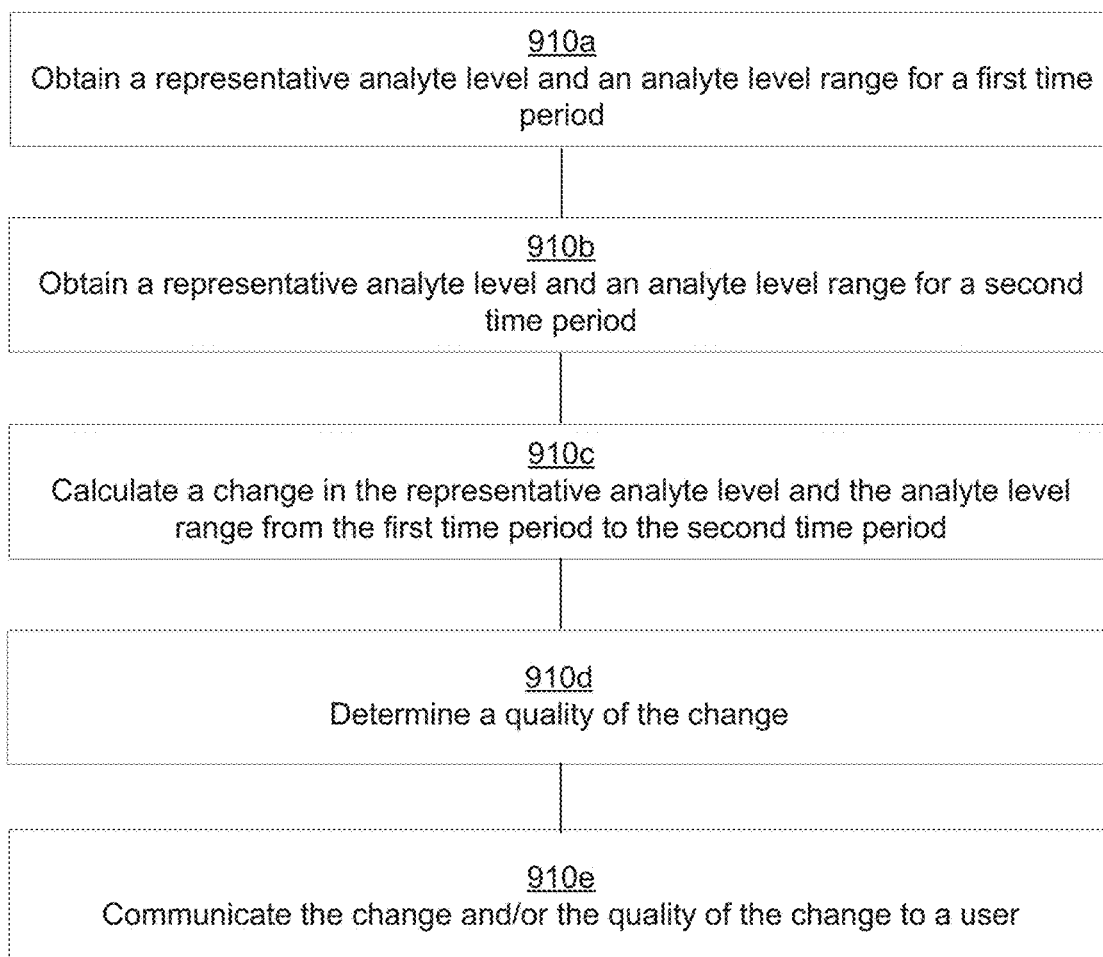
FIG. 9C illustrates a method of adjusting, over time, parameters associated with a patient's analyte levels, according to an embodiment.

FIG. 9C illustrates a method 910 of adjusting, over time, parameters associated with a patient's analyte levels, according to an embodiment. Some of the features in FIG. 9C are the same as or similar to some of the features in FIGS. 1A-9B as noted by same and/or similar reference characters, unless expressly described otherwise. Additionally, reference may be made to features shown in any of FIGS. 1A-9B and not shown in FIG. 9C. In various embodiments, the method 910 may be performed on one device such as the wearable device 100, the invasive analyte measurement device 302, the cloud-based server 306, the user device 308, and so forth. In various embodiments, elements of the method 910 may be performed on separate devices, where the devices form a health device network.

The method 910 may include obtaining a representative analyte level and an analyte level range for a first time period (block 910*a*). The representative analyte level may include, for example, the first initial analyte level 908*a*, the analyte level range may include, for example, the first range of analyte levels 906*a*, and the time period may include, for example, the first time period 904*a*. The representative analyte level may include an average analyte level for the first time period, a median analyte level for the first time period, or a modal analyte level for the first time period. The representative analyte level may include an average of analyte levels less than a median analyte level for the first time period. The representative analyte level may include an analyte level for the user during a specified period of activity, such as during a period of fasting or during a post-prandial period. The representative analyte level may include a mid-range level relative to the coefficient of variation. The representative analyte level may include a level relative to the standard deviation of historical measurements of the user. The representative analyte level may include a representative rate of change of the user's analyte levels. The analyte level range may be a multiple of the standard deviation. The analyte level range may be a multiple of the coefficient of variation. The analyte level range may include a range of rates of change of the analyte level.

The method 910 may include obtaining a representative analyte level and an analyte level range for a second time period such as the second time period 904*b* (block 910*b*). The second time period may be consecutive with the first time period or non-consecutive with the first time period. For example, the first time period may span a day and the second time period may span a day, and a month may separate the first time period and the second time period.

The method 910 may include calculating a change in the representative analyte level and the analyte level range from the first time period to the second time period (block 910*c*). The change may include an increase or a decrease in the representative analyte level. The change may be zero, which may demonstrate the representative analyte level did not change from the first time period to the second time period. The change may include an increase or a decrease in the analyte level range. The method 910 may include determining a quality of the change in the representative analyte level and/or the analyte level range (block 910*d*). The quality may be good, bad, or neutral. For example, the patient's representative analyte level may increase, which may negatively impact the health of the patient. The change in the representative analyte level may accordingly be labeled as "bad" or "poor," and so forth. The patient's analyte level range may decrease, which may positively impact the patient's health. The change in the analyte level range may accordingly be labeled as "good" or "positive," and so forth.

In an embodiment, the change in the representative analyte level and/or the analyte level range may provide an indication of how well a health condition of the user is being managed. For example, a change in the representative analyte level that falls within a normal range for the user may be considered good, whereas a change that falls outside the normal range may be considered bad if it would move the normal range in a bad direction when calculated into the normal range. The normal range may include a multiple of the coefficient of variation, a multiple of the standard deviation, and so forth. The normal range may be a range of rates of change in the user's analyte level. The range of the rates of change may be a multiple of a standard deviation of the user's analyte level rates of change, a percentage of a full range of the change, and so forth.

The method 910 may include communicating the change and/or the quality of the change to a user such as the patient and/or the patient's healthcare provider (block 910*e*). The communication may include audio, visual, and/or tactile communications. In one embodiment, a positive change may be indicated by a green arrow pointing a direction of the change, and a negative change may be indicated by a red arrow pointing in the opposite direction. In another embodiment, the communication may include a text alert delivered to a user device such as the wearable device 100, the invasive analyte measurement device 302, and/or the user device 308.

In various embodiments, a device for identifying improving health of a subject may include: networking hardware communicatively coupled to a wearable device, an invasive glucometer, and a user device; and/or a processing device. The device may, for example, include a cloud-based server (e.g. the cloud-based server 306). The wearable device (e.g. the wearable device 100) may be configured to non-invasively measure a glucose level of a subject wearing the wearable device. The invasive glucometer (e.g. the invasive analyte measurement device 302) may be configured to invasively measure the glucose level of the subject. The user device (e.g. the user device 308) may be configured to display glucose data to a user of the user device. The user may include the subject, a healthcare provider, an insurer, or another third party. The processing device may receive a first set of glucose measurements from the wearable device or the invasive glucometer. The first set of glucose measurements may be taken during a first time period. The first set of glucose measurements may fall within a first range of measurement values. The processing device may receive a second set of glucose measurements from the wearable device or the invasive glucometer. The second set of glucose measurements may be taken during a second time period. The first time period and the second time period may be consecutive or non-consecutive. The second set of glucose measurements may fall within a second range of measurement values. The processing device may determine a change between the first range of measurement values and the second range of measurement values. The processing device may determine a quality of a current diabetic condition of the subject based on whether the change indicates the current diabetic condition of the subject is more healthy or less healthy than a previous diabetic condition of the subject. The processing device may, by the networking hardware, transmit the change and the quality to the user device. The user device may be configured to generate a graphic and display the graphic to the user. The graphic may include the change and the quality.

In various embodiments, the networking hardware may be directly communicatively coupled to the invasive glucometer. The wearable device may be directly communicatively coupled to the invasive glucometer. The invasive glucometer may aggregate measurement data from the wearable device and the invasive glucometer. The processing device may receive the measurement data from the invasive glucometer via the networking hardware. The first set of glucose measurements may correspond to a first representative level. The first representative level may include: a mean, median, or modal level of the first set of glucose measurements; an initial level of the first set of glucose measurements; and/or an average fasting level of the first set of glucose measurements. The second set of glucose measurements may correspond to a second representative level that is different than the first representative level. The second representative level may include: a mean, median, or modal level of the second set of glucose measurements; an initial level of the second set of glucose measurements; and/or an average fasting level of the second set of glucose measurements.

In various embodiments, the first set of glucose measurements and the second set of glucose measurements may be non-overlapping such that: a lowest individual measurement of the first set of glucose measurements may be greater than a greatest individual measurement of the second set of glucose measurements; and/or a highest individual measurement of the first set of glucose measurements may be less than a lowest individual measurement of the second set of glucose measurements. The processing device may be configured to: determine the first set of glucose measurements and the second set of glucose measurements are non-overlapping; and/or transmit the difference and the quality upon determining the first set of glucose measurements and the second set of glucose measurements are non-overlapping.

In various embodiments, the processing device may be configured to: track a behavior of the subject; correlate the behavior with the difference and/or the quality; classify the behavior as healthy when the quality of the difference is more healthy; classify the behavior as unhealthy when the quality of the difference is less healthy; and/or transmit a classification of the behavior to the user device. The processing device may be configured to: receive a goal for an average fasting glucose level of the subject from the wearable device or the user device; transmit the difference and the quality when the goal for the average fasting glucose level is reached; and/or transmit a notification the goal is reached. The average fasting glucose level may be calculated from the second set of glucose measurements;

In various embodiments, the first time period may include a fixed length of time. The first time period may start at a first time during a first calendar period and/or may end at a second time during the first calendar period. The second time period may be a same length as the first time period. The second time period may start at the first time during a second calendar period subsequent to the first calendar period and/or may end at the second time during the second calendar period.

In various embodiments, the change may be represented in the graphic as: a first symbol indicating a direction of the change; a first character or a first string of characters indicating a value of the change; and/or a set of lines. The set of lines may include: a first line above a first curve corresponding to the first set of glucose measurements; a second line below the first curve; a third line above a second curve corresponding to the second set of glucose measurements; and/or a fourth line below the second curve. The first line and the second line may define the first range of measurement values. The third line and the fourth line may define the second range of measurement values. The quality may be represented in the graphic as: a first color corresponding to the first range of measurements and a second color corresponding to the second range of measurements; a second symbol; an image; or a second character or a second string of characters.

In various embodiments, a system for identifying improving health of a subject may include: a wearable device configured to non-invasively measure an analyte level of a subject wearing the wearable device; an invasive analyte measurement device configured to invasively measure the analyte level of the subject; a user device configured to display health data to a user of the user device; and/or a processing device communicatively coupled to the wearable device, the invasive analyte measurement device, and/or the user device. The health data may include the analyte level; The user may include the subject, a healthcare provider, or a third party. The processing device may be configured to: receive a first set of analyte measurements from the wearable device or the invasive analyte measurement device; receive a second set of analyte measurements from the wearable device or the invasive analyte measurement device; determine a difference between the first set of analyte measurements and the second set of analyte measurements; correlate the difference with a change in a health condition of the subject; determine a quality of the change in the health condition of the subject based on whether the change is more healthy or less healthy; and/or transmit the difference and the quality to the user device. The first set of analyte measurements may be taken during a first time period. The second set of analyte measurements may be taken during a second time period. The user device may be configured to generate a graphic and display the graphic to the user. The graphic may include the difference and the quality.

In various embodiments, the processing device may be configured to: calculate a first representative analyte level and a first range of measurement values based on the first set of analyte measurements; calculate a second representative analyte level and a second range of measurement values based on the second set of analyte measurements. The difference may be based on a difference between the first representative analyte level and the second representative analyte level. The difference may be based on a difference between the first range of measurement values and the second range of measurement values.

In various embodiments, the first representative analyte level may include: a mean, median, or modal level of the first set of analyte measurements; and/or an initial level of the first set of analyte measurements. The second representative analyte level may include: a mean, median, or modal level of the second set of analyte measurements; and/or an initial level of the second set of analyte measurements. As the second representative analyte level falls within the first range of measurement values, the quality may be represented as neutral. As the second representative analyte level falls above the first range of measurement values, the quality may be represented as bad. As the second representative analyte level falls below the first range of measurement values, the quality may be represented as good.

In various embodiments, the processing device may be configured to: generate a text notification of the quality; and/or transmit the text notification to the wearable device. The wearable device may be configured to: display the text notification to the subject; and/or generate a quality graphic based on the text notification and display the quality graphic. The quality graphic may include an image or a color that indirectly conveys the quality to the subject. The wearable device may aggregate measurement data from the invasive analyte measurement device and the wearable device. The wearable device may send the measurement data as a packet to the processing device. The measurement data may include the first set of analyte measurements or the second set of analyte measurements.

In various embodiments, a method of identifying improving health may include: obtaining a first representative analyte level and a first analyte level range for a first time period; obtaining a second representative analyte level and a second analyte level range for a second time period; calculating a change between the first representative analyte level and the second representative analyte level or between the first analyte level range and the second analyte level range; determining a quality of the change; and/or communicating the change or the quality of the change to a user via a graphical user interface. The first representative analyte level and/or the second representative analyte level may be calculated from non-invasive analyte measurements taken by a wearable device (e.g. the wearable device 100) from a subject wearing the wearable device. The first representative analyte level or the second representative analyte level may be calculated using an invasive analyte measurement taken from the subject by an invasive analyte measurement device (e.g. the invasive analyte measurement device 302). The first analyte level range or the second analyte level range may be based on the non-invasive analyte measurements. The first analyte level range or the second analyte level range may be based on the invasive analyte measurement. The quality of the change may be: neutral if the second representative analyte level falls within the first analyte level range; bad if the second representative analyte level is greater than the first analyte level; and/or good if the second representative analyte level is less than the first analyte level.

In various embodiments, the invasive analyte measurement device may aggregate measurement data from the wearable device. The measurement data from the wearable device may be obtained, via the invasive analyte measurement device, by a processing device remote from the invasive analyte measurement device and the wearable device (e.g. the cloud-based server 306). The processing device may calculate the change and/or may determine the quality of the change. Communicating the change may include generating a graphic that indirectly conveys the quality to the user. The graphic may include: a rectangular shape with a color gradient; a numeral positioned below the rectangular shape, the numeral representing the second representative analyte level; and/or an arrow positioned adjacent to the numeral pointing in a direction relative to the numeral corresponding to the change. An analyte represented by the first representative analyte level or the second representative analyte level may include glucose. The first representative analyte level may include an average glucose level of the subject during the first time period and/or an average fasting glucose level of the subject during the first time period. The second representative analyte level may include an average fasting level of the subject during the second time period and/or an average fasting glucose level of the subject during the second time period. The first representative analyte level may include a first initial invasively measured glucose level of the subject. The first initial invasively measured glucose level may be measured during a first fasting period of the subject. The second representative analyte level may include a second initial invasively measured glucose level of the subject. The second initial invasively measured glucose level may be measured during a second fasting period of the subject.

In various embodiments, a method of identifying improving health may include: calculating, at the processing device, the first representative analyte level and/or the second representative analyte level based on the measurement data after obtaining the measurement data from the wearable device via the invasive analyte measurement device; and/or determining, at the processing device, the first analyte level range or the second analyte level range based on the measurement data after obtaining the measurement data from the wearable device via the invasive analyte measurement device.

Figure 10A:
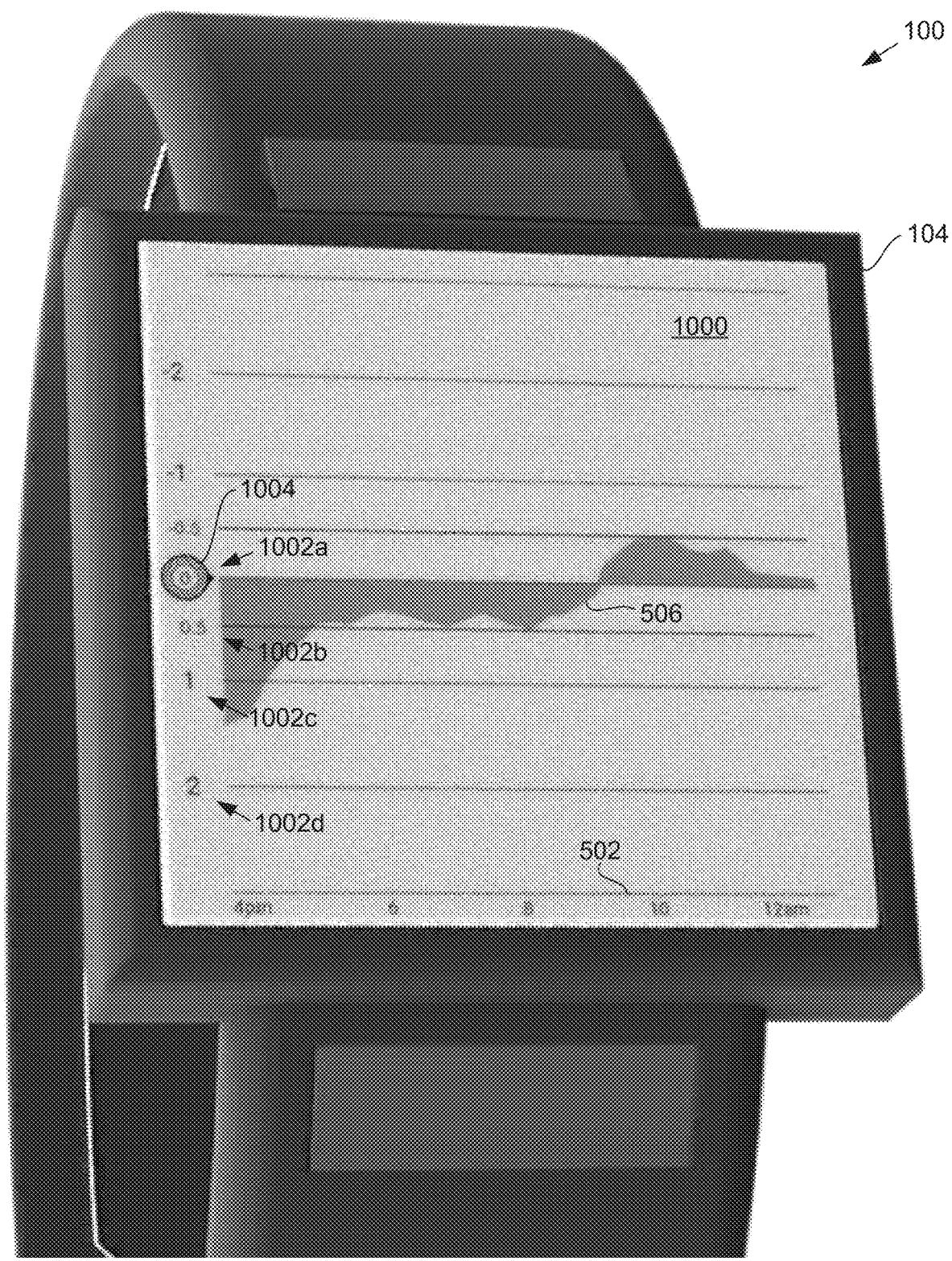
FIG. 10A illustrates a coefficient of variation graph displayed on a user interface of a non-invasive analyte measurement device, according to an embodiment.

FIG. 10A illustrates a coefficient of variation graph 1000 displayed on a user interface of a non-invasive analyte measurement device, according to an embodiment. Some of the features in FIG. 10A are the same as or similar to some of the features in FIGS. 1A-9B as noted by same and/or similar reference characters, unless expressly described otherwise. Additionally, reference may be made to features shown in any of FIGS. 1A-9B and not shown in FIG. 10A. The user interface may include the display device 104 described regarding FIG. 1A. The non-invasive analyte measurement device may include the wearable device 100 described regarding FIG. 1A. The coefficient of variation graph 1000 may include the time axis 502, a coefficient of variation axis 1002, and the curve 506. The coefficient of variation axis 1002 may include a normal level indicator 1002a, a half coefficient of variation indicator 1002b, a full coefficient of variation indicator 1002c, and a two coefficient of variation indicator 1002d. The coefficient of variation graph 1000 may additionally include a real-time status indicator 1004.

In various embodiments, the coefficient of variation indicators may include other multiples of the coefficient of variation such as three, four, five, six, and so forth. In one embodiment, the patient's coefficient of variation may be determined based on the patient's own historical analyte measurement variation. The patient's average analyte measurements may be significantly higher or lower than what may be healthy for the individual. Therefore, healthy measurements may be more than two of the patient's coefficient of variation from the patient's current measurements. Accordingly, as the patient's measurements become more healthy, i.e. lower, during a time period of a same coefficient of variation before the patient's coefficient of variation is adjusted, additional multiples of the coefficient of variation may be included on the coefficient of variation graph 1000 to account for the lower measurements. In another embodiment, the patient's average analyte measurements may be significantly lower than what may be healthy for the individual. Additional multiples of the coefficient of variation may be included on the coefficient of variation graph 1000 to account for higher measurements as the patient becomes healthier.

The normal level indicator 1002a, in conjunction with the time axis 502 and the curve 506, may indicate when the patient's analyte levels as measured by the wearable device 100 are normal. Normal may refer to average levels of the analyte for the patient specifically. Normal may refer to average levels of the analyte specifically for the patient and during a time period. For example, the analyte may be glucose, and a normal glucose level may include the patient's fasting blood glucose level. Accordingly, the normal level indicator 1002a may indicate to a user of the wearable device 100 when the patient's analyte levels are normal.

Coefficient of variation may refer to a range of values from a normal level of the analyte falling within a safe level. Safe may refer to an analyte level at which the patient does not experience adverse and/or dangerous symptoms due to the analyte level being too far above or too low below the patient's normal analyte level. A full coefficient of variation from the normal analyte level may indicate a level of the analyte at which the patient may begin to experience adverse symptoms. An analyte level two coefficients of variation from the normal analyte level may correspond to the patient experiencing dangerous symptoms. The coefficient of variation may be unique to the patient. Different patients may have different coefficients of variation. In an embodiment, the coefficient of variation may be related to a standard deviation of the analyte measurements from the normal analyte level.

Coefficient of variation may refer to a normal zone of analyte measurements. The normal zone may include a percentage of an entire range of the patient's historical analyte measurements. The normal zone may include a percentage of a range of the patient's historical analyte measurements dating back a specified amount of time. The amount of time may include a day, a few days, a week, a few weeks, a month, a few months, a year, and so forth. The percentage may include: fifty percent to sixty percent of the patient's historical range; sixty percent to seventy percent of the patient's historical range; seventy percent to eighty percent of the patient's historical range; and/or eighty percent to ninety percent of the patient's historical range. The normal zone may be patient-specific, i.e. each patient may have a uniquely determined normal zone based on the patient's own historical range. Using the patient's unique normal zone may enable individualized disease diagnosis and management.

The half coefficient of variation indicator 1002b, in conjunction with the time axis 502 and the curve 506, may indicate when the patient's analyte levels as measured by the wearable device 100 are at, above, and/or within half a coefficient of variation of the patient's normal analyte level. The coefficient of variation may be calculated based on the patient's historical analyte levels, as opposed to historical analyte levels of another individual or a population. Similarly, the full coefficient of variation indicator 1002c may indicate when the patient's analyte levels are at, above, and/or within a full coefficient of variation of the patient's normal analyte level. The two coefficient of variation indicator 1002d may indicate when the patient's analyte levels are at, above, and/or within two coefficients of variation of the patient's normal analyte level. The real-time status indicator 1004 may be placed relative to the level indicators 1002a-d to indicate a current, real-time status of the patient's analyte level, as measured by the wearable device 100, and relative to the patient's normal analyte level.

In an embodiment, the normal level indicator 1002a may include a line parallel to the time axis 502 with the number "0" next to the line. The half coefficient of variation indicator 1002b may include a line parallel to the time axis 502 with the number "0.5" next to the line. The full coefficient of variation indicator 1002c may include a line parallel to the time axis 502 with the number "1" next to the line. The two coefficients of variation indicator 1002d may include a line parallel to the time axis 502 with the number "2" next to the line. Positive values for the coefficient of variation indicators may be positioned below the normal level indicator 1002a.

This may indicate to a user, such as the patient, that lower analyte levels, such as glucose levels, are preferred. Similarly, negative values for the coefficient of variation indicators may be positioned above the normal level indicator 1002a to demonstrate to the user that higher analyte levels are bad.

The lines and numbers associated with the level indicators 1002a-d may have secondary visual indicators to provide additional visual indication to the user of the patient's analyte level. For example, the line and/or number associated with the normal level indicator 1002a may have a first color, the line and/or number associated with the half coefficient of variation indicator 1002b may have a second color, the line and/or number associated with the full coefficient of variation indicator 1002c may have a third color, and/or the line and/or number associated with the two coefficients of variation indicator 1002d may have a fourth color. The first, second, third, and/or fourth colors may fall on a continuous color spectrum. For example, the first color may be green, the second color may be yellow, the third color may be orange, and the fourth color may be red. In another example, the lines and numbers associated with the level indicators 1002a-d may have the same color as each other, and a background of the coefficient of variation graph 1000 may display the spectrum of colors. A background behind the normal level indicator 1002a may be green, a background behind the half coefficient of variation indicator 1002b may be yellow, a background behind the full coefficient of variation indicator 1002c may be orange, and/or a background behind the two coefficients of variation indicator 1002d may be red.

The real-time status indicator 1004 may include a bubble. The bubble may be transparent to allow a background color of the coefficient of variation graph 1000 to show through the bubble, and/or the bubble may be filled with a color. The bubble may hover over the numbers associated with the level indicators 1002a-d to indicate a proximity of the patient's current analyte level to the level indicators 1002a-d. The bubble may be filled in with a color and may include an arrow pointing towards the curve 506. A portion of the color within the bubble may disappear as the bubble hovers over the numbers associated with the level indicators. The color within the bubble may change as the bubble moves relative to the level indicators 1002a-d to provide a secondary indication of the patient's analyte level. The color within the bubble may change continuously along a spectrum ranging from green, through yellow and orange, and ranging to red. The color within the bubble may be green when the patient's analyte level is normal, yellow when the patient's analyte level is half a coefficient of variation from normal, orange when the patient's analyte level is a full coefficient of variation from normal, and red when the patient's analyte level is two coefficients of variation from normal.

The curve 506 may include a color fill between the curve 506 and the normal level indicator 1002a, the half coefficient of variation indicator 1002b, the full coefficient of variation indicator 1002c, and/or the two coefficients of variation indicator 1002d. The color fill may include a gradient ranging along a spectrum corresponding to the level indicators 1002a-d. The color fill may include a solid color. The color fill may be semitransparent to allow a background color of the coefficient of variation graph 1000 to show through the color fill. The color fill may darken the background color.

The normal analyte level for the patient may be dynamically adjusted as analyte data is collected from the patient. For example, a processor associated with the wearable device 100, such as the processing device 102 and/or a processor of a networked device such as another measurement device such as the invasive analyte measurement device 302, a server such as the cloud-based server 306, and/or a user device such as the user device 308 may include programming and/or instructions to determine a normal analyte level for a most recent period of time. The period of time may correspond to a change rate and/or periodicity of the analyte. For example, the period of time may include a day, a week, two weeks, a month, two months, six months, a year, and so forth. Similarly, the processor associated with the wearable device 100 may include programming to determine a range of analyte measurements and corresponding coefficients of variation for the most recent period. The range and coefficients of variation may be dynamically adjusted as the normal analyte level is adjusted using similar methods as those used for dynamically updating the normal analyte level.

In various embodiments, the coefficient of variation graph 1000 may include an indication of a change in the normal analyte level, and so forth. For example, the coefficient of variation graph 1000 may include a first arrow placed on the coefficient of variation graph 1000 to indicate the normal analyte level is changing. The first arrow may point upwards on the coefficient of variation graph 1000 to indicate the normal analyte level is increasing and/or may point down on the coefficient of variation graph 1000 to indicate the normal analyte level is decreasing. The coefficient of variation graph 1000 may include a second arrow placed on the coefficient of variation graph 1000 to indicate the analyte range is changing. The second arrow may point upwards on the coefficient of variation graph 1000 to indicate the analyte level range is increasing and/or may point down on the coefficient of variation graph 1000 to indicate the analyte level range is decreasing.

Figure 10B:
FIG. 10B illustrates a current status display which may enable a wearable device to succinctly communicate a patient's current analyte level, according to an embodiment.

FIG. 10B illustrates a current status display 1006 which may enable the wearable device 100 to succinctly communicate the patient's current analyte level, according to an embodiment. Some of the features in FIG. 10B are the same as or similar to some of the features in FIGS. 1A-10A as noted by same and/or similar reference characters, unless expressly described otherwise. Additionally, reference may be made to features shown in any of FIGS. 1A-10A and not shown in FIG. 10B. The current status display 1006 may include the real-time status indicator 1004 and a set of current status qualifiers 1008. The current status display 1006 may communicate to the user the current status of the patient's analyte levels. The status may be relative to the patient's history, relative to population data, and/or relative to clinically-determined levels. The status may be relative to absolute levels and/or relative changes from an initial level. In an embodiment, the status may be relative to a coefficient of variation of the patient's analyte levels, a standard deviation of the patient's analyte levels, and so forth. The current status qualifiers 1008 may provide a qualitative, as opposed to quantitative, indication of the patient's current analyte level. In various embodiments, the analyte may include water. The current status qualifiers 1008 may provide a qualitative indication of the patient's hydration relative to clinical data on healthy hydration levels. In various embodiments, the analyte may include water. The current status qualifiers 1008 may provide a qualitative indication of the patient's blood glucose level relative to the patient's own blood glucose level history.

The real-time status indicator 1004 may move dynamically on the current status display to align with a current status qualifier 1008 corresponding to the patient's current analyte level. For example, when the patient's analyte level is high, the real-time status indicator 1004 may move to be positioned adjacent to a "Somewhat High" and/or "Very High" current status qualifier 1008. The real-time status indicator 1004 may change color to provide another visual indication of the quality of the patient's current analyte level. Similarly, the current status qualifiers 1008 and/or a background of the current status display 1006 may be color-coded to distinguish between different qualities of the patient's current analyte level and provide secondary visual indication of the quality of the patient's current analyte level. The current status qualifiers 1008 and/or the real-time status indicator 1004 may include words, letters, symbols, and/or colors that may communicate the quality of the patient's current analyte level to the user.

In an embodiment, the real-time status indicator 1004 may include a shape that may be recognized by the user as indicating the analyte measured by, and levels displayed by, the wearable device 100. The current status qualifiers 1008 include words arranged vertically on the current status display 1006 with lines between the words demarking a transition from one current status qualifier 1008 to another current status qualifier 1008.

Figure 10C:
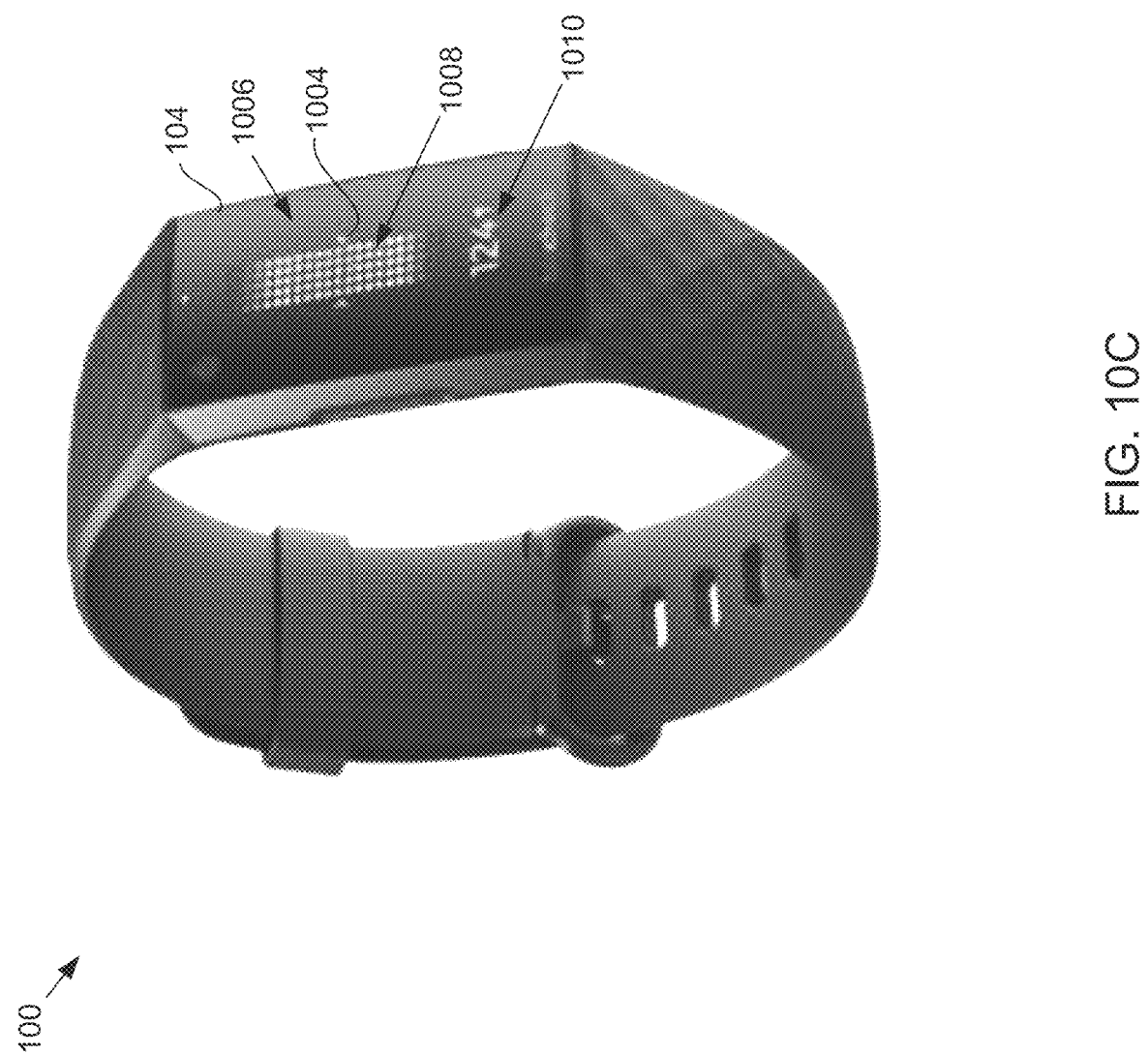
FIG. 10C illustrates an embodiment of the current status display described regarding FIG. 10B including an absolute level indicator, according to an embodiment.

FIG. 10C illustrates an embodiment of the current status display 1006 described regarding FIG. 10B including an absolute level indicator 1010, according to an embodiment. Some of the features in FIG. 10C are the same as or similar to some of the features in FIGS. 1A-10B as noted by same and/or similar reference characters, unless expressly described otherwise. Additionally, reference may be made to features shown in any of FIGS. 1A-10B and not shown in FIG. 10C. In an embodiment, the current status qualifier 1008 may include a color scale. The color scale may correspond to the patient's coefficient of variation. For example, the color scale may include green indicating the patient's analyte level is within a range of the coefficient of variation, yellow indicating the patient's analyte level is approaching a boundary of the range of the coefficient of variation, and red indicating the patient's analyte level is outside the range of the coefficient of variation. In another example, green may indicate a range of analyte measurements up to eighty percent of the patient's coefficient of variation, yellow may indicate a range of analyte measurements up to one hundred percent of the patient's coefficient of variation, and red may indicate a range of analyte measurements greater than one hundred percent of the patient's coefficient of variation.

In an embodiment, the real-time status indicator 1004 may include an arrow pointing to a region of the color scale corresponding to the patient's current analyte level. The current analyte level may be an absolute level, may be relative to a coefficient of variation of the patient's historical analyte levels, or may be relative to a standard deviation of the patient's historical analyte levels. The absolute level indicator 1010 may include a numerical indication of a value of the patient's current analyte level. For example, the analyte may include blood glucose. The absolute level indicator 1010 may include a numerical indication of the patient's current $A_{1c}$ level and/or of the patient's current blood glucose level in milligrams of glucose per deciliter of blood (mg/dL). In one embodiment, the analyte level indicated by the absolute level indicator 1010 may be measured by a non-invasive analyte measurement device such as the wearable device 100. The absolute level indicator 1010 may update continuously as new measurements are taken by the non-invasive analyte measurement device. In one embodiment, the analyte level indicated by the absolute level indicator 1010 may be measured by an invasive analyte measurement device such as the invasive analyte measurement device 302. The absolute level indicator 1010 may update as new measurements by the invasive analyte measurement device are pushed to the wearable device 100.

In an embodiment, a method may include: acquiring a set of glucose measurements from a subject; calculating a coefficient of variation of the set of glucose measurements; generating a display for a user such as the coefficient of variation graph 1000 or the current status display 1006; iteratively receiving new glucose measurements; and iteratively updating the coefficient of variation based on the new glucose measurements. The set of glucose measurements may include an invasive glucose measurement and a non-invasive glucose measurement. The coefficient of variation may be unique to the subject, being calculated from the subject's own set of glucose measurements. The coefficient of variation may include: an amount of variation of individual measurements within a full range of the set of glucose measurements; or a standard deviation of the set of glucose measurements. The amount of variation may correspond to a percentage of the full range. The amount of variation may include a healthy measurement range, wherein outside the healthy measurement range the subject may experience an adverse symptom due to hypoglycemia or hyperglycemia. The user may include the subject, a healthcare provider, or a third party just as a point-of-care engagement center employee, an insurance employee, a friend or family member of the subject, and so forth. The display may be tailored for the user to include relevant information to the user and to exclude irrelevant information to the user. The display may include: a mid-range indicator such as the coefficient of variation axis 1002; the half coefficient of variation indicator 1002b; the full coefficient of variation indicator 1002c; the two coefficients of variation indicator 1002d; and a real-time glucose level indicator such as the real-time status indicator 1004. The real-time glucose level indicator may move on the display to reflect the new glucose measurements. The mid-range indicator, the half coefficient of variation indicator 1002b, the full coefficient of variation indicator 1002c, or the two coefficients of variation indicator 1002d may remain static on the display as the coefficient of variation is updated such that a change in the coefficient of variation is indiscernible by the user as the user views the display.

In an embodiment, a method may include changing a spacing between two or more of the mid-range indicator, the half coefficient of variation indicator 1002b, the full coefficient of variation indicator 1002c, and the two coefficients of variation indicator 1002d. The spacing may be adjusted from a first spacing to a second spacing. The spacing may be adjusted after a minimum time period. The spacing may be adjusted based on an accumulation of the change in the coefficient of variation over the minimum time period. The method may include overlaying the second spacing on the first spacing. The second spacing may be smaller than the first spacing or may be larger than the first spacing.

In an embodiment, a method may include: receiving a physiological measurement directly from a peripheral measurement device; and/or setting the coefficient of variation such that the new glucose measurements fall outside a range of the coefficient of variation. The physiological measurement may indicate a symptom of hyperglycemia or hypoglycemia. The physiological measurement may be taken approximately contemporaneously with the new glucose measurements.

In an embodiment, the change in the coefficient of variation may include a quantity and a direction. The change in the quantity may be indiscernible to the user. The display may include a range indicator that shows whether the coefficient of variation is increased or decreased by the new glucose measurements. In an embodiment, a method may include displaying the range indicator to the user on the display alongside the new glucose measurements.

In an embodiment, a method may include displaying a measurement type indicator alongside the new glucose measurements. The measurement type indicator may show to the user whether the new glucose measurements were taken invasively or non-invasively.

In an embodiment, the wearable device 100 may include a user interface, such as the display device 104, and a processing component. The processing component may be configured to: receive an invasive glucose measurement from the invasive glucometer, the invasive glucose measurement taken from a subject; take a set of non-invasive glucose measurements from the subject using the light source and the miniaturized spectrometer; calculate a coefficient of variation of the set of glucose measurements; display a graphic via the user interface, such as the coefficient of variation graph 1000 and/or the current status display 1006; display the new non-invasive glucose measurement on the graphic; take a new non-invasive glucose measurement; and update the coefficient of variation based on the new non-invasive glucose measurement. The invasive glucose measurement and the set of non-invasive glucose measurements may include a set of glucose measurements. The coefficient of variation may be unique to the subject. The coefficient of variation may include a variation in the set of glucose measurements outside which the subject experiences adverse symptoms due to hypoglycemia or hyperglycemia. The graphic may provide an indication of the coefficient of variation.

In an embodiment, the graphic may include: a mid-range indicator such as the coefficient of variation axis 1002 (i.e. a first line extending across the graphic); a first numeral indicating zero change from a mid-range level of the coefficient of variation; and a coefficient of variation indicator. The coefficient of variation indicator may include: a second numeral indicating a positive change from the mid-range level; a second line, such as one of the coefficient of variation indicators 1002b-d, positioned in the graphic above the mid-range indicator; a third line, such as one of the coefficient of variation indicators 1002b-d, positioned in the graphic below the mid-range indicator; and/or a real-time glucose level indicator such as the real-time status indicator 1004. The second line may indicate an upper range for an upper portion of the coefficient of variation above the mid-range level. The third line may indicate a lower range for a lower portion of the coefficient of variation below the mid-range level. A first spacing between the first line and the second line may be approximately equal to a second spacing between the first line and the third line. The upper coefficient of variation may be different than the lower coefficient of variation.

In an embodiment, the mid-range indicator may include a first color. The coefficient of variation indicator may include: a second color corresponding to a first multiple of the coefficient of variation such as a half multiple, a full multiple, two multiples, and so forth; and a third color corresponding to a second multiple of the coefficient of variation different than the first multiple. The second color may be different from the first color. The third color may be different from the first color. The third color may be different from the second color.

In an embodiment, the first numeral and the second numeral may be positioned along an axis perpendicular to the first line, such as the analyte level axis 504. The axis may be positioned along a left-most end of the first line. The real-time glucose level indicator may include a bubble movably positioned along the axis. The first numeral may be visible behind the bubble as the bubble hovers over the first numeral. The second numeral may be visible behind the bubble as the bubble hovers over the second numeral.

In an embodiment, the mid-range indicator may include a first word displayed on the graphic. The coefficient of variation indicator may include: a second word displayed above the first word on the graphic; and/or a third word displayed below the first word on the graphic. The second word may correspond to a positive multiple of the coefficient of variation. The third word may correspond to a negative multiple of the coefficient of variation. The first word, the second word, and/or the third word may be aligned along a right side of the graphic. The real-time glucose level indicator may include a symbol movably positioned along a left side of the graphic. The real-time glucose level indicator may be vertically moveable to align with the mid-range indicator or the coefficient of variation indicator corresponding to a current glucose level of the subject.

In an embodiment, the graphic may include a color gradient. The mid-range indicator may include a first region of the color gradient having a first color. The coefficient of variation indicator may include a second region of the color gradient having a spectrum of colors. The real-time glucose level indicator may include an arrow movably positioned along a side of the color gradient. The real-time glucose level indicator may be moveable along the color gradient to align within the mid-range indicator or the second region of the coefficient of variation indicator corresponding to a current glucose level of the subject.

In an embodiment, the graphic may include an invasive measurement indicator and a non-invasive measurement indicator. The non-invasive measurement indicator may include the color gradient and/or the real-time glucose level indicator. The invasive measurement indicator may include a numeral positioned below the color gradient. The numeral may represent a value of the invasive glucose measurement.

In an embodiment, a method may include: acquiring a set of analyte measurements of an analyte from a subject; calculating a coefficient of variation of the set of analyte measurements; generating a display for the subject comprising an indication of the coefficient of variation; receiving a new analyte measurement; displaying the new analyte measurement to the subject via a user interface; and updating the coefficient of variation based on the new analyte measurement. The set of analyte measurements may include an invasive analyte measurement and a non-invasive analyte measurement. The coefficient of variation may be unique to the subject. The coefficient of variation may include a variation in the set of analyte measurements outside which the subject experiences adverse symptoms due to having too much of the analyte or too little of the analyte.

In an embodiment, the invasive analyte measurement may be acquired from an invasive analyte measurement device. The non-invasive analyte measurement may be acquired from a wrist-worn device. The invasive analyte measurement device may be a different device from the wrist-worn device. The invasive analyte measurement device may be directly networked to the wrist-worn device. The invasive analyte measurement may be acquired from the invasive analyte measurement device via the wrist-worn device. The non-invasive analyte measurement may be acquired from the wrist-worn device via the invasive analyte measurement device.

In an embodiment, the coefficient of variation may be calculated on a server such as the cloud-based server 306. The server may be different from a measurement device that takes the invasive analyte measurement, such as the invasive analyte measurement device 302, or the non-invasive analyte measurement, such as the wearable device 100. The display may be generated on a user device, such as the user device 308. The user device may be different from the server and the measurement device. The server, the measurement device, and the user device may communicate over an Internet network, such as the health device networks 300$a$-$c$.

In an embodiment, the coefficient of variation may include: a mid-range level; an upper coefficient; and/or a lower coefficient. The upper coefficient may include an upper average analyte measurement for analyte measurements above the mid-range level. The lower coefficient may include a lower average analyte measurement for analyte measurements below the mid-range level.

In an embodiment, a method may include: generating an alert on the display as the new analyte measurement falls outside the coefficient of variation; and/or requesting a new invasive analyte measurement as the new analyte measurement falls outside the coefficient of variation. The new analyte measurement may be a new non-invasive analyte measurement.

In an embodiment, the display may include a historical levels curve and a real-time analyte level indicator. The real-time analyte level indicator may provide a visual indication of a real-time analyte level. The historical levels curve may populate across the display towards a first side of the display as the new analyte measurement is received. The real-time analyte level indicator may be separate from the historical levels curve. The real-time analyte level may be positioned along a second side of the display opposite the first side of the display and opposite a direction in which the historical levels curve populates.

In various embodiments, a wearable device for displaying health information to a user (e.g. the wearable device 100) may include: a band configured in shape and flexibility to fit on a wrist of a subject wearing the band for taking health measurements from the subject; a light source positioned in the band to emit light into the wrist of the subject as the subject wears the band; a miniaturized spectrometer positioned in the band to receive the light through the wrist of the subject as the subject wears the band; a processing device; and/or a touchscreen interface. The processing device may be configured to: activate the light source to emit the light; receive, over time, electronic signals from the miniaturized spectrometer corresponding to measurements of glucose levels of the subject by the miniaturized spectrometer using the light received through the wrist of the subject; transmit the electronic signals to a remote device for processing of the electronic signals to determine the glucose levels of the subject; receive display data indicative of a coefficient of variation of the glucose levels of the subject; and/or generate a coefficient of variation graphic. The coefficient of variation graphic may include: a visual indication of two or more multiples of the coefficient of variation; a visual indication of a mid-range value of the coefficient of variation; and/or a visual indication of a most-recently-measured glucose level of the subject. The touchscreen interface may be configured to display the coefficient of variation graphic to the subject and receive inputs from the subject.

In various embodiments, the remote device may include an invasive glucometer configured to aggregate the electronic signals and transmit the aggregated electronic signals as a batch to a remote server. The remote server is configured to process the electronic signals to generate the measurement data. The measurement data is received by the processing device from the remote server via the invasive glucometer. The wearable device of claim 2, wherein the measurement data is generated by an analytics program securely installed on the remote server such that the subject or another user of the invasive glucometer is prevented from accessing the analytics program via the invasive glucometer. The invasive glucometer may include a pre-existing glucose level management modality of the subject. The invasive glucometer may be portable. The invasive glucometer may measure blood glucose of the subject non-continuously.

In various embodiments, the mid-range value may include: a value at approximately a middle point between an upper limit of the coefficient of variation and a lower limit of the coefficient of variation; a glucose measurement taken from the subject; an average glucose level of the subject averaged over a period of time; a fasting glucose measurement take during a fasting period of the subject; and/or an average fasting glucose level of the subject averaged over the period of time. The measurement data may include non-invasively measured glucose levels of the subject and an invasively measured glucose level of the subject. The non-invasively measured glucose levels may be determined from measurements taken by the miniaturized spectrometer. The invasively measured glucose level may be measured by the remote device.

In various embodiments, the coefficient of variation graphic may include a visual indication of a symptomatic glucose level at which the subject experiences adverse symptoms corresponding with a hyperglycemic state of the subject or a hypoglycemic state of the subject. The visual indication may be relative to one of the visual indications corresponding to the coefficient of variation. The adverse symptoms due to hyperglycemia or hypoglycemia may include: dizziness; nausea; light-headedness; profuse sweating; irregular heartbeat; and/or loss of consciousness. The coefficient of variation graphic may include: a curve displaying historical glucose levels of the subject relative to the coefficient of variation; a list of qualities of a diabetic condition of the subject relative to the coefficient of variation and a symbol indicating the most-recently-measured glucose level; and/or a color gradient representing the representative glucose level and the coefficient of variation and an arrow point to a portion of the color gradient representing the most-recently-measured glucose level. The list of qualities may include: a set of words describing how healthy a glucose measurement is relative to the coefficient of variation; and/or a set of symptoms associated with a set of glucose measurements relative to the coefficient of variation, wherein the set of symptoms are determined based on symptoms experienced by the subject for the set of glucose measurements. The coefficient of variation may be specific to the subject. The coefficient of variation may be determined based on: a measurement history of the subject; a range of values between a maximum measurement of the measurement history and a minimum measurement of the measurement history; and/or a percentage of the range.

In various embodiments, a device for displaying health information to a user may include: a band configured to fit on a wrist of a subject wearing the band; a light source and miniaturized spectrometer positioned in the band to measure analyte levels of the subject as the subject wears the band; a processing device; and/or a user interface. The processing device may be configured to: receive measurement data and/or generate a coefficient of variation graph. The measurement data may include a coefficient of variation of the analyte levels of the subject and/or a current analyte level of the subject. The coefficient of variation graph may include: a time axis aligned horizontally on the coefficient of variation graph; an analyte axis aligned vertically on the coefficient of variation graph perpendicular to the time axis; a first horizontal line extending across the coefficient of variation graph indicating a middle of the coefficient of variation; a curve representing past analyte levels of the subject relative to the coefficient of variation and/or the current analyte level of the subject relative to the coefficient of variation; a second horizontal line extending across the coefficient of variation graph above the first horizontal line indicating an upper threshold of the coefficient of variation; and/or a third horizontal line extending across the coefficient of variation graph below the first horizontal line indicating a lower threshold of the coefficient of variation. The user interface may be configured to display the graph to the subject.

In various embodiments, units of the analyte axis may include: absolute quantities of an analyte indicated by the analyte levels; difference quantities of the analyte calculated from the middle of the coefficient of variation; and/or coefficient of variation intervals from the middle of the coefficient of variation. The middle of the coefficient of variation may be indicated on the analyte axis as a quantity of the analyte. The middle of the coefficient of variation may be indicated on the analyte axis as zero. The middle of the coefficient of variation may be indicated on the analyte axis as zero. In various embodiments, the indicator may include a bubble. The bubble may be positioned over the analyte axis and/or may be aligned with a most-recent coefficient of variation corresponding to the current analyte level of the subject. The bubble and the curve may update dynamically on the coefficient of variation graph as the processing device receives the measurement data to represent the measurement data on the coefficient of variation graph.

In various embodiments, the coefficient of variation graph may include: a negative numerical value aligned with the second horizontal line along the analyte axis; a positive numerical value aligned with the third horizontal line along the analyte axis; and/or an indicator separate from the curve, the first horizontal line, the second horizontal line, and the third horizontal line. The negative numerical value may represent a negative unitless multiple of the coefficient of variation. The positive numerical value may represent a positive unitless multiple of the coefficient of variation. The indicator may provide visual indication of: the current analyte level of the subject relative to the middle of the coefficient of variation, the upper threshold, or the lower threshold; and/or the middle of the coefficient of variation relative to the upper threshold or the lower threshold. In various embodiments, the coefficient of variation graph may include: a first numerical value aligned with the second horizontal line along the analyte axis; and/or a second numerical value aligned with the third horizontal line along the analyte axis. The first numerical value may represent a first analyte level corresponding to the upper threshold. The second numerical value represents a second analyte level corresponding to the lower threshold.

In various embodiments, a device for displaying health information to a user may include: a band configured to fit on a wrist of a subject of the band; a light source and spectrometer positioned in the band to measure analyte levels of the subject as the subject wears the band; a processing device; and/or a user interface. The processing device may be configured to: receive measurement data and/or generate a coefficient of variation graphic. The measurement data may include: a current analyte level of the subject; a coefficient of variation of the analyte levels of the subject; and/or a representative analyte level of the subject. The representative analyte level of the subject may represent a most-healthy analyte level of the subject relative to past analyte levels of the subject and/or the current analyte level. The coefficient of variation graphic may include: a first indirect visual indicator that may indicate the representative analyte level of the subject; a second indirect visual indicator that may indicate a range of the analyte levels of the subject and/or a quality of an individual analyte level in the range of the analyte levels, the quality corresponding to the coefficient of variation; and/or a symbol positioned on the coefficient of variation graphic to indicate a quality of the current analyte level of the subject relative to the representative analyte level and/or the coefficient of variation. The user interface may be configured to display the coefficient of variation graphic to the subject.

In various embodiments, the processing device may be configured to: receive the quality of the current analyte level from a remote server; and/or determine the quality of the current analyte level by comparing the current analyte level to the representative analyte level and the coefficient of variation. The quality of the current analyte level may be determined at the remote server. In various embodiments, the coefficient of variation graphic may include a numerical indication of the current analyte level. The numerical indication of the current analyte level may be positioned on the symbol that indicates the quality of the current analyte level. The second indirect visual indicator may include a set of words that indicate the quality. The set of words may be aligned along a left side of the coefficient of variation graphic. The symbol may be positioned along a right side of the coefficient of variation graphic and/or aligned with a word of the set of words corresponding to the quality of the current analyte level of the subject.

In various embodiments, the second indirect visual indicator may include a rectangular color gradient that radiates from a center portion towards a top portion and a bottom portion. The center portion may include a first color indicating the quality of the current analyte level is good relative to the representative analyte level. The top portion and the bottom portion may include a second color indicating the quality of the current analyte level is bad relative to the representative analyte level. The symbol may straddle the rectangular color gradient. The symbol may be positioned along the rectangular color gradient between the top portion and the bottom portion in a position that indicates the quality of the current analyte level of the subject. A numerical indicator showing the current analyte level of the subject may be positioned below the rectangular color gradient. An arrow may be positioned below the rectangular color gradient. The arrow may indicate: a change of the current analyte level from a previous analyte level; and/or a trend of the analyte levels of the subject towards a more healthy level or a less healthy level relative to past analyte levels.

Figure 11A:
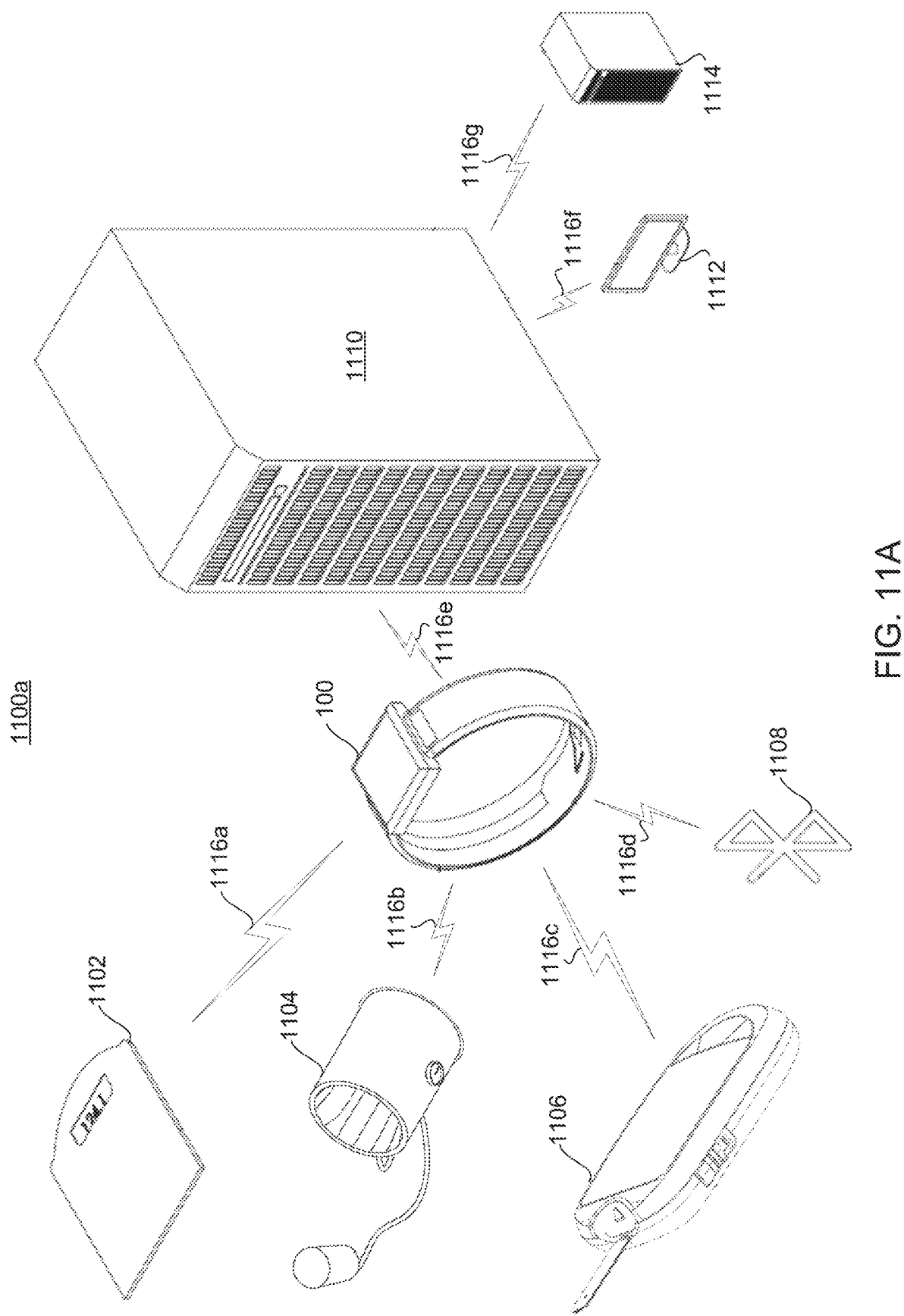
FIG. 11A illustrates a health device network configuration for communicating health data via a wearable device, according to an embodiment.

FIG. 11A illustrates a health device network configuration 1100a for communicating health data via the wearable device 100, according to an embodiment. Some of the features in FIG. 11A are the same as or similar to some of the features in FIGS. 1A-10C as noted by same and/or similar reference characters, unless expressly described otherwise. Additionally, reference may be made to features shown in any of FIGS. 1A-10C and not shown in FIG. 11A.

The health device network configuration 1100a may include the wearable device 100, a weight scale 1102, a blood pressure monitor 1104, an invasive glucometer 1106, a wireless health device 1108, a server 1110, a user device 1112, and a remote device 1114. The wearable device 100 may communicate with the weight scale 1102 via a first network communication link 1116a. The wearable device 100 may communicate with the blood pressure monitor 1104 via a second network communication link 1116b. The wearable device 100 may communicate with the invasive glucometer 1106 via third network communication link 1116c. The wearable device 100 may communicate with the wireless health device 1108 via a fourth network communication link 1116d. The wearable device 100 may communicate with the server 1110 via a fifth network communication link 1116e. The server 1110 may communicate with the user device 1112 via a sixth network communication link 1116E The server 1110 may communicate with the remote device 1114 via a seventh network communication link 1116g.

One or more of the weight scale 1102, the blood pressure monitor 1104, the invasive glucometer 1106, and the wireless health device 1108 may be devices included amongst the peripheral measurement device(s) 304. Accordingly, the weight scale 1102, the blood pressure monitor 1104, the invasive glucometer 1106, and the wireless health device 1108 may include some and/or all of the features described regarding the peripheral measurement device(s) 304. The wireless health device 1108 may include a healthcare device enabled by hardware, software, and/or firmware for wireless networking. The wireless health device 1108 may include a measurement device, a monitoring device, an alerting device, a health data storage device, and so forth.

The server 1110 may include a virtual server and/or a bare metal server. The server may include a personal server owned by the patient and/or an enterprise server owned by the healthcare provider or a third party. In various embodiments, the server 1110 may include a cloud-based server such as the cloud-based server 306. The user device 1112 may be similar to the user device 308. The remote device 1114 may include a user device such as the user device 308. The remote device 1114 may include another server. The other server may include a private server owned by a third party authorized to access the patient's health information such as a health insurer.

The health device network configuration 1100a may include a body area network (BAN), a personal area network (PAN), a near-me area network (NAN), a local area network (LAN), a campus-area network (CAN), a wide area network (WAN), an internet area network (IAN), and/or a public Internet network. The health device network configuration 1100a may include two or more network types. For example, the health device network configuration 1100a may include the PAN, the LAN, and the Internet. In another example, the health device network configuration 1100a may include the BAN, the LAN, and the Internet. The health device network configuration 1100a may include a star topology, a point-to-point topology, a daisy chain topology, and/or a mesh topology. The health device network configuration 1100a may include a hybrid topology including two or more types of network topologies. For example, the health device network configuration 100a may include a star topology and a point-to-point topology.

The health device network configuration 1100a may be situated across a variety of locations including a patient's home, a workplace, a healthcare provider office and/or campus, a data center, a call center, and so forth. For example, the patient may wear the wearable device 10 and carry the invasive glucometer 1106 as the patient travels. The weight scale 1102 may be located in the patient's home. The blood pressure monitor 1104 may be located in the healthcare provider's office and/or at a public location such as a pharmacy. The wireless health device 1108 may be located at the healthcare provider's office. The server 1110, the user device 1112, and/or the remote device 1114 may be located at the patient's home, at the healthcare provider's office, at the data center, and/or at the call center.

The network communication links 1116a-g may include direct wireless links, indirect wireless links, wired links, and/or combinations thereof. In an embodiment, the wearable device 100 may act as a measurement device hub. The wearable device 100 may aggregate measurement data from the weight scale 1102, the blood pressure monitor 1104, the invasive glucometer 1106, and/or the wireless health device 1108 and transmit the aggregated measurement data as a batch to the server 1110. The server 1110 may process the aggregated measurement data as described generally herein regarding data processing. The server 1110 may communicate information regarding the aggregated data, such as analytics, measurement values, and so forth, to the user device 1112 and/or the remote device 1114.

Figure 11B:
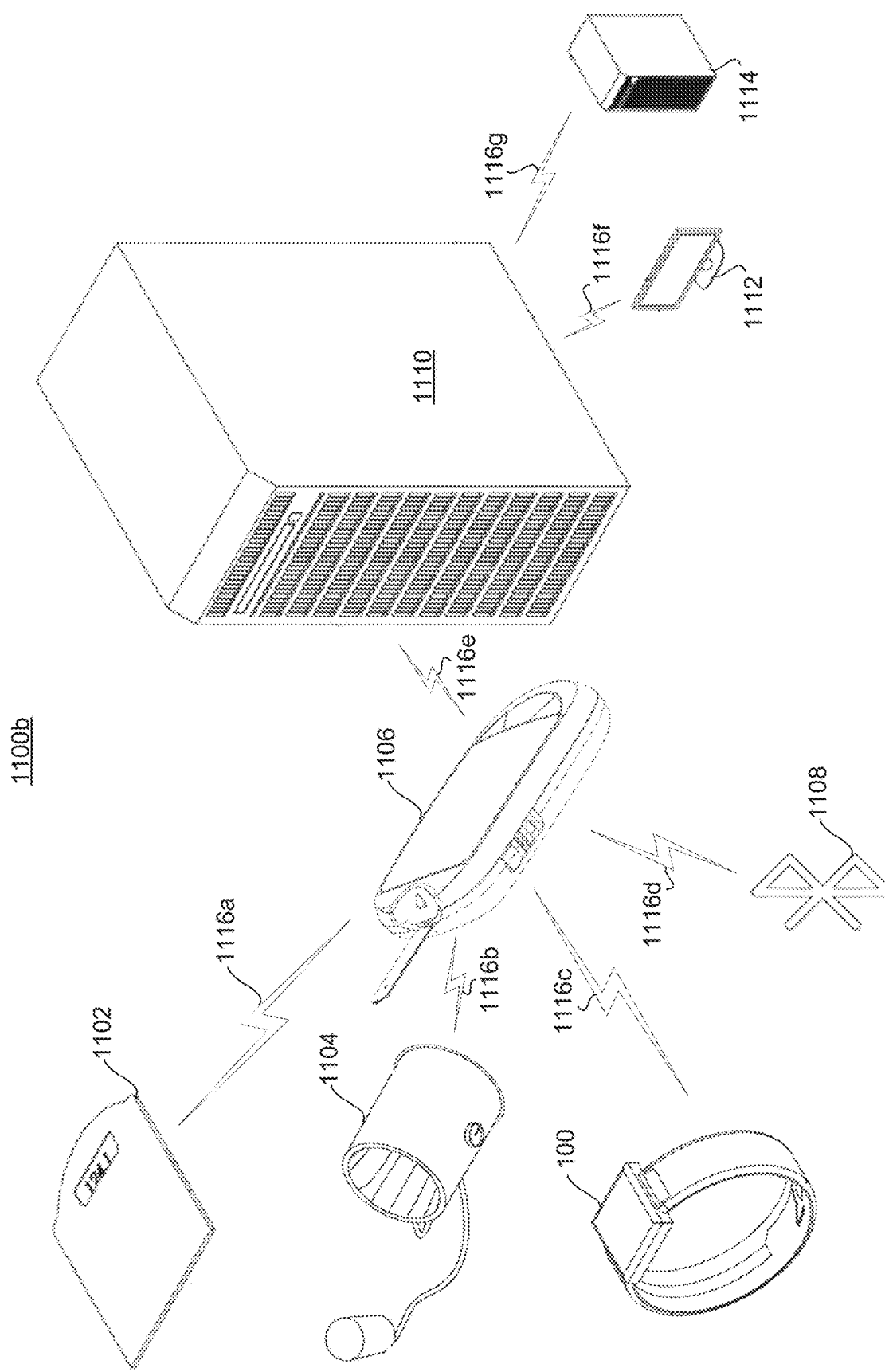
FIG. 11B illustrates a health device network configuration for communicating health data via an invasive glucometer, according to an embodiment.

FIG. 11B illustrates a health device network configuration 1100b for communicating health data via the invasive glucometer 1106, according to an embodiment. Some of the features in FIG. 11B are the same as or similar to some of the features in FIGS. 1A-11A as noted by same and/or similar reference characters, unless expressly described otherwise. Additionally, reference may be made to features shown in any of FIGS. 1A-11A and not shown in FIG. 11B. The health device network configuration 1100b may include the elements of the health device network configuration 1100a, except the wearable device 100 may include a peripheral measurement device and the invasive glucometer may act as the measurement device hub. Measurement data from the weight scale 1102, the blood pressure monitor 1104, the wearable device 100, and/or the wireless health device 1108 may be aggregated by the invasive glucometer 1106 and/or routed to the server 1110 via the invasive glucometer 1106.

In various embodiments, the invasive glucometer 1106 may represent a type of measurement device an individual such as a diabetic may be accustomed to keeping on their person and/or with them. The invasive glucometer 1106 may be portable and/or compact. Thus, the invasive glucometer 1106 may represent a convenient device through which to route data to the server 1110. In some embodiments, routing measurement data through the invasive glucometer 1106 may encourage the individual to keep the invasive glucometer 1106 with them. This incentivization may improve health outcomes. For example, the wearable device 100 may detect the individual has low blood sugar approaching a hypoglycemic state. The wearable device 100 may prompt the individual to take an invasive glucose measurement with the invasive glucometer 1106. The invasive glucometer 1106 may confirm the low blood sugar measurement. The individual may be enabled thereby to prevent the hypoglycemic state.

Figure 12:
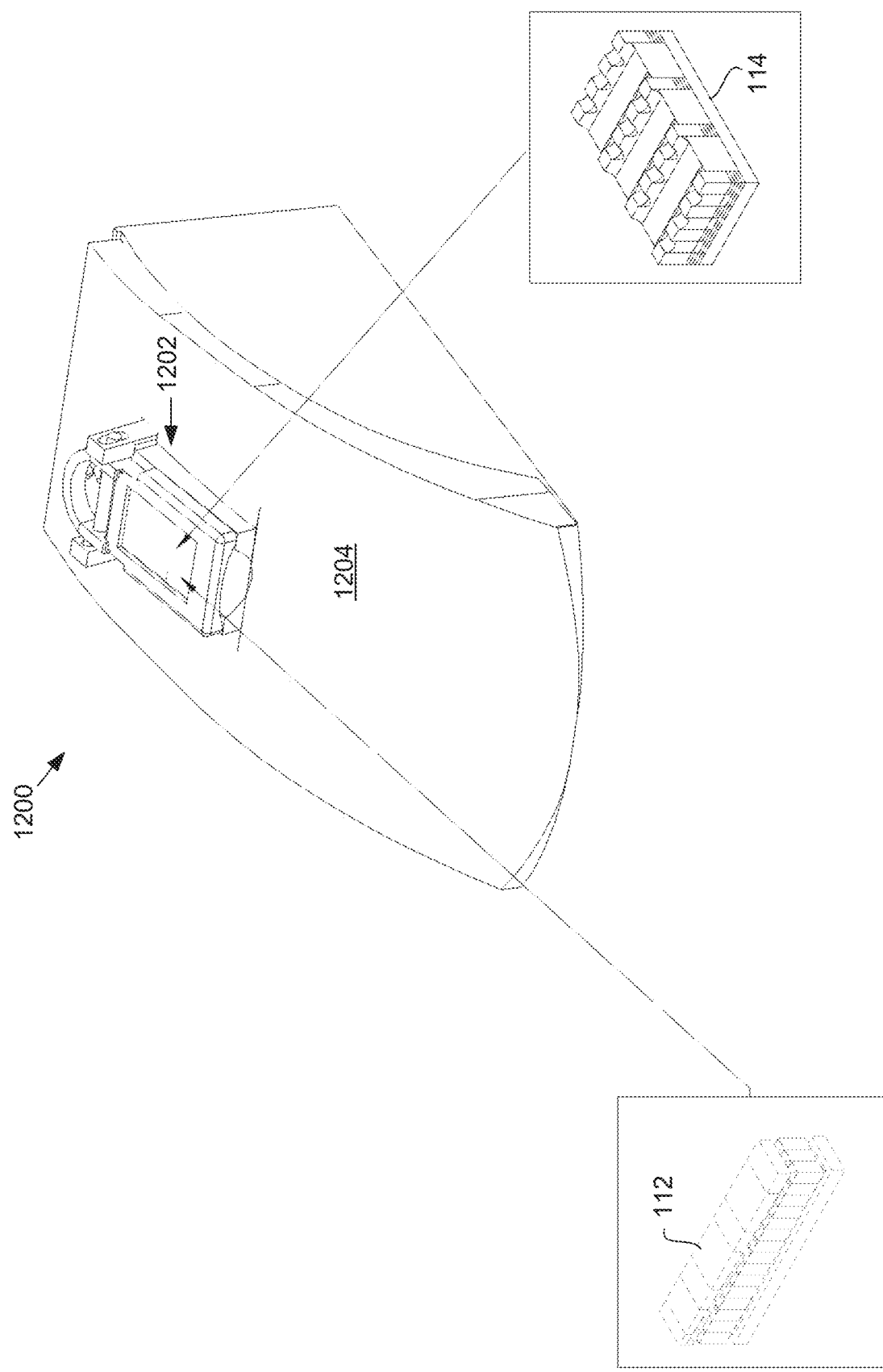
FIG. 12 illustrates a desktop measurement device, according to an embodiment.

FIG. 12 illustrates a desktop measurement device 1200, according to an embodiment. Some of the features in FIG. 12 are the same as or similar to some of the features in FIGS. 1A-11B as noted by same and/or similar reference characters, unless expressly described otherwise. Additionally, reference may be made to features shown in any of FIGS. 1A-11B and not shown in FIG. 12. The desktop measurement device 1200 may include a finger clasp 1202 and a housing 1204. The finger clasp 1202 may have integrated therein one or more biometric sensors such as the first sensor 112 and/or the second sensor 114. The first sensor 112 may include a miniaturized spectrometer and the second sensor 114 may include a miniaturized impedance sensor. The finger clasp 1202 may have one or more light sources integrated therein. The light sources may be positioned in the finger clasp 1202 to be opposite the first sensor 112 as a finger is positioned within the finger clasp. The housing 1204 may be ergonomically shaped to match a resting shape of a patient's hand as a finger of the patient is inserted into the finger clasp 1202. The housing 1204 may additionally be large enough to house power, processing, and/or communication electronics coupled to electronic elements of the finger clasp 1202 such as the first sensor 112, the second sensor 114, and/or the light source. The communication electronics may include wired and/or wireless communication electronics for communication by the desktop measurement device 1200 with other devices such as the user device 308.

Figure 13:
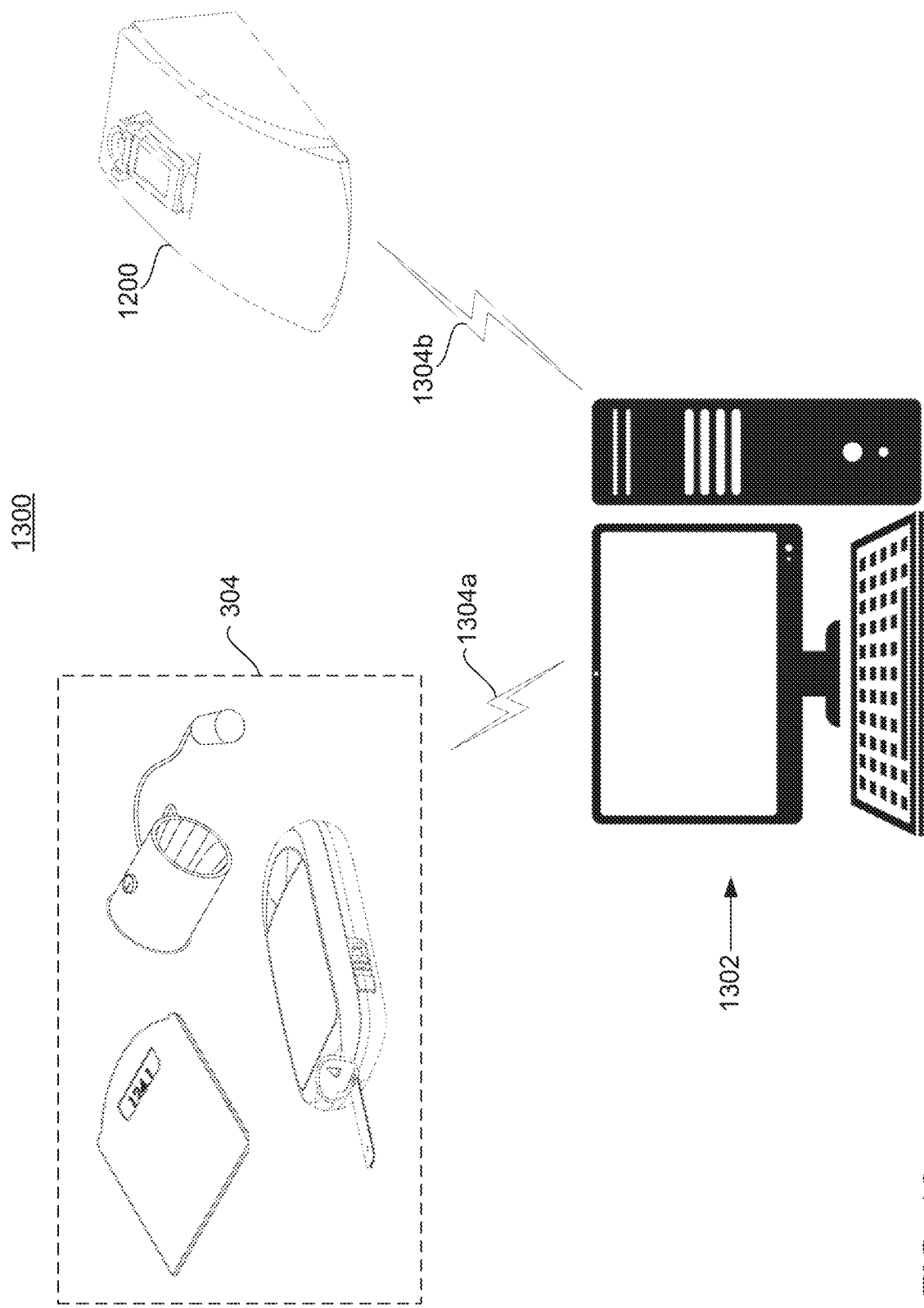
FIG. 13 illustrates a health device network configuration including a personal computer in communication with a desktop measurement device and peripheral measurement devices, according to an embodiment.

FIG. 13 illustrates a health device network configuration 1300 including a personal computer 1302 in communication with the desktop measurement device 1200 and the peripheral measurement device(s) 304, according to an embodiment. Some of the features in FIG. 13 are the same as or similar to some of the features in FIGS. 1A-12 as noted by same and/or similar reference characters, unless expressly described otherwise. Additionally, reference may be made to features shown in any of FIGS. 1A-12 and not shown in FIG. 13. The personal computer 1302 may communicate with the peripheral measurement device(s) 304 via a first network communication link 1304a. The personal computer 1302 may communicate with the desktop measurement device 1200 via a second network communication link 1304b.

The health device network configuration 1300 may include a local area network (LAN), a campus-area network (CAN), a wide area network (WAN), an internet area network (IAN), and/or the Internet. The health device network configuration 1300 may include two or more network types. The health device network configuration 1300 may be situated in and/or across a variety of locations including a patient's home, a workplace, and/or a healthcare provider office and/or campus. For example, the peripheral measurement device(s) 304, the desktop measurement device 1200, and the personal computer may be located in a healthcare provider office. The network communication links 1304a-b may include direct wireless links, indirect wireless links, wired links, and/or combinations thereof.

Figure 14:
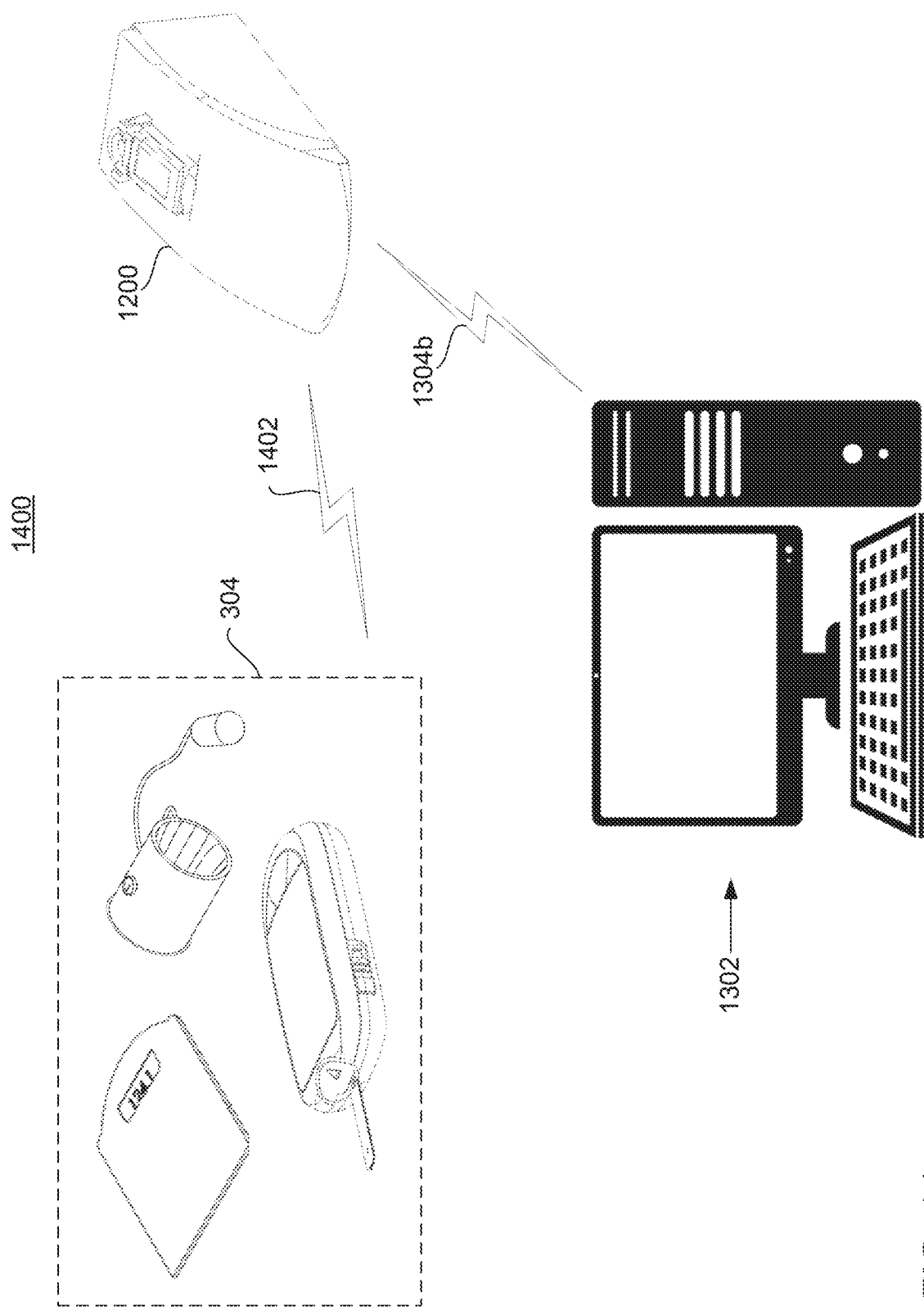
FIG. 14 illustrates a health device network configuration having a desktop measurement device as a network hub, according to an embodiment.

FIG. 14 illustrates a health device network configuration 1400 where the desktop measurement device 1200 acts as a network hub, according to an embodiment. Some of the features in FIG. 14 are the same as or similar to some of the features in FIGS. 1A-13 as noted by same and/or similar reference characters, unless expressly described otherwise. Additionally, reference may be made to features shown in any of FIGS. 1A-13 and not shown in FIG. 14. The health device network configuration 1400 may include the peripheral measurement device(s) 304, the desktop measurement device 1200, and the personal computer 1302. The desktop measurement device 1200 may communicate with the personal computer 1302 over the second network communication link 1304b. The peripheral measurement device(s) 304 may communicate with the desktop measurement device 1200 via a third network communication link 1402. The third network communication link 1402 may include a direct wireless link, an indirect wireless link, a direct wired link, and/or an indirect wired link. The desktop measurement device may act as a hub for the peripheral measurement device(s) 304, aggregating measurements taken by the desktop measurement device 1200 and the peripheral measurement device(s) 304 and passing the aggregated measurement data to the personal computer 1302 in data batches.

Figure 15:
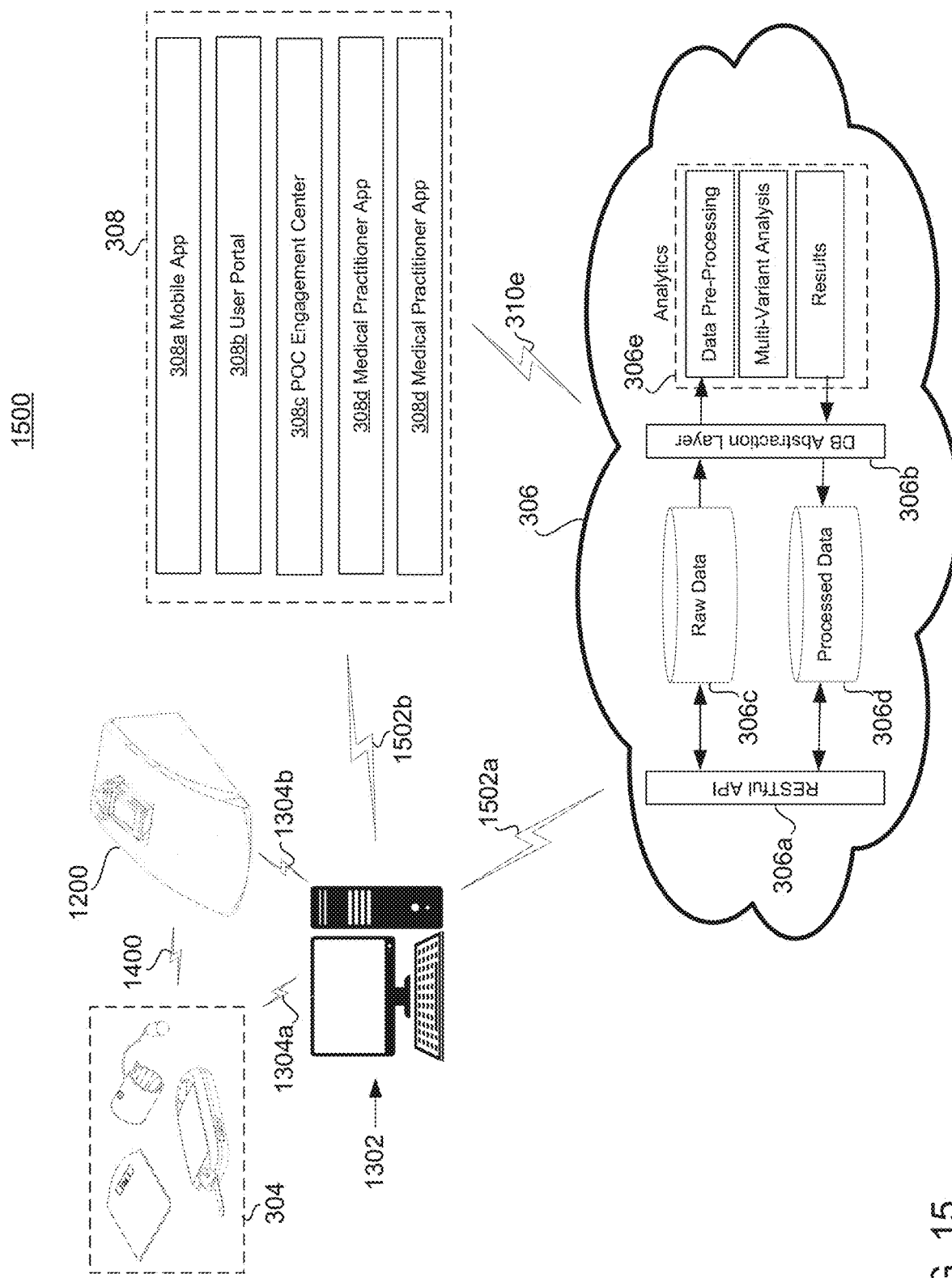
FIG. 15 illustrates a health device network configuration with a desktop measurement device and peripheral measurement devices networked to a cloud-based server through a personal computer, according to an embodiment.

FIG. 15 illustrates a health device network configuration 1500 with the desktop measurement device 1200 and peripheral measurement devices networked to the cloud-based server 306 through the personal computer 1302, according to an embodiment. Some of the features in FIG. 15 are the same as or similar to some of the features in FIGS. 1A-14 as noted by same and/or similar reference characters, unless expressly described otherwise. Additionally, reference may be made to features shown in any of FIGS. 1A-14 and not shown in FIG. 15. The desktop measurement device 1200, the peripheral measurement device(s) 304, and/or the personal computer 1302 may be networked as described regarding FIGS. 13-14. The peripheral measurement device(s) 304 may communicate directly with the personal computer 1302 or through the desktop measurement device 1200. The desktop measurement device 1200 may aggregate measurement data and communicate the data to the personal computer 1302.

The personal computer 1302 may act as a measurement device hub. The personal computer 1302 may aggregate measurement data from the peripheral measurement device(s) 304 and/or the desktop measurement device 1200. The aggregated measurement data may be communicated from the personal computer to the cloud-based server 306 over a fourth network communication link 1502*a*. The cloud-based server 306 may store the aggregated data, process the aggregated data, and/or communicate analytics associated with the aggregated measurement data to the personal computer 1302 and/or the user device 308. The personal computer 1302 may communicate measurement data directly to the user device 308 over the fifth network communication link 1502*b*. The measurement data communicated from the personal computer 1302 to the user device 308 may include one or more measurements by an individual device, may include a batch of measurement data from two or more devices, and/or may include the aggregated measurement data.

Figure 16:
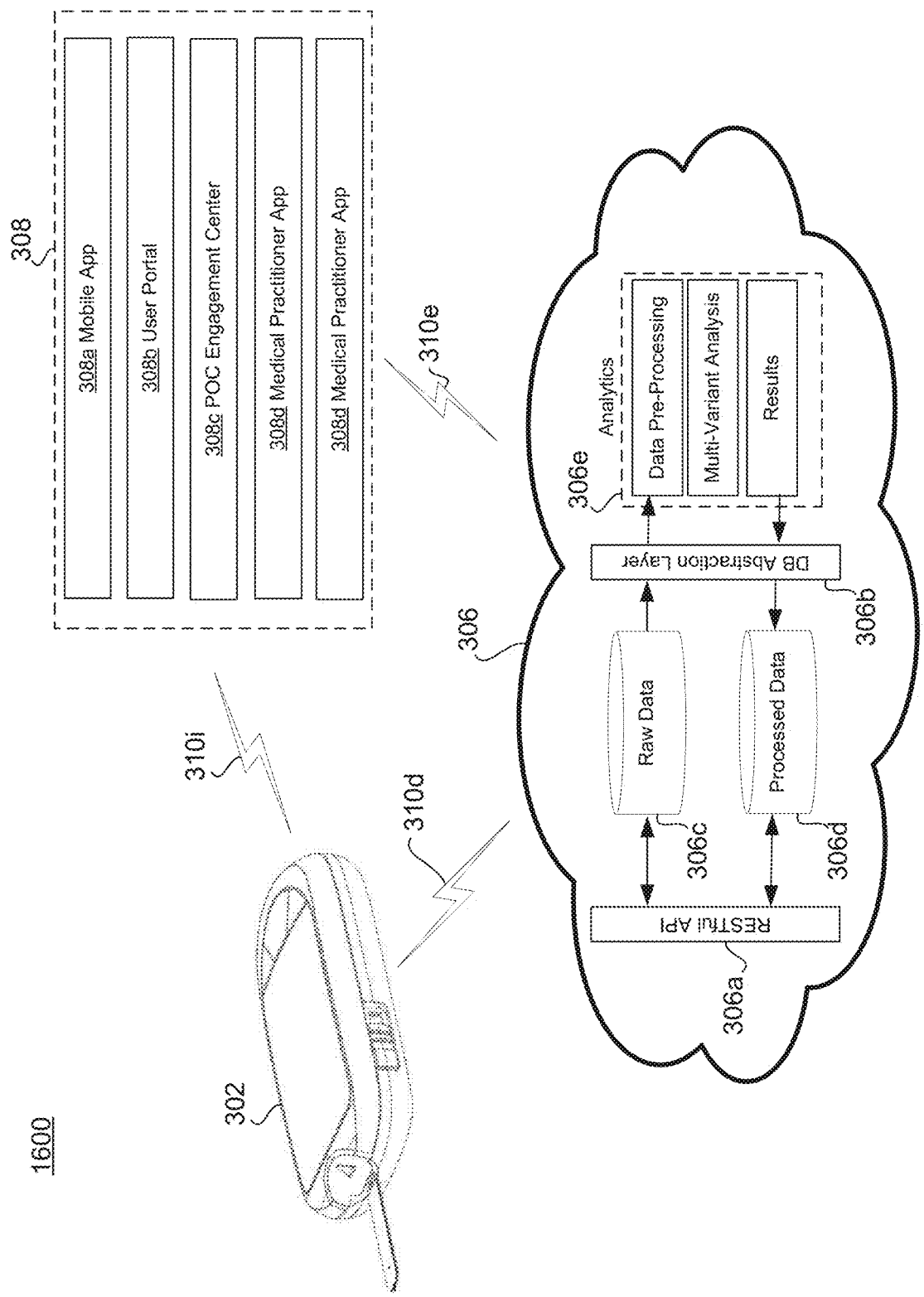
FIG. 16 illustrates a health device network configuration including an invasive analyte measurement device in direct communication with a cloud-based server and a user device, according to an embodiment.

FIG. 16 illustrates a health device network configuration 1600 including the invasive analyte measurement device 302 in direct communication with the cloud-based server 306 and the user device 308, according to an embodiment. Some of the features in FIG. 16 are the same as or similar to some of the features in FIGS. 1A-15 as noted by same and/or similar reference characters, unless expressly described otherwise. Additionally, reference may be made to features shown in any of FIGS. 1A-15 and not shown in FIG. 16. In an embodiment, the invasive analyte measurement device 302 may include an invasive glucometer. A user, i.e. a patient, may take a glucose reading with the invasive glucometer. The invasive glucometer may communicate the glucose reading to the cloud-based server 306. The cloud-based server 306 may aggregate glucose readings from the invasive glucometer and perform analytics on the aggregated data to determine changes in the patient's health and to predict future trends in glucose readings. The invasive glucometer may communicate the glucose reading to the user device 308. The user device 308 may include a mobile phone running the mobile application 308*a*. The mobile application 308*a* may aggregate glucose readings and display current and/or historical glucose readings to a user of the mobile phone, which may include the patient. The mobile application 308*a* may use the aggregated glucose readings to track progress towards health goals of the patient and provide information to the patient regarding progress towards the goals.

Figure 17A:
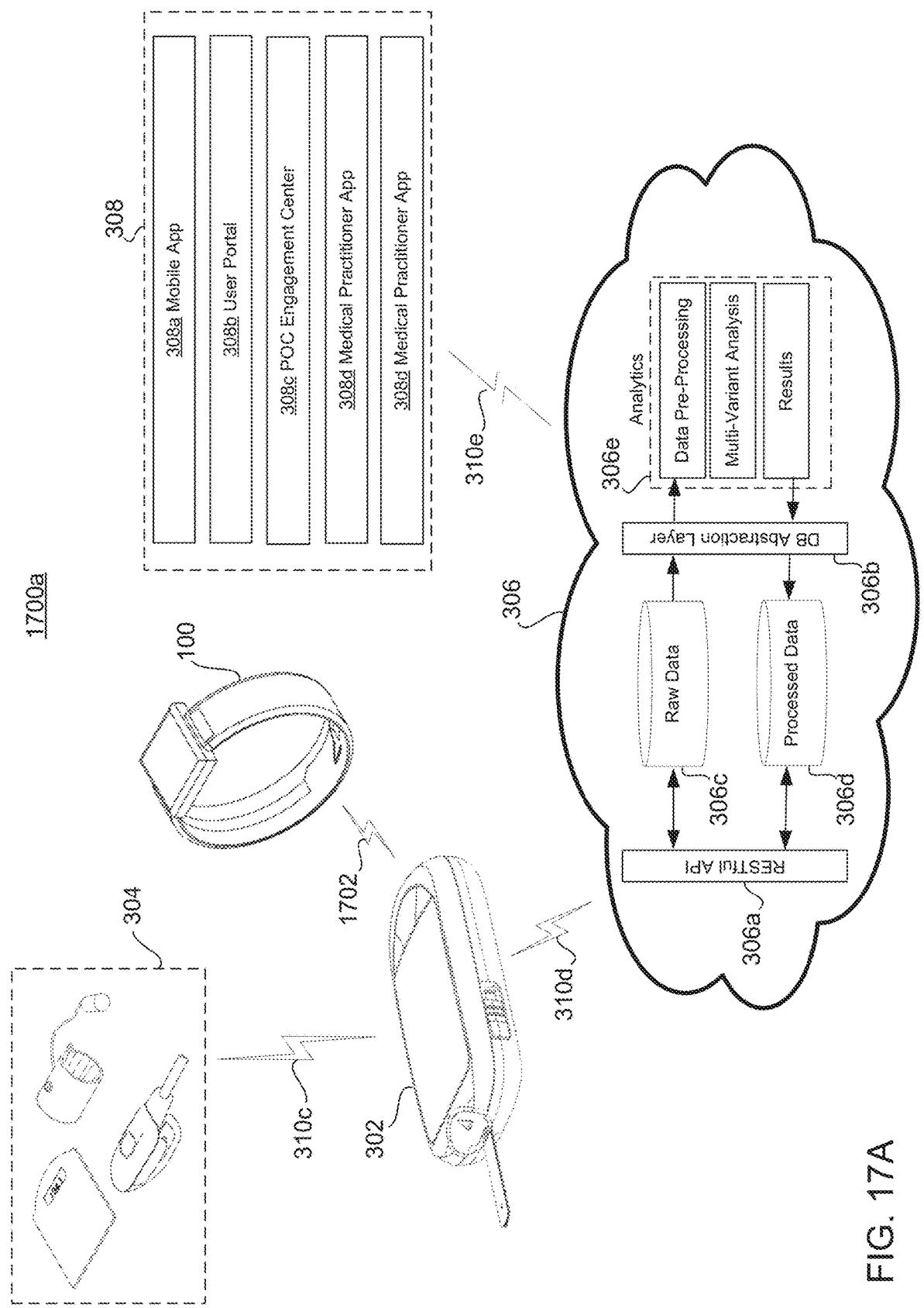
FIG. 17A illustrates a health device network configuration with an invasive analyte measurement device as a measurement device hub for a wearable device and peripheral measurement devices, according to an embodiment.

FIG. 17A illustrates a health device network configuration 1700*a* with the invasive analyte measurement device 302 as a measurement device hub for the wearable device 100 and the peripheral measurement device(s) 304, according to an embodiment. Some of the features in FIG. 17A are the same as or similar to some of the features in FIGS. 1A-16 as noted by same and/or similar reference characters, unless expressly described otherwise. Additionally, reference may be made to features shown in any of FIGS. 1A-16 and not shown in FIG. 17A. The wearable device 100 may communicate with the invasive analyte measurement device 302 via the sixth network communication link 1702. In one embodiment, the invasive analyte measurement device may include an invasive glucometer. The invasive glucometer may aggregate measurement data from the peripheral measurement device(s) 304, the wearable device 100, and the invasive glucometer and communicate the aggregated measurement data in a batch to the cloud-based server 306. The cloud-based server may process the aggregated measurement data and/or analyze the aggregated measurement data to generate a predictive model associated with the aggregated data. The predictive model may be communicated to the user device 308 and/or the invasive glucometer. The invasive glucometer may communicate the predictive model to the wearable device 100.

Figure 17B:
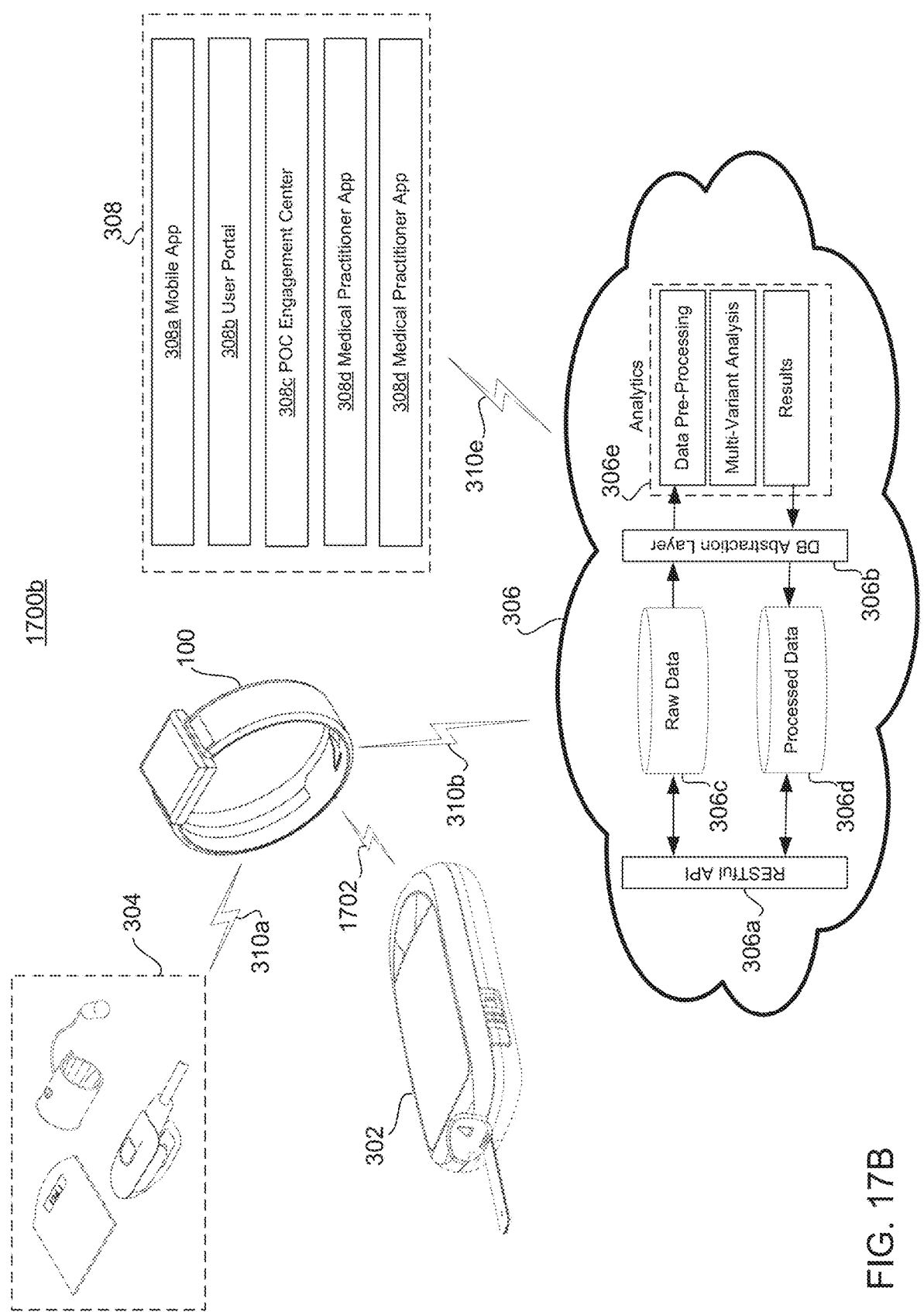
FIG. 17B illustrates a health device network configuration with a wearable device as a measurement device hub for an invasive analyte measurement device and peripheral measurement devices, according to an embodiment.

FIG. 17B illustrates a health device network configuration 1700*b* with the wearable device 100 as a measurement device hub for the invasive analyte measurement device 302 and the peripheral measurement device(s) 304, according to an embodiment. Some of the features in FIG. 17B are the same as or similar to some of the features in FIGS. 1A-17A as noted by same and/or similar reference characters, unless expressly described otherwise. Additionally, reference may be made to features shown in any of FIGS. 1A-17A and not shown in FIG. 17B. The wearable device 100 may aggregate measurement data from the peripheral measurement device(s) 304, the invasive analyte measurement device 302, and the wearable device 100 and communicate the aggregated measurement data in a batch to the cloud-based server 306. The cloud-based server may process the aggregated measurement data and/or analyzed the aggregated measurement data to generate a predictive model associated with the aggregated data. The predictive model may be communicated to the user device 308 and/or the wearable device 100. The wearable device 100 may communicate the predictive model to the invasive analyte measurement device 302.

The above description sets forth numerous specific details such as examples of specific systems, components, methods and so forth, in order to provide a good understanding of several implementations. It will be apparent to one skilled in the art, however, that at least some implementations may be practiced without these specific details. In other instances, well-known components or methods are not described in detail or are presented in simple block diagram format in order to avoid unnecessarily obscuring the present implementations. Thus, the specific details set forth above are merely exemplary. Particular implementations may vary from these exemplary details and still be contemplated to be within the scope of the present implementations.

It is to be understood that the above description is intended to be illustrative and not restrictive. Many other implementations will be apparent to those of skill in the art upon reading and understanding the above description. The scope of the present implementations should, therefore, be determined with reference to the appended claims, along with the full scope of equivalents to which such claims are entitled.

The disclosure above encompasses multiple distinct embodiments with independent utility. While these embodiments have been disclosed in a particular form, the specific embodiments disclosed and illustrated above are not to be considered in a limiting sense as numerous variations are possible. The subject matter of the embodiments includes the novel and non-obvious combinations and sub-combinations of the various elements, features, functions and/or properties disclosed above and inherent to those skilled in the art pertaining to such embodiments. Where the disclosure or subsequently filed claims recite an element, a first element, or any such equivalent term, the disclosure or claims is to be understood to incorporate one or more such elements, neither requiring nor excluding two or more of such elements.

Applicant(s) reserves the right to submit claims directed to combinations and sub-combinations of the disclosed embodiments that are believed to be novel and non-obvious. Embodiments embodied in other combinations and sub-combinations of features, functions, elements and/or properties may be claimed through amendment of those claims or presentation of new claims in the present application or in a related application. Such amended or new claims, whether they are directed to the same embodiment or a different embodiment and whether they are different, broader, narrower or equal in scope to the original claims, are to be considered within the subject matter of the embodiments described herein.

The invention claimed is:

1. A device, comprising: networking hardware configured to communicatively couple to a wearable device, an invasive glucometer, and a user device, wherein:
    the wearable device is configured to non-invasively measure a glucose level of a subject wearing the wearable device;
    the invasive glucometer is configured to invasively measure the glucose level of the subject; and
    the user device is configured to display glucose data to a user of the user device, wherein the user comprises the subject, a healthcare provider, an insurer, or another third party; a processing device configured to:
    receive a first set of glucose measurements from the wearable device or the invasive glucometer, wherein:
        the first set of glucose measurements is taken during a first time period; and
        the first set of glucose measurements fall within a first range of measurement values;
    receive a second set of glucose measurements from the wearable device or the invasive glucometer, wherein:
        the second set of glucose measurements is taken during a second time period;
        the first time period and the second time period are consecutive or non-consecutive; and
        the second set of glucose measurements fall within a second range of measurement values;
    determine a change between the first range of measurement values and the second range of measurement values;
    determine a quality of a current diabetic condition of the subject based on whether the change indicates the current diabetic condition of the subject is more healthy or less healthy than a previous diabetic condition of the subject;
    transmit the change and the quality to the user device, wherein:
        the user device is configured to generate a graphic and display the graphic to the user; and
        the graphic comprises the change and the quality;
    track a behavior of the subject; correlate the behavior with the change and the quality;
    classify the behavior as healthy when the quality of the difference is more healthy;
    classify the behavior as unhealthy when the quality of the difference is less healthy; and
    transmit a classification of the behavior to the user device.

2. The device of claim 1, wherein:
    the networking hardware is directly communicatively coupled to the invasive glucometer;
    the wearable device is directly communicatively coupled to the invasive glucometer;
    the invasive glucometer aggregates measurement data from the wearable device and the invasive glucometer; and
    the processing device receives the measurement data from the invasive glucometer via the networking hardware.

3. The device of claim 1, wherein:
    the first set of glucose measurements correspond to a first representative level, wherein the first representative level comprises:
        a mean, median, or modal level of the first set of glucose measurements;
        an initial level of the first set of glucose measurements; or
        an average fasting level of the first set of glucose measurements; and
    the second set of glucose measurements correspond to a second representative level that is different than the first representative level, wherein the second representative level comprises:
        a mean, median, or modal level of the second set of glucose measurements;
        an initial level of the second set of glucose measurements; or
        an average fasting level of the second set of glucose measurements.

4. The device of claim 1, wherein:
    the first set of glucose measurements and the second set of glucose measurements are non-overlapping such that:
        a lowest individual measurement of the first set of glucose measurements is greater than a greatest individual measurement of the second set of glucose measurements; or
        a highest individual measurement of the first set of glucose measurements is less than a lowest individual measurement of the second set of glucose measurements; and
    the processing device is configured to:
        determine the first set of glucose measurements and the second set of glucose measurements are non-overlapping; and
        transmit the change and the quality upon determining the first set of glucose measurements and the second set of glucose measurements are non-overlapping.

5. The device of claim 1, the processing device is configured to:
    receive a goal for an average fasting glucose level of the subject from the wearable device or the user device, wherein the average fasting glucose level is calculated from the second set of glucose measurements;

transmit the change and the quality when the goal for the average fasting glucose level is reached; and
transmit a notification that the goal is reached.

6. The device of claim 1, wherein:
the first time period comprises a fixed length of time, wherein the first time period:
   starts at a first time during a first calendar period; and
   ends at a second time during the first calendar period; and
the second time period comprises a same length as the first time period, wherein the second time period:
   starts at the first time during a second calendar period subsequent to the first calendar period; and
   ends at the second time during the second calendar period.

7. The device of claim 6, wherein:
the change is represented in the graphic as:
   a first symbol indicating a direction of the change;
   a first character or a first string of characters indicating a value of the change; or
   a set of lines, comprising:
      a first line above a first curve corresponding to the first set of glucose measurements;
      a second line below the first curve, wherein the first line and the second line define the first range of measurement values;
      a third line above a second curve corresponding to the second set of glucose measurements; and
      a fourth line below the second curve, wherein the third line and the fourth line define the second range of measurement values; and
the quality is represented in the graphic as:
   a first color corresponding to the first range of measurement values and a second color corresponding to the second range of measurement values;
   a second symbol;
   an image; or
   a second character or a second string of characters.

8. A system, comprising:
a wearable device configured to non-invasively measure an analyte level of a subject wearing the wearable device;
an invasive analyte measurement device configured to invasively measure the analyte level of the subject;
a user device configured to display health data to a user of the user device, wherein:
   the health data comprises the analyte level; and
   the user comprises the subject, a healthcare provider, or a third party;
a processing device communicatively coupled to the wearable device, the invasive analyte measurement device, and the user device, wherein the processing device is configured to:
   receive a first set of analyte measurements from the wearable device or the invasive analyte measurement device, wherein the first set of analyte measurements is taken during a first time period;
   receive a second set of analyte measurements from the wearable device or the invasive analyte measurement device, wherein the second set of analyte measurements is taken during a second time period, wherein at least one of the first set of analyte measurements forms measurement data aggregated by the wearable device from the invasive analyte measurement device and sent to the processing device as a packet;
   determine a difference between the first set of analyte measurements and the second set of analyte measurements;
   correlate the difference with a change in a health condition of the subject;
   determine a quality of the change in the health condition of the subject based on whether the change is more healthy or less healthy; and
   transmit the difference and the quality to the user device,
wherein:
   the user device is configured to generate a graphic and display the graphic to the user; and
   the graphic comprises the difference and the quality.

9. The system of claim 8, the processing device configured to:
calculate a first representative analyte level and a first range of measurement values based on the first set of analyte measurements; and
calculate a second representative analyte level and a second range of measurement values based on the second set of analyte measurements, wherein:
   the difference is based on a difference between the first representative analyte level and the second representative analyte level; or
   the difference is based on a difference between the first range of measurement values and the second range of measurement values.

10. The system of claim 9, wherein:
the first representative analyte level comprises:
   a mean, median, or modal level of the first set of analyte measurements; or
   an initial level of the first set of analyte measurements; and
the second representative analyte level comprises:
   a mean, median, or modal level of the second set of analyte measurements; or
   an initial level of the second set of analyte measurements.

11. The system of claim 9, wherein:
as the second representative analyte level falls within the first range of measurement values, the quality is represented as neutral;
as the second representative analyte level falls above the first range of measurement values, the quality is represented as bad; and
as the second representative analyte level falls below the first range of measurement values, the quality is represented as good.

12. The system of claim 8, wherein:
the processing device is configured to:
   generate a text notification of the quality; and
   transmit the text notification to the wearable device; and
the wearable device is configured to:
   display the text notification to the subject; or
   generate a quality graphic based on the text notification and display the quality graphic, wherein the quality graphic includes an image or a color that indirectly conveys the quality to the subject.

13. A system, comprising:
a wearable device configured to non-invasively measure an analyte level of a subject wearing the wearable device;
an invasive analyte measurement device directly communicatively coupled to the wearable device configured to invasively measure the analyte level of the subject and aggregate measurement data from the wearable device and the invasive analyte measurement device;

a processing device communicatively coupled to the wearable device, the processing device to receive the measurement data from the invasive analyte measurement device, and a user device, wherein the processing device is configured to:

receive a first set of analyte measurements from the wearable device or the invasive analyte measurement device, wherein the first set of analyte measurements is taken during a first time period;

receive a second set of analyte measurements from the wearable device or the invasive analyte measurement device, wherein the second set of analyte measurements is taken during a second time period;

determine a difference between the first set of analyte measurements and the second set of analyte measurements, wherein the user device is configured:

to generate a graphic indicative of the difference; and
display the graphic to the user.

14. The system of claim 13, wherein the processing device is configured to:

correlate the difference with a change in a health condition of the subject;

determine a quality of the change in the health condition of the subject based on whether the change is more healthy or less healthy; and transmit the difference and the quality to the user device.

15. The system of claim 14, wherein the graphic comprises the difference and the quality.

16. The system of claim 14, wherein the processing device is further configured to determine a quality of the change, wherein the quality of the change is:

neutral if the change falls within an analyte level range;
bad if the change is greater than the analyte level range; or
good if the change is less than the analyte level range.

17. The system of claim 13, wherein:

an analyte represented by the analyte level comprises glucose; and the analyte level comprises an invasively measured glucose level of the subject measured during a fasting period of the subject.

18. The system of claim 13, wherein the system further comprises a user device configured to display health data to a user of the user device, wherein:

the health data comprises the analyte level; and
the user comprises the subject, a healthcare provider, or a third party.

19. The system of claim 13, wherein the processing device is further configured to:

track a behavior of the user;
correlate the behavior with a change and a quality;
classify the behavior as healthy when the quality of the difference is more healthy;
classify the behavior as unhealthy when the quality of the difference is less healthy; and
transmit a classification of the behavior to the user device.

20. The system of claim 13, wherein the wearable device aggregates the first set of analyte measurements or the second set of analyte measurements from the invasive analyte measurement device and the wearable device and sends the measurement data as a packet to the processing device.

* * * * *